United States Patent
Moody et al.

(10) Patent No.: US 10,197,560 B2
(45) Date of Patent: Feb. 5, 2019

(54) **METHODS AND SYSTEMS FOR DETERMINING *M. TUBERCULOSIS* INFECTION**

(71) Applicant: THE BRIGHAM AND WOMEN'S HOSPITAL, INC., Boston, MA (US)

(72) Inventors: David Branch Moody, Brookline, MA (US); Emilie Layre, Boston, MA (US); David C. Young, Haverhill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 256 days.

(21) Appl. No.: 14/900,725

(22) PCT Filed: Jun. 26, 2014

(86) PCT No.: PCT/US2014/044368
§ 371 (c)(1),
(2) Date: Dec. 22, 2015

(87) PCT Pub. No.: WO2014/210327
PCT Pub. Date: Dec. 31, 2014

(65) Prior Publication Data
US 2016/0161471 A1    Jun. 9, 2016

Related U.S. Application Data

(60) Provisional application No. 61/840,125, filed on Jun. 27, 2013.

(51) Int. Cl.
*G01N 33/53* (2006.01)
*G01N 33/92* (2006.01)
*G01N 33/569* (2006.01)
*A61K 31/7076* (2006.01)

(52) U.S. Cl.
CPC ..... *G01N 33/5308* (2013.01); *A61K 31/7076* (2013.01); *G01N 33/5695* (2013.01); *G01N 33/92* (2013.01); *G01N 2333/35* (2013.01); *G01N 2800/52* (2013.01)

(58) Field of Classification Search
None
See application file for complete search history.

(56) References Cited

U.S. PATENT DOCUMENTS

| | | |
|---|---|---|
| 2004/0241826 A1 | 12/2004 | James et al. |
| 2005/0014706 A1* | 1/2005 | Falzari ............... A61K 31/365 514/28 |
| 2006/0014180 A1 | 1/2006 | Jackson et al. |
| 2007/0212740 A1 | 9/2007 | Locht et al. |
| 2009/0111125 A1 | 4/2009 | Verschoor et al. |
| 2010/0008922 A1 | 1/2010 | Hillman |
| 2011/0021367 A1 | 1/2011 | Gopal |
| 2012/0165246 A1 | 6/2012 | Lindner et al. |

FOREIGN PATENT DOCUMENTS

| | | |
|---|---|---|
| WO | 2012151039 A2 | 11/2012 |
| WO | 2013186679 A1 | 12/2013 |

OTHER PUBLICATIONS

Layre et al., "A Comparative Lipidomics Platform for Chemotaxonomic Analysis of *Mycobacterium tuberculosis*", Chem. Biol. 18(12):1537-1549 (2011).
Hinshaw, Corwin, William H. Feldman, and Karl H. Pfuetze. "Treatment of tuberculosis with streptomycin: a summary of observations on one hundred cases." Journal of the American Medical Association 132.13 (1946): 778-782.†

\* cited by examiner
† cited by third party

*Primary Examiner* — Layla D Berry
*Assistant Examiner* — Bahar Craigo
(74) *Attorney, Agent, or Firm* — Nixon Peabody LLP

(57) ABSTRACT

Embodiments of the invention relate to methods and systems for the detection of *Mycobacterium tuberculosis*. *Mycobacterium tuberculosis* kills more than one million people each year. To better understand why *M. tuberculosis* is virulent and to discover chemical markers of this pathogen, we compared its lipid profile to that of the attenuated but related mycobacterium, *Mycobacterium bovis* Bacille Calmette Guerin (BCG). This strategy identified previously unknown compounds that are specific to *M. tuberculosis*, e.g. 1-tuberculosinyladenosine, $N^6$-tuberculosinyladenosine, and various tuberculosinyladenosines having mycolic acids, produced by the Rv3378c enzyme.

7 Claims, 18 Drawing Sheets

FIG. 3A 4,196
*M. TUBERCULOSIS*
TRANSPOSON MUTANTS
↓
RAPID MS
SCREENING FOR
L

N6-TUBERCULOSINYLADENOSINE

FORMULA II

1-TUBERCULOSINYLADENOSINE

FORMULA I

MYCOLYL TUBERCULOSINYLADENOSINE

C85 METHOXY MYCOLATE
$OCH_3$
$m/z$ 1503.3877

C78 ALPHA MYCOLATE
$m/z$ 1387.2676

FORMULA IV

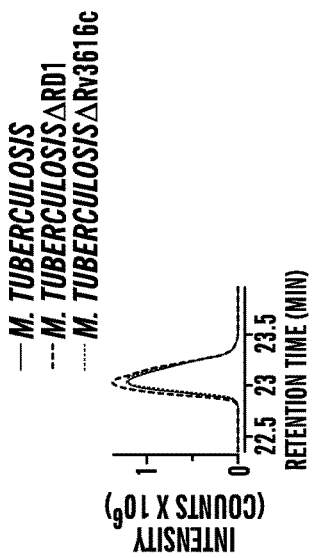
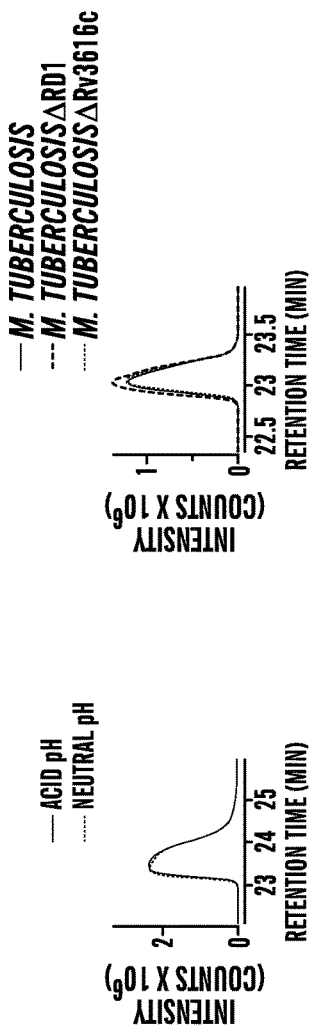
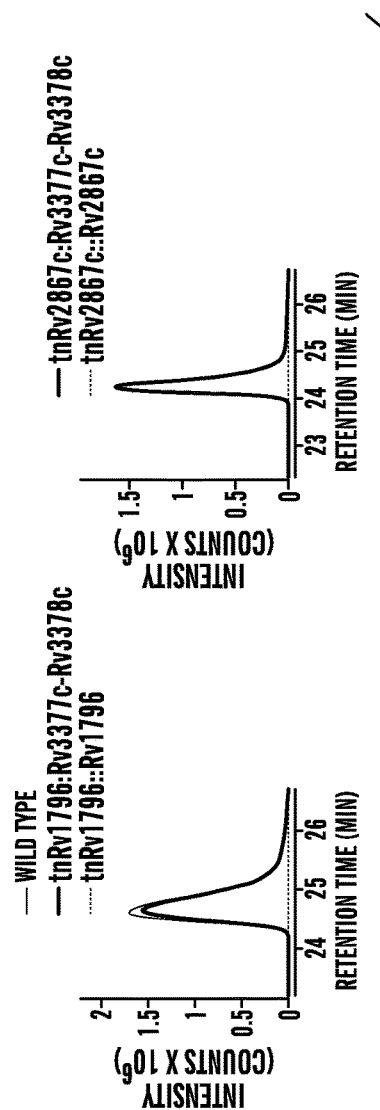
FIG. 8A
FIG. 8B
FIG. 8C
FIG. 9

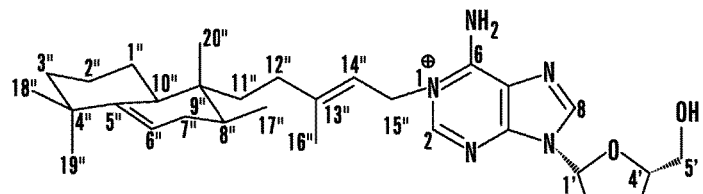

| ATOM | CARBON | HYDROGEN | COSY | NOESY |
|---|---|---|---|---|
| 2 | 147.2 | 8.53 | | 1"$,^2$ 15"$,^2$ 16"$^2$ |
| 8 | 144.2 | 8.66 | | 1', 2', 2, 3'$^2$ |
| 1' | 90.2 | 6.10 (d, 5.2) | 2' | 8,$^2$ 2' |
| 2' | 76.4 | 4.61 (dd, 5.2, 5.1) | 1', 3' | 8,$^2$ 1', 3' |
| 3' | 71.8 | 4.34 (dd, 5.1, 4.1) | 2', 4' | 8,$^2$ 2', 5' |
| 4' | 87.3 | 4.14 (ddd, 4.1, 3.4, 3.1) | 3', 5', 5' | 5', 5' |
| 5' | 62.4 | 3.87 (dd, 12.6, 3.1) | 4', 5' | 4' |
| | | 3.78 (dd, 12.6, 3.4) | 4', 5' | 3', 4' |
| 1α" | 28.4 | 1.77 | 1", 2", 2" | 1", 2", 10" |
| 1β" | | 1.04 | 1", 2", 2" | 1", 2β", 20" |
| 2α" | 23.0 | 1.62 | 1", 1", 3", 3" | 1", 3", 19" |
| 2β" | | 1.62 | 1", 1", 3", 3" | 1", 3" |
| 3α" | 41.9 | 1.41 | 3", 2", 2" | 2", 18", 19" |
| 3β" | | 1.21 (ddd, 13.1, 13.1, 4.8) | 3", 2", 2" | 2", 18" |
| 4" | – | – | | |
| 5" | – | – | | |
| 6" | 117.2 | 5.48 | 7", 7", 10" | 7", 7", 18" |
| 7α" | 32.5 | 1.87 | 6", 7", 8" | 6", 7", 8", 17" |
| 7β" | | 1.77 | 6", 7", 8" | 6", 7", 16", 17", 20" |
| 8" | 34.5 | 1.54 | 7", 7", 17" | 7", 7", 10", 17" |
| 9" | – | – | | |
| 10" | 41.1 | 2.22 (br d, 12.9) | 1", 1", 6" | 2", 7", 10", 12", 19" |
| 11" | 35.5 | 1.58 | 11", 12", 12" | 8", 10", 12", 16", 17", 20" |
| | | 1.42 | 11", 12", 12" | 8", 10", 12", 16", 17", 20" |
| 12" | 33.7 | 2.05 | 11", 11", 12" | 10", 11", 11", 14", 16" |
| | | 2.05 | 11", 11", 12" | 10", 11", 11", 14", 16" |
| 13" | – | – | | |
| 14" | 115.2 | 5.46 | 12", 15", 16" | 2,$^2$ 12", 12" |
| 15" | 49.5 | 4.92$^b$ | 14" | 2,$^2$ 14", 16" |
| | | 4.92$^b$ | 14" | 2,$^2$ 14", 16" |
| 16" | 16.9 | 1.89 | | 2,$^2$ 12", 15" |
| 17" | 15.3 | 0.85 (d, 6.7) | 8" | 7", 7", 8", 11", 11", 20" |
| 18" | 30.1 | 1.06 | | 3", 3", 6", 19" |
| 19" | 29.3 | 1.01 | | 2", 3", 10", 18" |
| 20" | 16.5 | 0.66 | | 1", 7", 11", 17" |

A) THE EXPECTED COSY AND NOESY CROSS PEAKS ARE SEEN WITHIN THE TERPENE, BASE AND SUGAR FRAGMENTS. NOESY CROSS PEAKS BETWEEN THE THREE FRAGMENTS ARE SEEN BETWEEN $H_8$ AND THE THREE SUGAR PROTONS $H_{1'}$, $H_{2'}$ AND $H_{3'}$, AND BETWEEN $H_2$ AND THE TERPENE PROTONS $H_{14"}$, $H_{15"}$, AND $H_{16"}$.
B) THE ALLYLIC METHYLENE PEAK IS THE EXPECTED DOUBLET.

FIG. 15

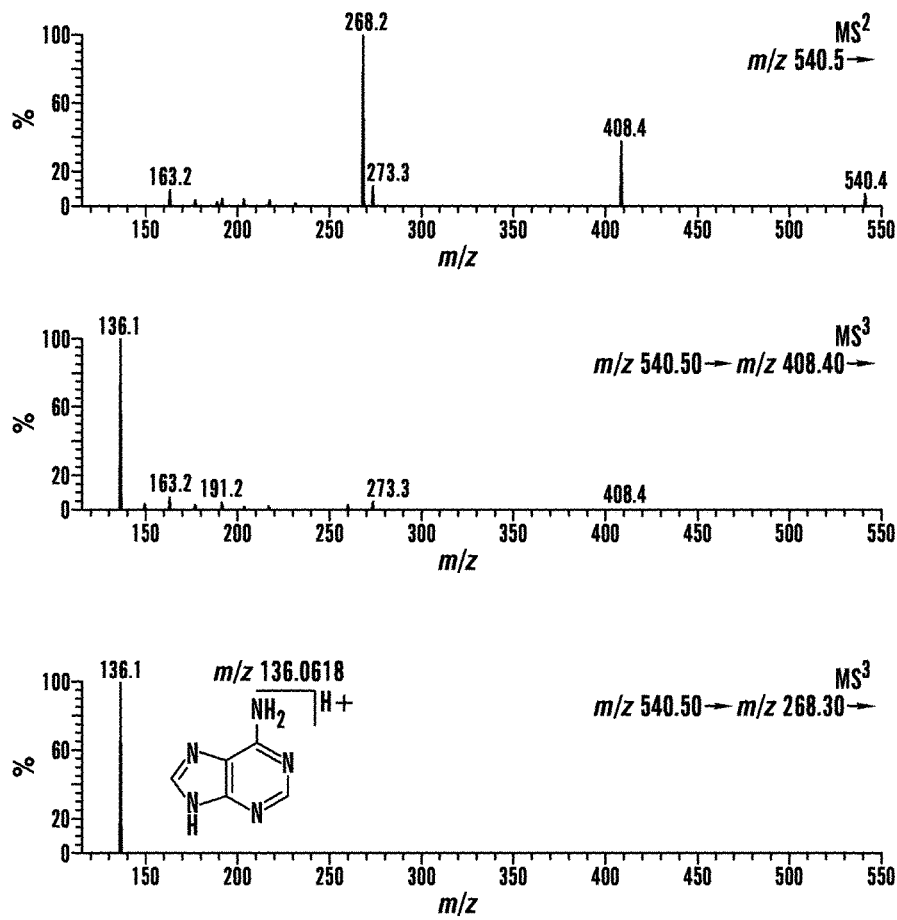
FRAGMENT IONS AT m/z 268 AND m/z 408 IN 1-TbAd BOTH ON PATHWAY TO m/z 136
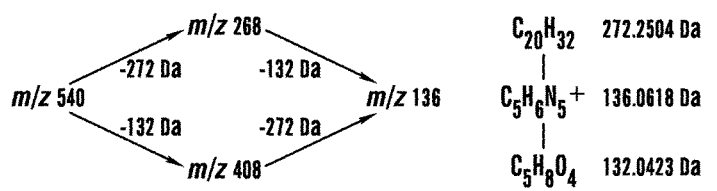
FIG. 16

METHODS AND SYSTEMS FOR DETERMINING *M. TUBERCULOSIS* INFECTION

CROSS-REFERENCE TO RELATED APPLICATION

This application is a 35 U.S.C. § 371 National Phase Entry Application of International Application PCT/US14/44368 filed on Jun. 26, 2014, which designates the US, and which claims the benefit under 35 U.S.C. § 119(e) of U.S. Provisional Application No. 61/840,125 filed Jun. 27, 2013, the contents of each of which are incorporated herein by reference in their entireties.

GOVERNMENT SUPPORT

This invention was made with Government support under grant number RO1-A1049313 awarded by the National Institute of Allergy and Infectious Disease (NIAID). The Government has certain rights in the invention.

FIELD OF INVENTION

Embodiments of the invention are directed to systems and methods for determining whether a subject is infected with *Mycobacterium tuberculosis* (TB).

BACKGROUND OF INVENTION

*Mycobacterium tuberculosis* (*M. tuberculosis*) remains one of the world's most important pathogens, with a mortality rate exceeding 1.5 million deaths annually (Dye C, et al. (2013) *Annu Rev Public Health.* 34:271-286). Despite study of this pathogen for more than a century, the spectrum of natural lipids within *M. tuberculosis* membranes is not yet fully defined. For example, the products of many genes annotated as lipid synthases remain unknown (Camus J C, et al. (2002) Re-annotation of the genome sequence of *Mycobacterium tuberculosis* H37Rv *Microbiology* 148:2967-2973), and mass spectrometry detects hundreds of ions that do not correspond to known lipids in the MycoMass database (Layre E, et al. (2011) A comparative lipidomics platform for chemotaxonomic analysis of *Mycobacterium tuberculosis, Chem Biol* 18(12):1537-1549 provides a method to detect individual lipids that are present in infectious bacteria that cause tuberculosis disease (*M. tuberculosis*) versus attenuated bacteria that are used in vaccines such as BCG. In general, it is important to distinguish patients with tuberculosis from those vaccinated with BCG because the treatments are different and more than 1 billion people have been vaccinated with BCG.

Methods of detecting the presence or absence of the bacteria typically include culturing a sample suspected of having bacteria. However these tests may take over two weeks to complete depending on how long it takes to isolate and grow the bacteria. Accordingly, while such biochemical testing is relatively inexpensive, it is time consuming to grow and subculture bacteria in a sample to reach the minimal concentration of bacteria needed for testing. One standard for the diagnosis of active pulmonary tuberculosis is sputum smear microscopy for acid-fast bacilli. If a patient's sputum tests positive for *M. tuberculosis* they have active pulmonary tuberculosis, are considered highly infectious, and are placed on an exhaustive drug regimen for treatment. However, sputum smear microscopy has low sensitivity and it is estimated that sputum smear microscopy at best detects 25-60% of people with active pulmonary tuberculosis. The method also has relatively poor limits of detection as it requires the presence of at least 10,000 MTb bacilli/mL. An alternative to culture positivity is to detect bacterial DNA by PCR, but such methods are expensive and difficult to use in resource limited settings in which the tuberculosis epidemic is prevalent.

Serologic tests exist for *M. tuberculosis* diagnostics, but they continue to undergo development and tend to be more specific for exposure than active disease. Some commercialized tests use immunodominant antigens to detect immunoglobulin classes (like IgG) in an ELISA or dipstick format. Serological tests are estimated to detect one-third to three-quarters of sputum smear-positive cases of MTb. They detect a significantly smaller portion of smear-negative cases with HIV co-infection. In fact, for people infected with both HIV and MTb, serological tests detect less than one third of patients with the active form of the disease. Many molecular targets of current serological tests, such as mycolic acid and lipoarabinomannan, are produced by mycobacterial in the environment or vaccine strains. It is thought that vaccination or exposure to environmental mycobacteria causes false positive test results in patients with no *M. tuberculosis* infection. Identification of molecular targets that are expressed solely or mainly by *M. tuberculosis* and not other common mycobacteria is therefore expected to yield fewer false positive tests.

A widely used test to determine *M. tuberculosis* (TB) is the PPD (purified protein derivative) skin test. Patients are administered a small shot that contains PPD under the top layer of the skin. A bump or small welt will form, which usually goes away in a few hours. If the area of skin that received PPD is still reactive 48 to 72 hours after the injection, the test results are positive. People who received a BCG (bacille Calmette-Guerin) vaccine against tuberculosis give a false-positive reaction to the PPD test. Many foreign-born people have had the BCG vaccine, though it is not given in the U.S. due to its questionable effectiveness. Accordingly, even if one has been vaccinated, they could still carry the disease. The PPD test does not discriminate between BCG vaccines and patients with *M. tuberculosis* infection and tuberculosis disease. Thus, diagnosis of *M. tuberculosis* infection is complicated by the fact that approximately 1 billion people worldwide have been treated with live *Mycobacterium bovis* Bacille Calmette Guerin (BCG) bacteria as a vaccine, and those persons that have been treated with this vaccine will show a false positive reading in diagnostic tests. In addition, the PPD test also known to show a positive reaction when a subject is infected with non-tuberculosis mycobacteria.

Accordingly, more efficient methods and systems are needed to screen patients suspected of having *M. tuberculosis*. In particular, identification of molecules that are produced by *M. tuberculosis* but not BCG provides the opportunity to develop molecular targets that will not cause false positive serological tests or biochemical tests that directly detect the molecule of interest in ELISA or related methods.

Approximately 1.7 billion are infected with *M. tuberculosis* worldwide. A test that can distinguish people that have been treated with the common BCG vaccine, or that have non-tuberculous mycobacteria, from people that actually have the pathognenic *M. tuberculosis* is of great value.

SUMMARY OF INVENTION

Aspects of the present invention are based, in part, on the discovery of compounds, herein referred to as Formula I, Formula II, Formula III, and Formula IV that are specifically expressed by pathogenic *Mycobacterium tuberculosis* (*M. tuberculosis*), i.e. they are not present in most mycobacteria, including highly related mycobacteria, avirulent (nonpathogenic) mycobacteria and environmental bacteria. Such specific targets are also absent in other non-mycobacterial pathogens that cause diseases that mimic the symptoms of tuberculosis. Significantly, detection of one or more compounds of Formula I-IV, or antibodies that recognize one or more compounds, does not result in false positive readings in subjects that have received the common BCG vaccine, e.g. a positive result correctly indicates that the subject is infected with *M. tuberculosis*. Accordingly, provided herein are methods and computer systems for determining whether a subject is infected with *M. tuberculosis*. Such methods provide a great improvement over the existing diagnostic technologies, 1) the test is specific for *M. tuberculosis*, and 2) the test can distinguish between a person that has been vaccinated for *M. tuberculosis* and is not infected from one who actually is infected with *M. tuberculosis*.

In one aspect, a method of identifying *Mycobacterium tuberculosis* in a subject is provided. The method comprises measuring the presence or absence of at least one compound selected from the group consisting of a compound of Formula I (1-tuberculosinyladenosie), Formula II ($N^6$-tuberculosinyladenosine) and Formula III (a mycoloyl-tuberculosinyladenosine), in a biological sample that is derived from a subject suspected of having *Mycobacterium tuberculosis* infection, wherein the presence of the at least one compound of step a) is indicative that the subject has *Mycobacterium tuberculosis* infection. In one embodiment, the subject is tested in widespread screening of the population to detect tuberculosis. For example, since infection with TB is so prevalent, the entire population can be suspected of having TB infection.

In one embodiment, the presence of the at least two compounds of step a) is indicative that the subject has *Mycobacterium tuberculosis* infection.

In one embodiment, the presence of the at least three compounds of step a) is indicative that the subject has *Mycobacterium tuberculosis* infection.

In one embodiment, the method further comprises administering to the subject a treatment for *Mycobacterium tuberculosis*.

In another aspect, a method for treatment of *Mycobacterium tuberculosis* comprising: administering a pharmaceutically effective amount of a *Mycobacterium tuberculosis* therapeutic to a subject that has the presence of at least one compound selected from the group consisting of a compound of Formula I, Formula II and Formula III.

In one embodiment, the pharmaceutically effective amount of a *Mycobacterium tuberculosis* therapeutic is administered to a subject that has presence of at least two compounds selected from the group consisting of a compound of Formula I, Formula II and Formula III.

In one embodiment, the pharmaceutically effective amount of a *Mycobacterium tuberculosis* therapeutic is administered to a subject that has presence of a compound of Formula I, Formula II and of Formula III.

In another aspect, a method for determining if a subject is responsive to a *Mycobacterium tuberculosis* treatment is provided. The method comprises a) measuring the concentration of at least one compound selected from the group consisting of a compound of Formula I, Formula II and Formula III, in a first sample from a subject; b) administering to the subject a treatment for *Mycobacterium tuberculosis*; and c) measuring the concentration of the one or more compounds of step a) in a second sample from the subject, wherein a decrease in concentration of the compound as compared to the concentration in the first sample is indicative that the subject is responding the treatment for *Mycobacterium tuberculosis* and reducing infection.

In one embodiment of any of the above aspects, the compound is a variant of the compound of Formula III represented by Formula IV (i.e. mycoloyl-tuberculosinyladenosine as provided having R groups of C85 methoxy mycolate and C78 alpha mycolate, or other mycolyl variants described below).

In one embodiment of any of the above aspects, the subject suspected of having *Mycobacterium tuberculosis* infection has been diagnosed as having a bacterial infection.

In one embodiment of any of the above aspects, the subject is human.

In one embodiment of any of the above aspects, the biological sample derived from the subject is selected from the group consisting of: breath, sputum, blood, urine, gastric lavage and pleural fluid.

In one embodiment of any of the above aspects, the presence of the compound is measured using an assay selected from the group consisting of: mass spectrometry (MS), nuclear magnetic resonance spectroscopy and an immunoassay. (e.g. high performance liquid chromatography mass spectrometry (HPLC-MS or collision induced mass spectrometry (CID-MS), or an immunoassay to detect host antibodies against a compound of Formula I-IV.

In one embodiment of any of the above aspects, the assay is an immunoassay that detects the presence of the compound/s by monitoring the presence of host antibodies directed against the compound/s. (e.g. ELISA).

In another aspect, a system for analyzing a biological sample is provided. The system comprises, a) a determination module configured to receive data form measuring a compound present in a biological sample of a subject suspected of having *Mycobacterium tuberculosis* infection (e.g. a subject that is part of a screening protocol), wherein the compound is selected from the group consisting of a compound of Formula I, Formula II and Formula III, and to optionally determine the concentration of the compound; b) a storage device configured to store information from the determination module; c) a comparison module adapted to compare the data stored on the storage device with reference data, and to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection; and d) a display module for displaying a content based in part on the comparison result for the user, wherein the content is a signal indicative that the subject has *Mycobacterium tuberculosis* infection in the presence of at least one compound of step c), or a signal indicative that the subject lacks *Mycobacterium tuberculosis* infection in the absence of each of the compounds of Formula I, Formula II and Formula III.

In one embodiment, in step d) the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c). In one embodiment, in step d) the content is a signal indicative that the subject has *Mycobacterium tuberculosis* infection in the presence of at least three single compounds of step c).

In one embodiment, the system has content that further comprises a signal indicating that the subject should be treated for *Mycobacterium tuberculosis* in the presence of at least one compound selected from the group consisting of Formula I, Formula II, and Formula III.

In one embodiment of the system, the compound of Formula III is represented by Formula IV.

In one embodiment of the system the determination module is configured to receive data from a Mass Spectrometer.

In one embodiment of the system, the subject suspected of having *Mycobacterium tuberculosis* infection has been diagnosed as having a bacterial infection.

In one embodiment of the system, the subject is human.

In one embodiment of the system, the biological sample derived from the subject is selected from the group consisting of: breath, sputum, blood, urine, gastric lavage and pleural fluid.

In one embodiment of the system, the determination module receives data from a mass spectrometer, nuclear magnetic resonance spectroscopy, high performance liquid chromatography, or an immunoassay (e.g. data from an ELISA plate reader).

In another aspect, a computer readable medium having computer readable instructions recorded thereon to define software modules including a comparison module and a display module for implementing a method on a computer is provided. The method implemented in this aspect comprises: a) comparing with the comparison module the data stored on a storage device with reference data to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection, and b) displaying a content based in part on the comparison result for the user, wherein the content is a signal indicative of that the subject has *Mycobacterium tuberculosis* infection in the presence of at least one compound of step a), or a signal indicative that the subject lacks *Mycobacterium tuberculosis* infection in the absence of each of the compounds of Formula I, Formula II and Formula III.

In one embodiment of the computer readable medium, in step b) the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c).

In one embodiment of the computer readable medium, in step b) the content is a signal indicative that the subject has *Mycobacterium tuberculosis* infection in the presence of at least three single compounds of step c).

In one embodiment of the computer readable medium, the compound of Formula III is represented by Formula IV.

In one embodiment of the computer readable medium, the content further comprises a signal indicating that the subject should be treated for *Mycobacterium tuberculosis* in the presence of at least one compound selected from the group consisting of Formula I, Formula II, Formula III and Formula IV.

BRIEF DESCRIPTION OF THE FIGURES

(FIG. 1A) Detected molecular features are shown as a scatterplot of intensity derived from *M. tuberculosis* H37Rv and *M. bovis* BCG lipid extracts. Each feature corresponds to a detected ion and contains retention time and m/z values, which are detailed in Database S1. 1,845 features out of 7,852 total features showed intensity ratios that deviate significantly from 1 (corrected p-value <0.05). The mass spectrum corresponds to the four *M. tuberculosis*-specific features of substance A. (FIG. 1B) Ion chromatograms extracted at m/z (540.3545) and retention time of substance A were used for the analysis of lipid extracts of reference strains. (FIG. 1C) Ion chromatograms from lipidomic analysis of filtered conditioned medium were extracted at the m/z of substance A or control compounds that are secreted (carboxymycobactin) and cell wall-associated lipids (trehalose monomycolate, mycobactin).

FIGS. 3A to 3C show a schematic of the screen to identify *M. tuberculosis* biosynthesis of substance A and graphs indicating that it requires Rv3378c (FIG. 3A) The screening of 4,196 transposon mutants of *M. tuberculosis* H37Rv using a rapid 3 minute HPLC-MS method yielded 30 strains with reduced 1-TbAd signal. (FIG. 3B) Rescreening with regular 40 minute HPLC-MS method confirmed absence of 1-TbAd signal in two mutants. (FIG. 3C) Ion chromatograms, both mutants were found to have spontaneous, non-transposon induced mutations in Rv3378c and were subject to complementation of Rv3377c-Rv3378c and reanalysis for 1-TbAd production.

(FIG. 4A) Rv3377c and Rv3378c are currently thought to produce tuberculosinol and isotuberculosinol. (FIG. 4B) The existence of 1-TbAd might be explained by a revised function of the Rv3378c enzyme, which acts as a tuberculosinyl transferase. Ion chromatograms, mass spectra (insets) (FIG. 4C) and CID-MS (FIG. 4D) of the 1-TbAd standard and reaction products of enzymatic assays performed using recombinant Rv3378c protein (inset, chemical structure). These data prove that recombinant Rv3378c enzyme produces 1-TbAd

(FIG. 6A) Structure of Rv3378c dimer is compared to conventional (Z)-prenyl transferases. (FIG. 6B) Superposition of the active site of Rv3378c and other (Z)-prenyl transferases with the pyrophosphate bound to Rv2361c (stick) shows conserved key residues for substrate binding and catalysis (Rv3378c: blue, Rv2361c: yellow, Rv1086: gray, *E. coli* UPP synthase: magenta for carbon atoms). (FIG. 6C) The monomeric subunits of Rv3378c and Rv2361c were superimposed and Rv2361c substrates (sphere, carbon: yellow/gray, oxygen: red, phosphate: orange) are modeled in the active site of Rv3378c. The conserved residue, Asp34 is shown as a stick model and the magnesium ion is shown as a magenta sphere. (FIG. 6D) Proposed model of Rv3378c shows two substrate pockets with hydrophobic residues lining the predicted prenyl binding pocket and D34 positioned adjacent to the predicted adenosine binding pocket. (FIG. 6B-FIG. 6D) The flexible P-loop of Rv3378c (residues 80-95) is colored in red with dotted line for disordered region (residues 84-90). (FIG. 6E) The translucent surface of Rv3378c was modeled with substrates (spheres) using the same view as (FIG. 6D).

(FIG. 7B) Formula II ($N^6$-tuberculosinyladenosine ($N^6$-TbAd)

FIGS. 8A to 8C shows graphs indicating the detection of M. tuberculosis derived 1-TbAd during (FIG. 8A) exponential or stationary phase (FIG. 8B) in neutral and acid pH medium. Substance A constitutively accumulates independently of the ESX-1 apparatus. Overall, these data show that 1-TbAd is constitutively produced under a wide variety of conditions.

FIG. 9 shows ion chromatograms depicting that complementation of Rv1796 and Rv2867 failed to restore TbAd production. Ions chromatograms extracted at m/z 540.3545 within 10 ppm mass accuracy corresponding to 1-TbAd. In contrary to Rv3377c-Rv337c, the complementation of tnRv1796 or tnRv2867c mutant strains by Rv1796 or Rv2867c, respectively, does not restore the production of TbAd.

FIG. 15 shows a summary of NMR data, with assignments for natural 1-tuberculosinyladenosine from M. tuberculosis. Purified substance A was analyzed in $CD_3OD$ at 800 MHz using a Bruker Avance 800 with this summary supported by spectra the NMR Spectra obtained (not shown).

FIG. 16 shows CID-MS spectra of substance A. The ion detected at m/z 136 (adenine) that arises from collision induced dissociation of either m/z 408 or m/z 268 indicates that both the C20H32 diterpene fragment, lost from m/z 408, and the C5H8O4 fragment, lost from m/z 268, are connected to adenine. The fragmentations leading to m/z 136, 268, and 408 involve hydrogen transfer to the adenine group. The m/z 136 ion arises through sequential losses of 272 Da and 132 Da. These spectra are consistent with a central adenine core structure separately connected to ribose and diterpene units.

Figure 1A:
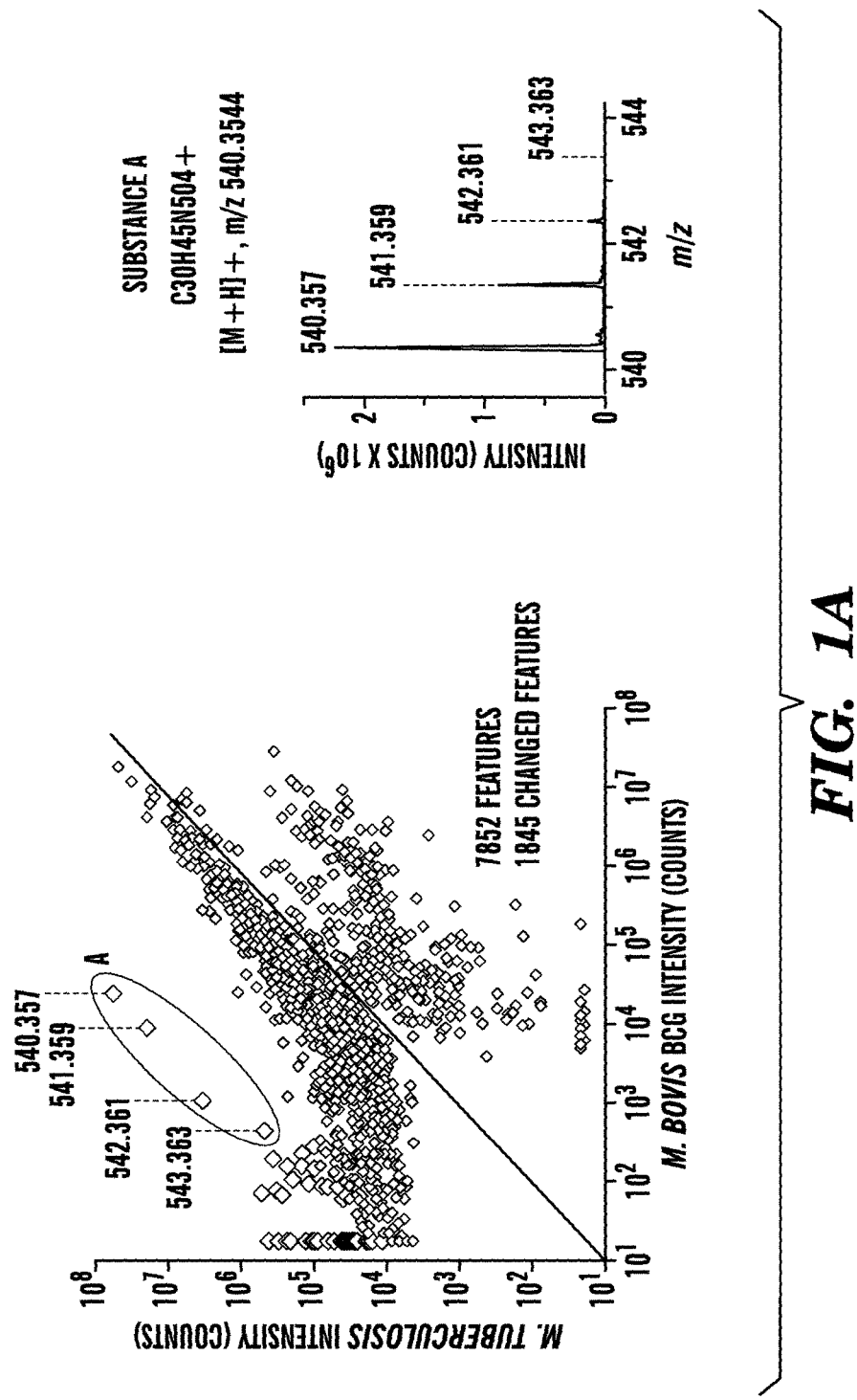
FIGS. 1A to 1C show graphs indicating the comparative lipidomic analysis of *M. tuberculosis* and BCG and reveals a natural product constitutively produced and exported by *M. tuberculosis*.

As used herein the term "Figure" is interchangeable with the term "Fig."

DETAILED DESCRIPTION

Embodiments of the invention are based, in part, upon the discovery of compounds, i.e. Formula I (1-tuberculosinyladenosine (1-TbAd)); Formula II ($N^6$-tuberculosinyladenosine ($N^6$-TbAd); Formula III (a tuberculosinyladenosine comprising mycolic acid) and Formula IV (mycoloyl-tuberculosinyladenosine (MTbAd)), that have been determined to be specific for M. tuberculosis. These compounds are directly useful for the diagnosis of M. tuberculosis infection, and thus are useful for determining a need for treatment of M. tuberculosis in subjects suspected of having M. tuberculosis, e.g. in healthy individuals, in subjects having a bacterial infection, or in subjects exhibiting a symptom of M. tuberculosis). Accordingly, provided herein are methods and computer systems for determining M. tuberculosis infection and treatment.

To identify lipids with roles in tuberculosis disease, we systematically compared the lipid content of virulent Mycobacterium tuberculosis with the attenuated vaccine strain M. bovis BCG. Comparative lipidomics analysis identified more than 1,000 molecular differences, including a previously unknown, M. tuberculosis-specific lipid that is composed of a diterpene unit linked to adenosine. We established the complete structure of the natural product as 1-tuberculosinyladenosine (1-TbAd) (also known as Formula I herein) using mass spectrometry, which was later supported by nuclear magnetic resonance (NMR) spectroscopy. We also identified $N^6$-tuberculosinyladenosine (also known as Formula II herein); a tuberculosinyladenosine comprising mycolic acid (also known as Formula III herein); and mycoloyl-tuberculosinyladenosine (MTbAd), also known as Formula IV herein).

As used herein the terms "Mycobacterium tuberculosis," "TB," "MTb," "M. tuberculosis" and "pathogenic Mycobacterium tuberculosis" are used interchangeably. The term Mycobacterium tuberculosis refers to a pathogenic (e.g. virulent) bacterial species in the family Mycobacteriaceae and a causative agent of tuberculosis (TB) (See Ismael Kassim, Ray C G (editors) (2004) "Sherris Medical Microbiology" (4th ed.)). As used herein the term "pathogenic" refers to a bacterium that is capable of causing disease in a host. TB bacteria usually attack the lungs, but can attack any part of the body such as the kidney, spine, and brain. If not treated properly, TB disease can be fatal. It should be noted that the methods and the systems described herein are capable of detecting latent TB infection because antibody responses are durable during the latent stage, and at least small amounts of the compound are made when the bacterium is alive in the body. As used herein, "latent" TB infection refers to a patient that is infected with Mycobacterium tuberculosis, but the patient does not have active tuberculosis disease that is infectious.

One of skill in the art understands that there are multiple isolates of the same bacteria and that there are multiple strains (isolates) of *M. tuberculosis*. Each of the various isolates of *M. tuberculosis* can be detected using the systems and methods described herein. Some representative isolate strains of *Mycobacterium tuberculosis* include, but are not limited to, *Mycobacterium tuberculosis* EA15/NITR206 Genebank Accession: NC_021194.1; *Mycobacterium tuberculosis* PanR0802 Genebank Accession: NZ_CM002050.1; *Mycobacterium tuberculosis* H37Rv Genebank Accession: NC_000962.3; *Mycobacterium tuberculosis* KZN 1435 Genebank Accession: NC_012943.1; *Mycobacterium tuberculosis* SUMu002 Genebank Accession: NZ_ADHR00000000.1; *Mycobacterium tuberculosis* CCDC5079 Genebank Accession: NC_017523.1; *Mycobacterium tuberculosis* PanR0208 Genebank Accession: NZ_CM002055.1; *Mycobacterium tuberculosis* KZN V2475 Genebank Accession: NZ_CM000788.2; *Mycobacterium tuberculosis* HN878 Genebank Accession: NZ_CM001043.1; *Mycobacterium tuberculosis* H37RvCO Genebank Accession: NZ_CM001515.1; *Mycobacterium tuberculosis* SUMu001 Genebank Accession: NZ_ADHQ00000000.1; *Mycobacterium tuberculosis* S96-129 Genebank Accession: NZ_AEGB00000000.1; *Mycobacterium tuberculosis* PanR1005 Genebank Accession: NZ_CM002051.1; *Mycobacterium tuberculosis* PanR0407 Genebank Accession: NZ_ATEB00000000; *Mycobacterium tuberculosis* PanR0315 Genebank Accession: NZ_ATEJ00000000.1; *Mycobacterium tuberculosis* NA-A0009 Genebank Accession: NZ_ALYH00000000; *Mycobacterium tuberculosis* H37Rv Genebank Accession: NC_000962.3; *Mycobacterium tuberculosis* str. Beijing/NITR203 Genebank Accession: NC_021054.1; *Mycobacterium tuberculosis* H37Ra Genebank Accession: NC_009525.1; *Mycobacterium tuberculosis* F11 Genebank Accession: NC_009565.1; *Mycobacterium tuberculosis* 7199-99 Genebank Accession: NC_020089.1; *Mycobacterium tuberculosis* str. Haarlem Genebank Accession: NC_022350.1; *Mycobacterium tuberculosis* CDC1551 Genebank Accession: NC 002755.2; *Mycobacterium tuberculosis* str. Erdman=ATCC 35801 NC_020559.1.

In one embodiment the *Mycobacterium tuberculosis* isolate is selected from the group consisting of *Mycobacterium tuberculosis* Genebank Accession: H37Rv NC_000962.3; *Mycobacterium tuberculosis* str. Beijing/NITR203 Genebank Accession: NC_021054.1; *Mycobacterium tuberculosis* H37Ra Genebank Accession: NC_009525.1; *Mycobacterium tuberculosis* F11 Genebank Accession: NC_009565.1; *Mycobacterium tuberculosis* 7199-99 Genebank Accession: NC_020089.1; *Mycobacterium tuberculosis* str. Haarlem Genebank Accession: NC_022350.1; *Mycobacterium tuberculosis* CDC1551 Genebank Accession: NC_002755.2; *Mycobacterium tuberculosis* str. Erdman=ATCC 35801 NC_020559.1. In one embodiment the *Mycobacterium tuberculosis* is *Mycobacterium tuberculosis* Genebank Accession: H37Rv.

In one embodiment the *Mycobacterium tuberculosis* isolate is selected from the group consisting of *Mycobacterium tuberculosis* EAI5/NITR206 Genebank Accession: NC_021194.1; *Mycobacterium tuberculosis* PanR0802 Genebank Accession: NZ_CM002050.1; *Mycobacterium tuberculosis* H37Rv Genebank Accession: NC_000962.3; *Mycobacterium tuberculosis* KZN 1435 Genebank Accession: NC_012943.1; *Mycobacterium tuberculosis* SUMu002 Genebank Accession: NZ_ADHR00000000.1; *Mycobacterium tuberculosis* CCDC5079 Genebank Accession: NC_017523.1; *Mycobacterium tuberculosis* PanR0208 Genebank Accession: NZ_CM002055.1; *Mycobacterium tuberculosis* KZN V2475 Genebank Accession: NZ_CM000788.2; *Mycobacterium tuberculosis* HN878 Genebank Accession: NZ_CM001043.1; *Mycobacterium tuberculosis* H37RvCO Genebank Accession: NZ_CM001515.1; *Mycobacterium tuberculosis* SUMu001 Genebank Accession: NZ_ADHQ00000000.1; *Mycobacterium tuberculosis* S96-129 Genebank Accession: NZ_AEGB00000000.1; *Mycobacterium tuberculosis* PanR1005 Genebank Accession: NZ_CM002051.1; *Mycobacterium tuberculosis* PanR0407 Genebank Accession: NZ_ATEB00000000; *Mycobacterium tuberculosis* PanR0315 Genebank Accession: NZ_ATEJ00000000.1; and *Mycobacterium tuberculosis* NA-A0009 Genebank Accession: NZ_ALYH00000000.

Methods and systems of the invention are particularly useful for screening all members of the population for TB, i.e. including healthy individuals. TB infection is so prevalent that the whole population is suspected of having TB infection, e.g. latent infection showing no symptoms of the disease. The World Health Organization (WHO) estimates that between 1.5 and 2 billion people worldwide have latent TB upon, and e.g. upon entry into most school systems screening for *Mycobacterium tuberculosis* infection is a required test. The tests described herein can replace the standard PPD test that is currently used to mass screen for TB infection. The PPD test is a tuberculosis skin test used to determine if someone has developed an immune response to *Mycobacterium tuberculosis*, this response can occur if someone currently has TB, if they were exposed to it in the past, or if they received the BCG vaccine against TB (which is not commonly administered in the U.S.). The PPD test is commonly used to screen healthy adults and children, as billions of people worldwide have latent TB and show no signs of the infection, and around 2 to 3 million people worldwide die of TB each year. However, the PPD test has a disadvantage in that it will positively identify an uninfected subject as having a positive PPD test, if the subject has received a BCG vaccine. The methods, assays, and systems described herein will not falsely identify those that have received a BCG vaccine as being positive for TB, as such patients, unless they are truly infected with *Mycobacterium tuberculosis* will not show the presence of the compounds of Formula 1-IV which are specific for *Mycobacterium tuberculosis*. In addition a subject that has been administered the BCG vaccine will not show a positive reactive immune reaction against the compounds of Formula 1-IV, which are specific for *Mycobacterium tuberculosis*. In a related idea, serological tests for *M. tuberculosis* infection have not been widely implemented, and one key reason for this is that in endemic areas environmental bacteria are common, and exposure to environmental bacteria causes false positive tests for patient antibodies. Because the compounds (I-IV) are produced only by *M. tuberculosis* and the Rv3378c gene, which is required for their production, is absent in all known strains of environmental bacteria, serological tests based on compounds I-IV should not be hindered by this known mechanism of false positivity based on endemic environmental mycobacteria.

In certain embodiments, the subject to be tested for *Mycobacterium tuberculosis* (TB) infection is first selected as having one or more symptoms of TB infection. Symptoms of TB disease depend on where in the body the TB bacteria are growing. TB disease symptoms include, but are not limited to, a persistent cough that lasts 3 weeks or longer, pain in the chest, coughing up blood or sputum (phlegm from deep inside the lungs), weakness or fatigue, weight loss, no appetite, chills, fever, and sweating at night. One of skill in the art is well versed in assessing such symptoms.

In certain embodiments, the subject to be tested for *Mycobacterium tuberculosis* infection has previously been diagnosed as having a bacterial infection. Methods for diagnosing bacterial infection are well known to those of skill in the art and include, for example, complete blood count and cultures of fluid suspected of bacterial infection. This may include e.g., a blood culture, a urine culture, a spinal culture (which requires a spinal tap), or sputum culture. Another common method for determining bacterial infection is the Gram stain, which is a rapid, inexpensive method for demonstrating the presence of bacteria and fungi, as well as inflammatory cells using microscopy. These methods are further described in the following textbook: Kliegman: Nelson Textbook of Pediatrics, 19th ed. (2011) Saunders, an Imprint of Elsevier, Philadelphia U.S.A.; See Chapter 164: *Diagnostic Microbiology*, by Anita K. M. Zaidi and Donald A. Goldmann.

Methods, computer systems, media, and assays are provided herein for determining infection with *M. tuberculosis*. In embodiments of the invention, determination of infection with *M. tuberculosis* comprises determining the presence or absence of one or more compounds of Formula I-IV in a biological sample that has been taken from a subject. The presence of one or more compounds is indicative that the individual is infected with TB.

As used herein Formula I refers to 1-tuberculosinyladenosine (1-TbAd) having the following chemical structure:

1-tuberculosinyladenosine

As used herein Formula II refers to $N^6$-tuberculosinyladenosing ($N^6$-TbAd) having the following chemical structure:

N6-tuberculosinyladenosine

As used herein Formula III refers to a mycoloyl-tuberculosinyladenosine (Mucoloyl TbAd) having the following chemical structure:

(III)

wherein:

$R^1$ is H or $R^2$ is absent or provided that one of $R^2$ and $R^3$ is $R^3$ and $R^4$ are selected independently from hydrogen, mycolic acids, and any combinations thereof, provided that at least one of $R^3$ and $R^4$ is a mycolic acid.

In embodiments of compounds of Formula III, $R^1$ can be and $R^2$ can be absent. In some other embodiments, $R^1$ can be H and $R^2$ can be

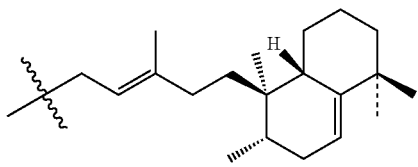

It is noted that when R² is

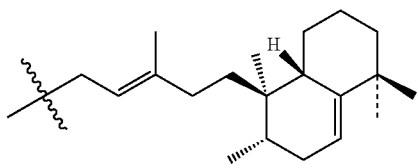

the nitrogen it is attached to carries a positive charge.

In compounds of Formula III, only one or both of R³ and R⁴ can be a mycolic acid. When R³ and R⁴ both are mycolic acids, they can be the same or different. In addition, they can be same type of mycolic acid. In some embodiments, one of R³ and R⁴ is hydrogen and the other is a mycolic acid. In one embodiment, R³ is hydrogen and R⁴ is a mycolic acid. In another embodiment, R³ is a mycolic acid and R⁴ is hydrogen.

Mycolic acids are very long chain (up to C95) α-branched and β-hydroxylated fatty acids (Laval et al. Anal Chem, 2001, 73: 4537-4544, content of which is incorporated herein by reference in its entirety). Mycolic acids can be described as a β-hydroxy acid substituted at the α-position with a moderately long aliphatic chain. Generally, mycolic acids are composed of a longer beta hydroxy chain with a shorter alpha-alkyl side chain. Mostly, mycolic acids contain between 30 and 90 carbon atoms. The exact number of carbons varies by species and can be used as an identification aid. Most mycolic acids also contain various functional groups. In some embodiments, mycolic acid is a mycolic acid produced by *Mycobacterium tuberculosis*. Exemplary mycolic acids include, but are not limited to, α-mycolic acids, α'-mycolic acids, methoxymycolic acids, ketomycolic acids, epoxymycolic acids.

Generally, α-mycolic acids are of structure: $CH_3-(CH_2)_n-A-(CH_2)_m-B-(CH_2)_p-CH(OH)-CH(CO_2H)-(CH_2)_q-CH_3$; α'-mycolic acids of structure: $CH_3-(CH_2)_n-A-CH=CH-(CH_2)_p-CH(OH)-CH(CO_2H)-(CH_2)_q-CH_3$; methoxymycolic acids of structure: $CH_3-(CH_2)_n-CH(CH_3)-CH(OCH_3)-(CH_2)_m-B-(CH_2)_p-CH(OH)-CH(CO_2H)-(CH_2)_q-CH_3$; ketomycolic acids of structure: $CH_3-(CH_2)_n-CH(CH_3)-C(O)-(CH_2)_m-B-(CH_2)_p-CH(OH)-CH(CO_2H)-(CH_2)_q-CH_3$; epoxymycolic acids of structure: $CH_3-(CH_2)_n-CH(CH_3)-X-(CH_2)_m-B-(CH_2)_p-CH(OH)-CH(CO_2H)-(CH_2)_q-CH_3$, wherein X is

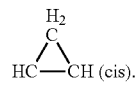

ω-carboxymycolic acids of structure: $HO-C(O)-(CH_2)_m-B-(CH_2)_p-CH(OH)-CH(CO_2H)-(CH_2)_q-CH_3$; and ω1-carboxymycolic acids of structure: $CH_3-CH(OCH_3)-(CH_2)_n-A-(CH_2)_m-B-(CH_2)_p-CH(OH)-CH(CO_2H)-(CH_2)_q-CH_3$, wherein A is CH=CH (cis or trans), CH(CH₃)-CH=CH (cis or trans), or

(cis or trans); B is CH=CH (cis or trans), CH=CH-CH(CH₃) (cis or trans),

(cis or trans), or

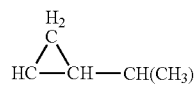

(cis or trans); n, m, p and q are independently 12, 13, 14, 15, 16, 17, 18, 19, 20, 21, 22, 23, 24, or 25.

Preferably, A is CH=CH (cis), CH(CH₃)-CH=CH (trans), or

Preferred B are CH=CH (cis), CH=CH-CH(CH₃) (trans),

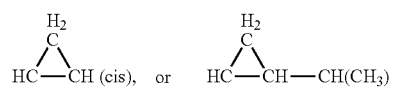

(trans).

In the above described structures of mycolic acids, n and p can be independently 13, 15, 17, 19, or 21. When no methyl branch is present in both A and B (i.e. A is CH=CH or

and B is CH=CH or

or a methyl branch is present in both A and B (i.e., A is CH(CH₃)-CH=CH and B is CH=CH-CH(CH₃) or

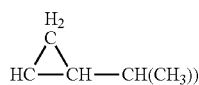

m can be 10, 12, 14, 16, or 18. When a methyl branch is present in either A or B, m can be 11, 13, 15, 17, or 19. Generally, q is 17, 19, 21, or 25.

In some embodiments, $R^3$ and $R^4$ are mycolic acids selected independently from the group consisting of α' mycolic acids (56 carbons), α' mycolic acids (58 carbons), α' mycolic acids (60 carbons), α' mycolic acids (62 carbons), α' mycolic acids (64 carbons), α' mycolic acids (66 carbons), α' mycolic acids (68 carbons), α mycolic acids (69 carbons), α mycolic acids (70 carbons), α mycolic acids (71 carbons), α mycolic acids (72 carbons), ω1-methoxy mycolic acids (71 carbons), α mycolic acids (73 carbons), keto mycolic acids (72 carbons), ω1-methoxy mycolic acids (72 carbons), ω1-methoxy mycolic acids (72 carbons), α mycolic acids (74 carbons), keto mycolic acids (73 carbons), ω1-methoxy mycolic acids (73 carbons), methoxy mycolic acids (73 carbons), ω1-methoxy mycolic acids (73 carbons), ω1-methoxy mycolic acids (73 carbons), α mycolic acids (75 carbons), keto mycolic acids (74 carbons), ω1-methoxy mycolic acids (74 carbons), methoxy mycolic acids (74 carbons), ω1-methoxy mycolic acids (74 carbons), α mycolic acids (76 carbons), keto mycolic acids (75 carbons), ω1-methoxy mycolic acids (75 carbons), methoxy mycolic acids (75 carbons), ω1-methoxy mycolic acids (75 carbons), ω1-methoxy mycolic acids (75 carbons), α mycolic acids (77 carbons), keto mycolic acids (76 carbons), ω1-methoxy mycolic acids (76 carbons), methoxy mycolic acids (76 carbons), ω1-methoxy mycolic acids (76 carbons), α mycolic acids (78 carbons), keto mycolic acids (77 carbons), ω1-methoxy mycolic acids (77 carbons), methoxy mycolic acids (77 carbons), ω1-methoxy mycolic acids (77 carbons), ω1-methoxy mycolic acids (77 carbons), α mycolic acids (79 carbons), keto mycolic acids (78 carbons), ω1-methoxy mycolic acids (78 carbons), methoxy mycolic acids (78 carbons), ω1-methoxy mycolic acids (78 carbons), α mycolic acids (80 carbons), keto mycolic acids (79 carbons), ω1-methoxy mycolic acids (79 carbons), methoxy mycolic acids (79 carbons), ω1-methoxy mycolic acids (79 carbons), α mycolic acids (81 carbons), keto mycolic acids (80 carbons), ω1-methoxy mycolic acids (80 carbons), methoxy mycolic acids (80 carbons), ω1-methoxy mycolic acids (81 carbons), α mycolic acids (82 carbons), keto mycolic acids (81 carbons), ω1-methoxy mycolic acids (81 carbons), methoxy mycolic acids (81 carbons), ω1-methoxy mycolic acids (82 carbons), α mycolic acids (83 carbons), keto mycolic acids (82 carbons), ω1-methoxy mycolic acids (82 carbons), methoxy mycolic acids (82 carbons), ω1-methoxy mycolic acids (83 carbons), ω1-methoxy mycolic acids (83 carbons), α mycolic acids (84 carbons), keto mycolic acids (83 carbons), ω1-methoxy mycolic acids (83 carbons), methoxy mycolic acids (83 carbons), ω1-methoxy mycolic acids (84 carbons), α mycolic acids (85 carbons), keto mycolic acids (84 carbons), ω1-methoxy mycolic acids (84 carbons), methoxy mycolic acids (84 carbons), ω1-methoxy mycolic acids (85 carbons), ω1-methoxy mycolic acids (85 carbons), α mycolic acids (86 carbons), keto mycolic acids (85 carbons), ω1-methoxy mycolic acids (85 carbons), methoxy mycolic acids (85 carbons), ω1-methoxy mycolic acids (86 carbons), α mycolic acids (87 carbons), keto mycolic acids (86 carbons), ω1-methoxy mycolic acids (86 carbons), methoxy mycolic acids (86 carbons), ω1-methoxy mycolic acids (87 carbons), ω1-methoxy mycolic acids (87 carbons), α mycolic acids (88 carbons), keto mycolic acids (87 carbons), ω1-methoxy mycolic acids (87 carbons), methoxy mycolic acids (87 carbons), ω1-methoxy mycolic acids (88 carbons), α mycolic acids (89 carbons), keto mycolic acids (88 carbons), ω1-methoxy mycolic acids (88 carbons), methoxy mycolic acids (88 carbons), ω1-methoxy mycolic acids (89 carbons), α mycolic acids (90 carbons), keto mycolic acids (89 carbons), ω1-methoxy mycolic acids (89 carbons), methoxy mycolic acids (89 carbons), α mycolic acids (91 carbons), keto mycolic acids (90 carbons), ω1-methoxy mycolic acids (90 carbons), methoxy mycolic acids (90 carbons), ω1-methoxy mycolic acids (91 carbons), methoxy mycolic acids (91 carbons), ω1-methoxy mycolic acids (92 carbons), and ω1-methoxy mycolic acids (93 carbons).

We have identified distinct variants of mycoloyl-tuberculosinyladenosine that are made by *Mycobacterium tuberculosis*, each of which are useful as markers of infection with the bacteria, e.g. the distinct variants are mycolates of either alpha, methoxy and keto forms.

Formula IV is merely a representative structure of one of the mycoloyl-tuberculosinyladenosines that are useful in the methods of the invention.

As used herein, Formula IV refers to a mycoloyl-tuberculosinyladenosine of Formula III having the following chemical structure:

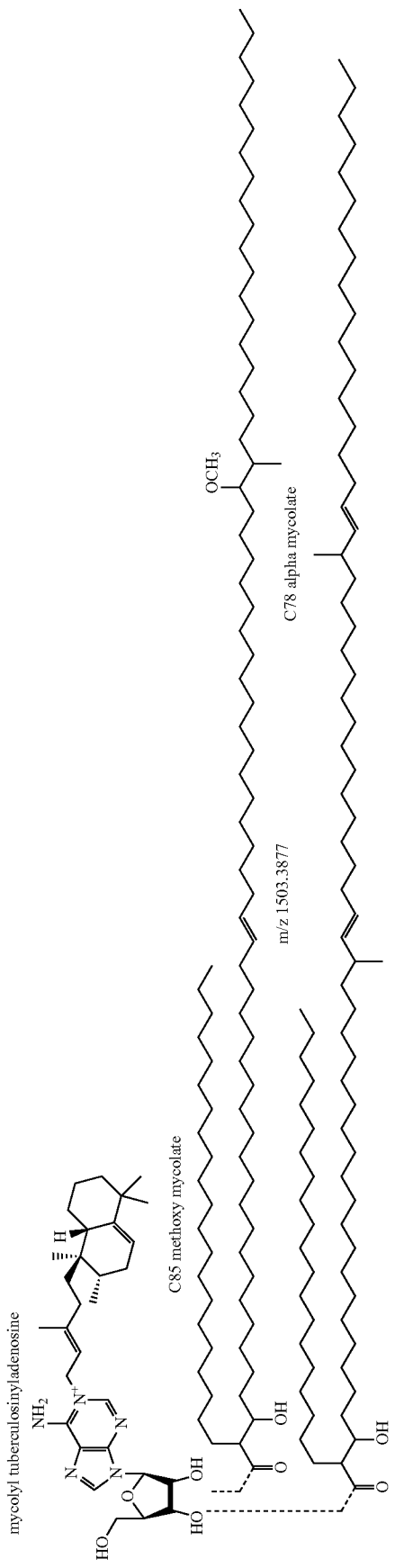

We have identified molecular variants of mycoloyl-tuberculosinyladenosine that are made by *Mycobacterium tuberculosis*, each of which are useful as markers of infection with the bacteria, See e.g. masses in Table 1. Mycolic acids produced by TB are described in e.g. C. Barry et al., (1998) Mycolic acids: structure biosynthesis and physiological functions, *Progress and Research* 37: 143, which is herein incorporated by reference in its entirety.

TABLE 1

| Alkyl length | Mycoloylated TbAd formula C | H | O | N | MW | M + H | M + Na |
|---|---|---|---|---|---|---|---|
| 53 | 83 | 145 | 8 | 5 | 1340.1093 | 1341.1166 | 1363.0385 |
| 56 | 86 | 153 | 6 | 5 | 1352.1821 | 1353.1893 | 1375.1113 |
| 54 | 84 | 147 | 8 | 5 | 1354.1249 | 1355.1322 | 1377.0542 |
| 55 | 85 | 149 | 8 | 5 | 1368.1406 | 1369.1479 | 1391.0698 |
| 58 | 88 | 157 | 6 | 5 | 1380.2134 | 1381.2206 | 1403.1426 |
| 56 | 86 | 151 | 8 | 5 | 1382.1562 | 1383.1635 | 1405.0855 |
| 57 | 87 | 153 | 8 | 5 | 1396.1719 | 1397.1792 | 1419.1011 |
| 60 | 90 | 161 | 6 | 5 | 1408.2447 | 1409.2519 | 1431.1739 |
| 58 | 88 | 155 | 8 | 5 | 1410.1875 | 1411.1948 | 1433.1168 |
| 59 | 89 | 157 | 8 | 5 | 1424.2032 | 1425.2105 | 1447.1324 |
| 62 | 92 | 165 | 6 | 5 | 1436.2760 | 1437.2832 | 1459.2052 |
| 60 | 90 | 159 | 8 | 5 | 1438.2188 | 1439.2261 | 1461.1481 |
| 61 | 91 | 161 | 8 | 5 | 1452.2345 | 1453.2418 | 1475.1637 |
| 64 | 94 | 169 | 6 | 5 | 1464.3073 | 1465.3145 | 1487.2365 |
| 62 | 92 | 163 | 8 | 5 | 1466.2501 | 1467.2574 | 1489.1794 |
| 63 | 93 | 165 | 8 | 5 | 1480.2658 | 1481.2731 | 1503.1950 |
| 66 | 96 | 173 | 6 | 5 | 1492.3386 | 1493.3458 | 1515.2678 |
| 64 | 94 | 167 | 8 | 5 | 1494.2814 | 1495.2887 | 1517.2107 |
| 65 | 95 | 169 | 8 | 5 | 1508.2971 | 1509.3044 | 1531.2263 |
| 68 | 98 | 177 | 6 | 5 | 1520.3699 | 1521.3771 | 1543.2991 |
| 66 | 96 | 171 | 8 | 5 | 1522.3127 | 1523.3200 | 1545.2420 |
| 69 | 99 | 177 | 6 | 5 | 1532.3699 | 1533.3771 | 1555.2991 |
| 67 | 97 | 173 | 8 | 5 | 1536.3284 | 1537.3357 | 1559.2576 |
| 70 | 100 | 179 | 6 | 5 | 1546.3855 | 1547.3928 | 1569.3147 |
| 68 | 98 | 175 | 8 | 5 | 1550.3440 | 1551.3513 | 1573.2733 |
| 71 | 101 | 181 | 6 | 5 | 1560.4012 | 1561.4084 | 1583.3304 |
| 69 | 99 | 177 | 8 | 5 | 1564.3597 | 1565.3670 | 1587.2889 |
| 72 | 102 | 183 | 6 | 5 | 1574.4168 | 1575.4241 | 1597.3460 |
| 71 | 101 | 189 | 7 | 5 | 1584.4587 | 1585.4660 | 1607.3879 |
| 73 | 103 | 185 | 6 | 5 | 1588.4325 | 1589.4397 | 1611.3617 |
| 72 | 102 | 183 | 7 | 5 | 1590.4117 | 1591.4190 | 1613.3410 |
| 72 | 102 | 183 | 7 | 5 | 1590.4117 | 1591.4190 | 1613.3410 |
| 72 | 102 | 191 | 7 | 5 | 1598.4743 | 1599.4816 | 1621.4036 |
| 74 | 104 | 187 | 6 | 5 | 1602.4481 | 1603.4554 | 1625.3773 |
| 73 | 103 | 185 | 7 | 5 | 1604.4274 | 1605.4347 | 1627.3566 |
| 73 | 103 | 185 | 7 | 5 | 1604.4274 | 1605.4347 | 1627.3566 |
| 73 | 103 | 185 | 7 | 5 | 1604.4274 | 1605.4347 | 1627.3566 |
| 73 | 103 | 187 | 7 | 5 | 1606.4430 | 1607.4503 | 1629.3723 |
| 73 | 103 | 191 | 7 | 5 | 1610.4743 | 1611.4816 | 1633.4036 |
| 73 | 103 | 193 | 7 | 5 | 1612.4900 | 1613.4973 | 1635.4192 |
| 75 | 105 | 189 | 6 | 5 | 1616.4638 | 1617.4710 | 1639.3930 |
| 74 | 104 | 187 | 7 | 5 | 1618.4430 | 1619.4503 | 1641.3723 |
| 74 | 104 | 187 | 7 | 5 | 1618.4430 | 1619.4503 | 1641.3723 |
| 74 | 104 | 187 | 7 | 5 | 1618.4430 | 1619.4503 | 1641.3723 |
| 74 | 104 | 189 | 7 | 5 | 1620.4587 | 1621.4660 | 1643.3879 |
| 74 | 104 | 193 | 7 | 5 | 1624.4900 | 1625.4973 | 1647.4192 |
| 76 | 106 | 191 | 6 | 5 | 1630.4794 | 1631.4867 | 1653.4086 |
| 75 | 105 | 189 | 7 | 5 | 1632.4587 | 1633.4660 | 1655.3879 |
| 75 | 105 | 189 | 7 | 5 | 1632.4587 | 1633.4660 | 1655.3879 |
| 75 | 105 | 189 | 7 | 5 | 1632.4587 | 1633.4660 | 1655.3879 |
| 75 | 105 | 191 | 7 | 5 | 1634.4743 | 1635.4816 | 1657.4036 |
| 75 | 105 | 193 | 7 | 5 | 1636.4900 | 1637.4973 | 1659.4192 |
| 75 | 105 | 195 | 7 | 5 | 1638.5056 | 1639.5129 | 1661.4349 |
| 77 | 107 | 193 | 6 | 5 | 1644.4951 | 1645.5023 | 1667.4243 |
| 76 | 106 | 191 | 7 | 5 | 1646.4743 | 1647.4816 | 1669.4036 |
| 76 | 106 | 191 | 7 | 5 | 1646.4743 | 1647.4816 | 1669.4036 |
| 76 | 106 | 191 | 7 | 5 | 1646.4743 | 1647.4816 | 1669.4036 |
| 76 | 106 | 193 | 7 | 5 | 1648.4900 | 1649.4973 | 1671.4192 |
| 76 | 106 | 195 | 7 | 5 | 1650.5056 | 1651.5129 | 1673.4349 |
| 78 | 108 | 195 | 6 | 5 | 1658.5107 | 1659.5180 | 1681.4399 |
| 77 | 107 | 193 | 7 | 5 | 1660.4900 | 1661.4973 | 1683.4192 |
| 77 | 107 | 193 | 7 | 5 | 1660.4900 | 1661.4973 | 1683.4192 |
| 77 | 107 | 193 | 7 | 5 | 1660.4900 | 1661.4973 | 1683.4192 |
| 77 | 107 | 195 | 7 | 5 | 1662.5056 | 1663.5129 | 1685.4349 |

TABLE 1-continued

| Alkyl length | Mycoloylated TbAd formula C | H | O | N | MW | M + H | M + Na |
|---|---|---|---|---|---|---|---|
| 77 | 107 | 195 | 7 | 5 | 1662.5056 | 1663.5129 | 1685.4349 |
| 77 | 107 | 197 | 7 | 5 | 1664.5213 | 1665.5286 | 1687.4505 |
| 79 | 109 | 197 | 6 | 5 | 1672.5264 | 1673.5336 | 1695.4556 |
| 78 | 108 | 195 | 7 | 5 | 1674.5056 | 1675.5129 | 1697.4349 |
| 78 | 108 | 195 | 7 | 5 | 1674.5056 | 1675.5129 | 1697.4349 |
| 78 | 108 | 195 | 7 | 5 | 1674.5056 | 1675.5129 | 1697.4349 |
| 78 | 108 | 197 | 7 | 5 | 1676.5213 | 1677.5286 | 1699.4505 |
| 78 | 108 | 197 | 7 | 5 | 1676.5213 | 1677.5286 | 1699.4505 |
| 80 | 110 | 199 | 6 | 5 | 1686.5420 | 1687.5493 | 1709.4712 |
| 79 | 109 | 197 | 7 | 5 | 1688.5213 | 1689.5286 | 1711.4505 |
| 79 | 109 | 197 | 7 | 5 | 1688.5213 | 1689.5286 | 1711.4505 |
| 79 | 109 | 197 | 7 | 5 | 1688.5213 | 1689.5286 | 1711.4505 |
| 79 | 109 | 199 | 7 | 5 | 1690.5369 | 1691.5442 | 1713.4662 |
| 79 | 109 | 199 | 7 | 5 | 1690.5369 | 1691.5442 | 1713.4662 |
| 81 | 111 | 201 | 6 | 5 | 1700.5577 | 1701.5649 | 1723.4869 |
| 80 | 110 | 199 | 7 | 5 | 1702.5369 | 1703.5442 | 1725.4662 |
| 80 | 110 | 199 | 7 | 5 | 1702.5369 | 1703.5442 | 1725.4662 |
| 80 | 110 | 199 | 7 | 5 | 1702.5369 | 1703.5442 | 1725.4662 |
| 80 | 110 | 201 | 7 | 5 | 1704.5526 | 1705.5599 | 1727.4818 |
| 81 | 111 | 199 | 7 | 5 | 1714.5369 | 1715.5442 | 1737.4662 |
| 82 | 112 | 203 | 6 | 5 | 1714.5733 | 1715.5806 | 1737.5025 |
| 81 | 111 | 201 | 7 | 5 | 1716.5526 | 1717.5599 | 1739.4818 |
| 81 | 111 | 201 | 7 | 5 | 1716.5526 | 1717.5599 | 1739.4818 |
| 81 | 111 | 201 | 7 | 5 | 1716.5526 | 1717.5599 | 1739.4818 |
| 81 | 111 | 203 | 7 | 5 | 1718.5682 | 1719.5755 | 1741.4975 |
| 82 | 112 | 201 | 7 | 5 | 1728.5526 | 1729.5599 | 1751.4818 |
| 83 | 113 | 205 | 6 | 5 | 1728.5890 | 1729.5962 | 1751.5182 |
| 82 | 112 | 203 | 7 | 5 | 1730.5682 | 1731.5755 | 1753.4975 |
| 82 | 112 | 203 | 7 | 5 | 1730.5682 | 1731.5755 | 1753.4975 |
| 82 | 112 | 203 | 7 | 5 | 1730.5682 | 1731.5755 | 1753.4975 |
| 82 | 112 | 205 | 7 | 5 | 1732.5839 | 1733.5912 | 1755.5131 |
| 83 | 113 | 201 | 7 | 5 | 1740.5526 | 1741.5599 | 1763.4818 |
| 83 | 113 | 203 | 7 | 5 | 1742.5682 | 1743.5755 | 1765.4975 |
| 84 | 114 | 207 | 6 | 5 | 1742.6046 | 1743.6119 | 1765.5338 |
| 83 | 113 | 205 | 7 | 5 | 1744.5839 | 1745.5912 | 1767.5131 |
| 83 | 113 | 205 | 7 | 5 | 1744.5839 | 1745.5912 | 1767.5131 |
| 83 | 113 | 205 | 7 | 5 | 1744.5839 | 1745.5912 | 1767.5131 |
| 83 | 113 | 207 | 7 | 5 | 1746.5995 | 1747.6068 | 1769.5288 |
| 84 | 114 | 203 | 7 | 5 | 1754.5682 | 1755.5755 | 1777.4975 |
| 85 | 115 | 209 | 6 | 5 | 1756.6203 | 1757.6275 | 1779.5495 |
| 84 | 114 | 207 | 7 | 5 | 1758.5995 | 1759.6068 | 1781.5288 |
| 84 | 114 | 207 | 7 | 5 | 1758.5995 | 1759.6068 | 1781.5288 |
| 84 | 114 | 207 | 7 | 5 | 1758.5995 | 1759.6068 | 1781.5288 |
| 84 | 114 | 209 | 7 | 5 | 1760.6152 | 1761.6225 | 1783.5444 |
| 85 | 115 | 203 | 7 | 5 | 1766.5682 | 1767.5755 | 1789.4975 |
| 85 | 115 | 205 | 7 | 5 | 1768.5839 | 1769.5912 | 1791.5131 |
| 86 | 116 | 211 | 6 | 5 | 1770.6359 | 1771.6432 | 1793.5651 |
| 85 | 115 | 209 | 7 | 5 | 1772.6152 | 1773.6225 | 1795.5444 |
| 85 | 115 | 209 | 7 | 5 | 1772.6152 | 1773.6225 | 1795.5444 |
| 85 | 115 | 209 | 7 | 5 | 1772.6152 | 1773.6225 | 1795.5444 |
| 85 | 115 | 211 | 7 | 5 | 1774.6308 | 1775.6381 | 1797.5601 |
| 86 | 116 | 205 | 7 | 5 | 1780.5839 | 1781.5912 | 1803.5131 |
| 87 | 117 | 213 | 6 | 5 | 1784.6516 | 1785.6588 | 1807.5808 |
| 86 | 116 | 211 | 7 | 5 | 1786.6308 | 1787.6381 | 1809.5601 |
| 86 | 116 | 211 | 7 | 5 | 1786.6308 | 1787.6381 | 1809.5601 |
| 86 | 116 | 211 | 7 | 5 | 1786.6308 | 1787.6381 | 1809.5601 |
| 86 | 116 | 213 | 7 | 5 | 1788.6465 | 1789.6538 | 1811.5757 |
| 87 | 117 | 205 | 7 | 5 | 1792.5839 | 1793.5912 | 1815.5131 |
| 87 | 117 | 207 | 7 | 5 | 1794.5995 | 1795.6068 | 1817.5288 |
| 88 | 118 | 215 | 6 | 5 | 1798.6672 | 1799.6745 | 1821.5964 |
| 87 | 117 | 213 | 7 | 5 | 1800.6465 | 1801.6538 | 1823.5757 |
| 87 | 117 | 213 | 7 | 5 | 1800.6465 | 1801.6538 | 1823.5757 |
| 87 | 117 | 213 | 7 | 5 | 1800.6465 | 1801.6538 | 1823.5757 |
| 87 | 117 | 215 | 7 | 5 | 1802.6621 | 1803.6694 | 1825.5914 |
| 88 | 118 | 207 | 7 | 5 | 1806.5995 | 1807.6068 | 1829.5288 |
| 89 | 119 | 217 | 6 | 5 | 1812.6829 | 1813.6901 | 1835.6121 |
| 88 | 118 | 215 | 7 | 5 | 1814.6621 | 1815.6694 | 1837.5914 |
| 88 | 118 | 215 | 7 | 5 | 1814.6621 | 1815.6694 | 1837.5914 |
| 88 | 118 | 215 | 7 | 5 | 1814.6621 | 1815.6694 | 1837.5914 |
| 88 | 118 | 217 | 7 | 5 | 1816.6778 | 1817.6851 | 1839.6070 |
| 89 | 119 | 209 | 7 | 5 | 1820.6152 | 1821.6225 | 1843.5444 |
| 90 | 120 | 219 | 6 | 5 | 1826.6985 | 1827.7058 | 1849.6277 |
| 89 | 119 | 217 | 7 | 5 | 1828.6778 | 1829.6851 | 1851.6070 |
| 89 | 119 | 217 | 7 | 5 | 1828.6778 | 1829.6851 | 1851.6070 |
| 89 | 119 | 217 | 7 | 5 | 1828.6778 | 1829.6851 | 1851.6070 |

TABLE 1-continued

| Alkyl length | Mycoloylated TbAd formula C | H | O | N | MW | M + H | M + Na |
|---|---|---|---|---|---|---|---|
| 89 | 119 | 219 | 7 | 5 | 1830.6934 | 1831.7007 | 1853.6227 |
| 91 | 121 | 221 | 6 | 5 | 1840.7142 | 1841.7214 | 1863.6434 |
| 90 | 120 | 219 | 7 | 5 | 1842.6934 | 1843.7007 | 1865.6227 |
| 90 | 120 | 219 | 7 | 5 | 1842.6934 | 1843.7007 | 1865.6227 |
| 90 | 120 | 219 | 7 | 5 | 1842.6934 | 1843.7007 | 1865.6227 |
| 90 | 120 | 221 | 7 | 5 | 1844.7091 | 1845.7164 | 1867.6383 |
| 91 | 121 | 221 | 7 | 5 | 1856.7091 | 1857.7164 | 1879.6383 |
| 91 | 121 | 221 | 7 | 5 | 1856.7091 | 1857.7164 | 1879.6383 |
| 91 | 121 | 223 | 7 | 5 | 1858.7247 | 1859.7320 | 1881.6540 |
| 92 | 122 | 223 | 7 | 5 | 1870.7247 | 1871.7320 | 1893.6540 |
| 93 | 123 | 225 | 7 | 5 | 1884.7404 | 1885.7477 | 1907.6696 |

In certain embodiments, the compounds of Formula I-IV further comprise an acetyl group and/or fatty acid group, and such compounds are detected as a measure of the subject having TB infection.

Biological Samples

In methods, systems, and assays of embodiments of the invention, the biological samples (test samples) are tested to determine the presence or absence of one or more compounds (i.e. the compounds of Formula I-IV) that are indicative of *M. tuberculosis* being present in the sample, and thus are indicative that the subject is infected with *M. tuberculosis*.

Any biological sample that is derived from a subject can be used in methods of the invention. In certain embodiments, the biological sample is selected from the group consisting of: breath, sputum, blood, urine, gastric lavage, and pleural fluid. The biological sample can also be a sample selected from the group consisting of: lung tissue, lymphoid tissue e.g. associated with the lung, paranasal sinuses, bronchi, a bronchiole, alveolus, ciliated mucosal epithelia of the respiratory tract, mucosal epithelia of the respiratory tract, squamous epithelial cells of the respiratory tract, a mast cell, a goblet cell, a pneumocyte (type 1 or type 2), broncheoalveolar lavage fluid (BAL), alveolar lining fluid, an intra epithelial dendritic cell, sputum, mucus, saliva, blood, serum, plasma, a peripheral blood mononuclear cell (PBMC), a neutrophil and a monocyte.

Samples can be collected as a solid, liquid, and/or as a gas form. Methods of sample collection are well known to those of skill in the art. In one embodiment, the biological sample is obtained from a subject by a method selected from the group consisting of surgery or other excision method, aspiration of a body fluid such as hypertonic saline or propylene glycol, broncheoalveolar lavage, bronchoscopy, saliva collection with a glass tube, salivette (Sarstedt A G, Seveln, Switzerland), Ora-sure (Epitope Technologies Pty Ltd, Melbourne, Victoria, Australia), omni-sal (Saliva Diagnostic Systems, Brooklyn, N.Y., USA), collection of gaseous material, and blood collection, e.g. by use of a syringe. Methods of collection of plasma are also described in Gershman, N. H. et al, *J Allergy Clin Immunol*, 10(4): 322-328, 1999.

In certain embodiments, the biological sample is treated to lyse the cells in the sample. Such methods include, e.g., the use of detergents, enzymes, repeatedly freezing and thawing said cells, sonication and/or vortexing the cells in the presence of glass beads, amongst others.

In another embodiment, the biological sample is treated to denature proteins or extract lipids. Methods of denaturing proteins are well known to those of skill in the art and include, e.g. heating a sample, treatment with 2-mercaptoethanol, or treatment with detergents and other compounds such as, for example, guanidinium or urea. In yet another embodiment, a biological sample is treated to concentrate a protein is said sample. Methods of concentrating proteins include precipitation, freeze drying, use of funnel tube gels (TerBush and Novick, *Journal of Biomolecular Techniques*, 10(3); 1999), ultrafiltration or dialysis. Methods of extracting lipids are well known to those of skill in the art and include, e.g. treating with chloroform, methanol and other organic solvents.

The sample can be analyzed directly for the one or more compounds (Formulas I-IV). Alternatively, the sample can be cultured in a suitable growth medium to allow growth and metabolism of bacteria in the sample. The bacteria in a sample may be grown in media or in culture. Samples can be cultured for any amount of time that allows for propagation of bacteria. For example, samples may be cultured for less than 2 hours, 2-4 hours, 4-6 hours, 6-10 hours, more than 10 hours or more than 24 hours. The culture may include any known bacterial culturing media, for example glucose, lipids, short-chain fatty acids, etc., such as propionate, cholesterol, and/or palmitate, or sodium propionate.

In certain embodiments, the methods of the invention, which determine the presence or absence of the compound/s of Formula I-IV in the biological samples, comprise the step of comparing the data of the biological sample obtained from the subject (i.e. the test sample) with a data from a reference sample. As one of skill in the art is aware, such comparison can remove background noise in any assay of determination.

In one embodiment, the reference sample is a biological sample of the same type from a subject that does not have *Mycobacterium tuberculosis* infection. The subject can be determined not to have infection using established *Mycobacterium tuberculosis* diagnostics, and confirmed by culturing. For example, sputum smears and cultures can be done for acid-fast bacilli by using fluorescence microscopy (auramine-rhodamine staining), which is more sensitive than conventional Ziehl-Neelsen staining (See e.g. Kumar, Vinay; et al. (2007) Robbins Basic Pathology (8th ed.) Saunders Elsevier. pp. 516-522; Burke and Parnell. Minimal Pulmonary Tuberculosis. 1948. 59:348 *Canadian Medical Association Journal*; and Steingart K, Henry M, Ng V, et al. (2006) "Fluorescence versus conventional sputum smear microscopy for tuberculosis: a systematic review". *Lancet Infect Dis* 6 (9): 570-81). In cases where there is no spontaneous sputum production, a sample can be induced, usually by nebulized inhalation of a saline or saline with bronchodilator solution. A comparative study found that inducing three sputum samples is more sensitive than three gastric washings (Brown M, Varia H, Bassett P, Davidson R N, Wall R, Pasvol G (2007). "Prospective study of sputum induction, gastric washing, and bronchoalveolar lavage for the diagnosis of pulmonary tuberculosis in patients who are unable to expectorate". *Clin Infect Dis* 44 (11): 1415-20).

In one embodiment of the invention, the reference sample and the test (or subject) sample are both processed, and assayed in the same manner. The data obtained for the reference sample and the test sample are then compared. In one embodiment, the reference sample and the test sample are processed, analyzed or assayed at the same time. In another embodiment, the reference sample and the test sample are processed, analyzed or assayed at a different times.

In an alternate embodiment, the reference sample is derived from an established data set that has been previously generated, also known as reference data. In one embodiment, the reference data is obtained from a single biological sample of the same type from a subject that does not have *Mycobacterium tuberculosis* infection. In one embodiment, the reference sample comprises data from a sample population study of individuals that do not have TB infection, such as, for example, statistically significant data of background ranges of compound data. Data derived from processing, analyzing or assaying the test sample is then compared to data obtained for the sample population that does not have *M. tuberculosis*. Reference data is obtained from a sufficiently large number of reference samples so as to be representative of a population and allows for the generation of a data set for determining the average level of any particular parameter.

As used herein, the term "statistically significant" or "significantly" refers to statistical significance and generally means a two standard deviation (2SD) or greater difference.

In certain aspects, methods are provided for determining if a subject is responsive to a treatment for *M. tuberculosis*. In such aspects, in some embodiments, the concentration of one or more compounds of Formula I-IV are determined from measuring the amount of the compound/s in a biological sample taken from a subject at a time point before treatment, and then are compared to data obtained from a biological sample from the same subject after treatment. Alternatively, a biological sample is taken at the time of treatment, and another thereafter a period of time, e.g. after two days, three days, for days, or more after treatment. A decrease in the amount of one or more compounds of Formula I-IV indicates that the treatment for TB infection is working to reduce the bacterial load of TB.

Detection of Compounds

There are many methods available to those of skill in the art for detection/measurement of the compounds described herein that are specific *M. tuberculosis*, (i.e. the compounds of Formula I-IV). Non-limiting examples include for example mass spectrometry (MS), nuclear magnetic resonance spectroscopy, and an immunoassay. For example, high performance liquid chromatography mass spectrometry (HPLC-MS) or collision induced mass spectrometry (CID-MS), MALDI/TOF (time-of-flight), SELDI/TOF, liquid chromatography-mass spectrometry (LC-MS), gas chromatography-mass spectrometry (GC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference. Mass spectrometry methods are well known in the art (see, e.g., Li et al. (2000) Tibtech 18:151-160; Rowley et al. (2000) *Methods* 20: 383-397; and Kuster and Mann (1998) *Curr. Opin. Structural Biol.* 8: 393-400; Chait et al., Science 262:89-92 (1993); Keough et al., *Proc. Natl. Acad. Sci. USA.* 96:7131-6 (1999); reviewed in Bergman, EXS 88:133-44 (2000)). For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.third ed. Vol. 15, John Wiley & Sons, New York 1995, pp. 1071-1094. Software programs such as the Biomarker Wizard program (Ciphergen Biosystems, Inc., Fremont, Calif.) can be used to aid in analyzing mass spectra, e.g., comparing the signal strength of peak values from spectra of a test subject sample and a control sample (e.g., a normal healthy person not having a compound of Formula I-IV, or in the alternative a positive control having the compound/s).

In one embodiment, liquid chromatography/mass spectrometry (LC/MS) is used for detection of bacterial compounds I-IV, for example, LC/MS data files can be processed with the MassHunter Qualitative Analysis Software version B.02.00 (Agilant technologies, Santa Clara, Calif.).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. In SELDI, the substrate surface is modified so that it is an active participant in the desorption process. In one variant, the surface is derivatized with adsorbent and/or capture reagents that selectively bind the compound of interest. In another variant, the surface is derivatized with energy absorbing molecules that are not desorbed when struck with the laser. In another variant, the surface is derivatized with molecules that bind the compound of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of one compounds of Formula I-IV will typically involve detection of signal intensity. This, in turn, can reflect the quantity. For example, in certain embodiments, the signal strength of peak values from spectra of a first sample and a second sample can be compared (e.g., visually, by computer analysis etc.), to determine the relative amounts of particular compounds. Software programs such as the Biomarker Wizard program (Ciphergen Biosystems, Inc., Fremont, Calif.) can be used to aid in analyzing mass spectra. The mass spectrometers and their techniques are well known to those of skill in the art. Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to mixed with the known control sample in the same mass spectrometry run.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio. In some embodiments the relative amounts of one or more compounds present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one embodiment, the presence of one or more compounds of Formula I-IV is detected by determining the presence of host antibodies directed against the compound/s, e.g. by an immunoassay. The compounds of Formula I-IV are not normally present in individuals that are not infected with *Mycobacterium tuberculosis*, thus the compounds are antigens, and antibodies that bind to these compounds are generated by the host.

In one embodiment, the immunoassay used is similar to the established PPD test for *Mycobacterium tuberculosis* (See e.g. Von Reyn CF1 et al. (2001) *Int J Tuberc Lung Disease* December; 5(12):1122-8.). The PPD tests for the presence of host antibodies against PPD. If the patient has TB they will exhibit a positive reaction to the injected PPD. In embodiments of the methods of the invention, the presence of host antibodies directed against one or more compounds of Formula I-IV can be similarly tested. For example, one or more compounds of Formula I-IV can be administered to a subject, e.g. injected under the first layer of skin. The subject can then be monitored for an immune reaction to the one or more compounds of Formula I-IV, wherein a positive immune reaction after 48 to 72 hours, indicates that the subject is infected with *Mycobacterium tuberculosis*. The positive immune reaction occurs because the compound/s were present before administration of the test (before injection of the compound/s), and the subject had already hosted an immune reaction against those compounds.

A common immunoassay is the "Enzyme-Linked Immunosorbent Assay (ELISA)." There are different forms of ELISA, which are well known to those skilled in the art. The standard techniques e.g. are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, *J. Clin. Chem. Clin. Biochem.*, 22:895-904.

In another aspect of the invention, an immunoassay, (e.g. an ELISA or other assay) is performed to measure the presence of one or more compounds of Formula I-IV, wherein an antibody that specifically binds to the compound/s is used to directly detect the compound in a biological sample from a subject. As a non-limiting example, an antibody that binds to a compound of Formula I-IV can be conjugated to a solid support to serve as a 'capture antibody' (e.g. tissue culture plate, a gel, a membrane, a column, or a bead) and a test biological sample incubated with the antibody conjugated to the solid support. A compound that has bound to the antibody can then be detected using a second antibody that specifically binds to the compound, optionally a labeled antibody (e.g. sandwich ELISA). Alternatively, the compound/s can be eluted from the capture antibody, and detected by other methods. For example, methods including but not limited to, HPLC or Mass Spectrometry.

In one embodiment, an ELISA is performed by coating one or more compounds of Formula I-IV on a tissue culture plate, coating the plate with a blocking agent, such as gelatin or BSA and then incubating the coated ELISA plate with the biological sample, e.g. blood plasma, or sera, for a sufficient time to allow host antibody to bind the compound/s. The presence of the bound host antibody is then detected. In one embodiment, the sample plates are then incubated with an anti-host antibody (e.g. anti-human antibody), which is optionally detectably labeled), and the bound antibody detected in an ELISA plate reader. Variants of the assay can be performed, for example by attaching one or more of the compounds of Formula I-IV on any solid support, e.g. beads, membrane, dipstick, or a column, rather than a tissue culture plate. The compounds can alternatively, be linked to the solid support using chemical linkers, such methods are known to those of skill in the art.

"Labeled antibody", as used herein, refers to antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In certain embodiments, a presence or amount of the *Mycobacterium tuberculosis* bacteria in the sample is identified based on the measured presence and/or concentration of one of the compounds of Formula I-IV detected in the sample. In certain embodiments, a presence or amount of *Mycobacterium tuberculosis* bacteria in a sample is determined based on the presence or concentration of two or more compounds detected in the sample. In certain embodiments, a presence or amount of *Mycobacterium tuberculosis* bacteria in a sample is determined based on the presence or concentration of three or more compounds detected in the sample. In certain embodiments, the presence and/or amount of the *Mycobacterium tuberculosis* bacteria in a sample is identified at various time points, for example following administration of a therapy, so that a change in bacterial burden can be measured and the efficacy of the therapy identified.

The concentration of a compound of Formula I-IV is proportional to the number of bacteria in a subject. Thus a subject is determined to be responsive to a therapeutic treatment, if the concentration of a compound of formula I0IV decreases by a statistically significant amount as compared to the concentration of the compound before treatment.

Treatment Regimes

In embodiments of the invention, when individuals are identified as having TB, i.e. identified as having one or more compounds of Formula I-IV, a specialized treatment regime designed for treatment of TB is indicated.

In certain embodiments, the methods further comprise administration of a TB therapeutic when the subject is identified as having TB. For example, positively identified individuals can be administered a therapeutically or prophylactically effective amount of one or more agents that inhibit the replication of *M. tuberculosis*, or that elicit an immune response against *M. tuberculosis*.

TB treatment regimes for latent TB infection include, but are not limited to, administration of one or more of the following TB therapeutics: isoniazid (INH), rifampin (RIF) and rifapentine (RPT). Subjects with active TB disease are treated by taking a combination of two or more of the following therapeutic drugs for 6 to 9 months: isoniazid (INH), ethambutol (EMB), and pyrazinamide (PZA), rifampin (RIF) and rifapentine (RPT). Regimens for treating TB disease usually have an initial phase of 2 months with one or more therapeutics, followed by a choice of combination phase of two or more therapeutics for either 4 or 7 months (total of 6 to 9 months for treatment). The combination therapy is done to prevent resistance.

TB therapeutics can be classified into 5 groups: Group 1 TB drugs are the first line of defense and include agents such as oral pyrazinamide, ethambutol, and rifabutin; Group 2 TB drugs are injectable and include agents such as kanamycin, amikacin, capreomycin, and streptomycin; Group 3 TB drugs include the fluoroquinolones such as levofloxacin, moxifloxacin, and ofloxacin; Group 4 TB drugs include the oral bacteriostatic second line of defense agents, such as paraaminosalicylic acid, cycloserineterizidone, thionamide, and protionamid; Group 5 TB drugs include agents with an unclear role in the treatment of drug resistant TB and include agents such as clofazimine, linezolidamoxicillin/clavulanate and thioacetazoneimipenem/cilas, as well as at high dose isoniazid, and clarithromycin.

TB therapeutic Isoniazid (Laniazid, Nydrazid), is also known as isonicotinylhydrazine, and is the first-line medication in prevention and treatment of tuberculosis (Hans L Riede (2009), Fourth-generation fluoroquinolones in tuberculosis, *Lancet* 373 (9670): 1148-1149). Isoniazid is manufactured from isonicotinic acid, which is produced from 4-methylpyridine. Isoniazid is available in tablet, syrup, and injectable forms (given intramuscularly or intravenously).

TB therapeutic rifampin is also known as rifaldazine, RMP, rofact (in Canada), and rifampin in the United States (Masters, Susan B.; et al. (2005), Katzung & Trevor's pharmacology, New York: Lange Medical Books/McGraw Hill, Medical Pub. Division). There are various types of rifamycins. The rifampicin form, with a 4-methyl-1-piperazinaminyl group, is the most clinically effective.

TB therapeutic Rifapentine was approved by the Food and Drug Administration (FDA) in June 1998. It is synthesized in one step from rifampicine (Sharma S K et al. (2013). Rifamycins (rifampicin, rifabutin and rifapentine) compared to isoniazid for preventing tuberculosis in HIV-negative people at risk of active TB, Cochrane Database of Systematic Reviews: 7).

TB therapeutic ethambutol is usually given in combination with other tuberculosis drugs, such as isoniazid, rifampicin and pyrazinamide (Yendapally R, Lee R E (2008). "Design, synthesis, and evaluation of novel ethambutol analogues". *Bioorg. Med. Chem. Lett.* 18 (5): 1607-11).

TB therapeutic pyrazinamide is used in combination with drugs such as isoniazid and rifampicin. Pyrazinamide is used in the first two months of treatment to reduce the duration of treatment required (Hong Kong Chest Service, Medical Research Council (1981) Controlled trial of four thrice weekly regimens and a daily regimen given for 6 months for pulmonary tuberculosis, *Lancet* 1(8213): 171-174). Regimens not containing pyrazinamide must be taken for nine months or more.

An example dosage regime of a therapeutic TB drug in adults includes, e.g. 5 mg/kg/day (max 300 mg daily of each therapeutic) for 6 months. Dosages may also be given intermittent. For example, for Isoniazid the Centers for Disease Control (CDC) recommends 15 mg/kg/day twice weekly (900 mg max dose), and the World Health Organization (WHO) recommends 10 mg/kg/day three times weekly (900 mg max dose) for either 6 or 9 months. When prescribed intermittently (twice or thrice weekly), the dose is 10-15 mg/kg (max 900 mg daily), depending on the regimen chosen. Patients with slow clearance of the drug (via acetylation as described above) may require reduced dosages to avoid toxicity. The recommended dosages of the TB therapeutics are well established, and known to those of skill in the art.

As used herein, the terms "treat" or "treatment" or "treating" refers to both therapeutic treatment and prophylactic (i.e. preventative) measures, wherein the object is to prevent or slow the development of virulent TB infection. Treatment is generally "effective" if one or more symptoms or clinical markers of TB are reduced. In one embodiment, "Treatment" includes curing of disease, however, in another embodiment, treatment does not include curing of disease. Treatment can prevent the onset of disease and reduce symptoms, e.g. such they are greatly reduced or such that they are not detectable. For example, treatment is "effective" if the bacterial concentration, is significantly reduced or an increase in growth prevented. Beneficial or desired clinical results include, but are not limited to, alleviation of one or more symptom(s) of TB, diminishment of extent of TB disease (i.e., not worsening), delay or slowing of TB growth, amelioration or palliation of disease state, and remission.

The term "effective amount" as used herein refers to the amount of a pharmaceutical composition, to decrease at least one or more symptoms of TB, and relates to a sufficient amount of pharmacological composition to provide the desired effect. The phrase "therapeutically effective amount" and "pharmaceutically effective amount" are used interchangeably and as used herein means a sufficient amount of the composition to treat TB at a reasonable benefit/risk ratio applicable to any medical treatment. The term "therapeutically effective amount" therefore refers to an amount of the composition that is sufficient to effect a therapeutically or prophylactically significant reduction in a symptom or clinical marker associated with TB.

In certain embodiments, a therapeutically effective amount reduces the number of bacteria in a subject (bacterial load). A therapeutically or prophylactically significant reduction in a symptom or reduction of bacterial load is, e.g. at least about 10%, at least about 20%, at least about 30%, at least about 40%, at least about 50%, at least about 60%, at least about 70%, at least about 80%, at least about 90% in a measured parameter as compared to a control (e.g. bacterial load and symptoms assessed in the subject before treatment). Measured or measurable parameters include clinically detectable markers of disease, for example, elevated or depressed levels of a biological marker such as TBAd compounds described herein (i.e. Formula I-IV), as well as parameters related to a clinically accepted scale of symptoms or markers for a disease or disorder. It should be understood, however, that the total daily usage of the compositions and formulations as disclosed herein will be decided by the attending physician within the scope of sound medical judgment. The exact amount required will vary depending on factors such as age, weight and severity of TB disease being treated.

The TB therapeutic may be administered by any suitable means. The compound suitable for treatment of TB may be contained in any appropriate amount in any pharmaceutically acceptable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., drops, tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions suitable for treatment of TB may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

The actual amount of the therapeutic compound/s administered will depend upon numerous factors such as the severity of TB infection to be treated, the age and relative health of the subject, the potency of the compound used, the route and form of administration, and other factors. Therapeutically effective amounts of therapeutic compounds may range from, for example, approximately 0.01-50 mg per kilogram body weight of the recipient per day; preferably about 0.1-20 mg/kg/day. Thus, as an example, for administration to a 70 kg person, the dosage range would most preferably be about 7 mg to 1.4 g per day. The choice of formulation depends on various factors such as the mode of drug administration (e.g., for oral administration, formulations in the form of tablets, pills, or capsules are preferred) and the bioavailability of the drug substance.

Pharmaceutical compositions are comprised of, in general, a therapeutic compound in combination with at least one pharmaceutically acceptable excipient. Acceptable excipients are non-toxic, aid administration, and do not adversely affect the therapeutic benefit of the therapeutic compound. Such excipients may be any solid, liquid, semi-solid or, in the case of an aerosol composition, gaseous excipient that is generally available to one skilled in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

Systems and Computer Readable Media

Embodiments of the invention also provide for systems (and computer readable media for causing computer systems) to perform a method for determining whether an individual has been infected with *Mycobacterium tuberculosis*.

A system for analyzing a biological sample is provided. The system comprises: a) a determination module configured to receive data form measuring a compound present in a biological sample of a subject suspected of having *Mycobacterium tuberculosis* infection, wherein the compound is selected from the group consisting of a compound of Formula I, Formula II and Formula III, and to optionally determine the concentration of the compound; b) a storage device configured to store information from the determination module; c) a comparison module adapted to compare the data stored on the storage device with reference data, and to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection; and d) a display module for displaying a content based in part on the comparison result for the user, wherein the content is a signal indicative that the subject has *Mycobacterium tuberculosis* infection in the presence of at least one compound of step c), or a signal indicative that the subject lacks *Mycobacterium tuberculosis* infection in the absence of each of the compounds of Formula I, Formula II and Formula III. In certain embodiments, the compound of Formula III is represented by Formula IV.

In one embodiment of the system, in step d) the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c).

In another embodiment of the system, in step d) the content is a signal indicative that the subject has *Mycobacterium tuberculosis* infection in the presence of at least three single compounds of step c).

In still another embodiment of the system, the content further comprises a signal indicating that the subject should be treated for *Mycobacterium tuberculosis* in the presence of at least one compound selected from the group consisting of Formula I, Formula II, and Formula III.

The invention further provides for a computer readable medium having computer readable instructions recorded thereon to define software modules including a comparison module and a display module for implementing a method on a computer. The method comprising: a) comparing with the comparison module the data stored on a storage device with reference data to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection, and b) displaying a content based in part on the comparison result for the user, wherein the content is a signal indicative of that the subject has *Mycobacterium tuberculosis* infection in the presence of at least one compound of step a), or a signal indicative that the subject lacks *Mycobacterium tuberculosis* infection in the absence of each of the compounds of Formula I, Formula II and Formula III.

In one embodiment of the computer readable medium, in step b) of the method the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c).

In one embodiment of the computer readable medium, in step b) of the method the content is a signal indicative that the subject has *Mycobacterium tuberculosis* infection in the presence of at least three single compounds of step a).

In certain embodiments of the computer readable medium, the compound of Formula III is represented by Formula IV.

In one embodiment of the computer readable medium, in step b) of the method, wherein the content further comprises a signal indicating that the subject should be treated for *Mycobacterium tuberculosis* in the presence of at least one compound selected from the group consisting of Formula I, Formula II, Formula III and Formula IV.

Embodiments of the invention have been described through functional modules, which are defined by computer executable instructions recorded on computer readable media and which cause a computer to perform method steps when executed, See FIG. 12 and FIG. 13. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and nonvolatile memory, and any other tangible medium which can be used to store the desired information and which can accessed by a computer including and any suitable combination of the foregoing.

Computer-readable data embodied on one or more computer-readable media, or computer readable medium 200, may define instructions, for example, as part of one or more programs, that, as a result of being executed by a computer, instruct the computer to perform one or more of the functions described herein (e.g., in relation to system 10, or computer readable medium 200), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 10, or computer readable medium 200 described herein, may be distributed across one or more of such components, and may be in transition there between.

The computer-readable media may be transportable such that the instructions stored thereon can be loaded onto any computer resource to implement the aspects of the present invention discussed herein. In addition, it should be appreciated that the instructions stored on the computer readable media, or computer-readable medium 200, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The functional modules of certain embodiments of the invention include a determination module, a storage device, a comparison module and a display module See FIG. 12 and FIG. 13. The functional modules can be executed on one, or multiple, computers, or by using one, or multiple, computer networks. The determination module 40 has computer executable instructions to provide compound information in computer readable form. As used herein, "compound information" refers to data representative of the presence or absence of one or more compounds of Formula I-IV, e.g. this can include but is not limited to data from a mass spectrometer, NMR, or fluorescence meter, e.g. an ELISA plate reader etc. For non-limiting examples, compound information can be presented as ion chromatograms, or e.g. as a positive or negative fluorescent signal (e.g. from an ELISA, or other assay) indicating the presence or absence of the compound respectively. Moreover, information "related to" the compound can include information that includes detection of the presence or absence of particular mycolic acids, determination of the concentration of the compound in the sample (e.g., as a measure of bacterial load), and the like.

As an example, determination modules 40 for determining compound information may include known systems for automated analysis mass spectrometry data including but not limited to software options available from AB SCIEX, Framingham, Mass. such as: Analyst® which is software that automates MS to MS/MS acquisition with Information-Dependent Acquisition (IDA) mode, the Scheduled MRM™ Algorithm uses overlapping MRM monitoring periods to maximize quantitative performance and accuracy; BioPharmaView™; Cliquid®, a software for routine screening and quantitation provides a simple, four-step workflow for LC/MS/MS analysis and bi-directional LIMS compatibility with any LIMS or LIS; DiscoveryQuant™ a software that improves the speed of analysis and information gathering, an optimized model performs a rapid, single-injection compound optimization on every compound using a unique MRM-based approach and then populates a database with this information; LightSight®, a software for metabolite identification; LipidView™, a software that streamlines the molecular characterization and quantification of lipid species from electrospray MS data; MarkerView™ a software for metabolomics and biomarker profiling across multiple samples; MetabolitePilot™ a software for TripleTOF® systems which streamlines the detection and identification of metabolites; MultiQuant™ a software that processes MRM data for quantitative information with a comprehensive user interface for superior data visualization; SignalFinder™ Integration Algorithm, which allows more reliable integration and less user intervention and extends the dynamic range functionality; and PeakView® software, which offers a qualitative review of LC/MS and MS/MS data for the TripleTOF® Systems. In certain embodiments, information gathering involves a fluorescent readout, non-limiting examples of software that can be used include, e.g. Molecular Dynamics FluorImager™ 575, SI Fluorescent Scanners, and Molecular Dynamics FluorImager™ 595 Fluorescent Scanners (all available from Amersham Biosciences UK Limited, Little Chalfont, Buckinghamshire, England).

Other methods for determining compound information, i.e. determination modules 40, include but are not limited to, systems for Matrix Assisted Laser Desorption Ionization-Time of Flight (MALDI-TOF) systems and SELDI-TOF-MS; automated ELISA systems (e.g., DSX® or DS2® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The compound information determined in the determination module can be read by the storage device 30. As used herein the "storage device" 30 is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices 30 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 30 is adapted or configured for having recorded thereon compound information or concentration level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device 30. Those skilled in the art can readily adopt any of the presently known methods for recording information on known media to generate manufactures comprising the compound information or concentration level information.

A variety of software programs and formats can be used to store the compound information or concentration level information on the storage device. Any number of data processor structuring formats (e.g., text file or database) can be employed to obtain or create a medium having recorded thereon the compound information or concentration level information.

By providing compound information in computer-readable form, one can use the information in readable form in the comparison module 80 to compare a specific data profile with the reference data within the storage device 30. For example, search programs can be used to identify fragments or regions of the peaks that match a particular compound of Formula I-IV (reference data, e.g., compound information obtained from a control sample, such as mass spec data, etc. of synthesized compound, or mass spec data of a reference sample). The comparison made in computer-readable form provides a computer readable comparison result which can be processed by a variety of means, e.g. using the software describe herein. Content 140 based on the comparison result can be retrieved from the comparison module 80 to indicate infection with *Mycobacterium tuberculosis*; e.g. if one or more compounds is present, then infection is indicated.

In one embodiment the reference data stored in the storage device 30 to be read by the comparison module 80 is compound information data obtained from a control biological sample of the same type as the biological sample to be tested. Alternatively, the reference data are data from a population of samples. In one embodiment the reference data are compound data from the assay used for detection, and the data are indicative of TB, i.e. the data show the presence of one or more compounds of Formula I-IV. Alternatively, the reference data can be representative of data found in non-infected individuals and thus, is indicative that one in not infected with TB bacteria.

The "comparison module" 80 can use a variety of available software programs and formats for the comparison operative to compare compound information determined in the determination module 40 to reference data. In one embodiment, the comparison module 80 is configured to use pattern recognition techniques to compare compound information from one or more entries to one or more reference data patterns. The comparison module 80 may be configured using existing commercially-available or freely-available software for comparing patterns, and may be optimized for particular data comparisons that are conducted. The comparison module 80 provides computer readable information related to the compound information that can include, for example, detection of the presence or absence of particular mycolic acids, information regarding compound concentration, e.g. determined by peak height or intensity of signal, e.g. from a fluorescence.

In one embodiment, the comparison module 80 uses compound information alignment programs such as Lipid-View™, or PeakView® software, which offers a qualitative review of LC/MS and MS/MS data.

The comparison module 80, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executable will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the comparison module 80 performs comparisons with mass-spectrometry spectra, for example comparisons of peak information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Concentration profiles can be discerned.

In one embodiment of the invention, pattern comparison software is used to determine whether patterns of expression or mutations are indicative of a disease.

The comparison module 80 provides computer readable comparison result that can be processed in computer readable form by predefined criteria, or criteria defined by a user, to provide a content based in part on the comparison result that may be stored and output as requested by a user using a display module 110. The display module 110 enables display of a content 140 based in part on the comparison result for the user, wherein the content 140 is a signal indicative of TB infection. Such signal, can be for example, a display of content 140 indicative of the presence or absence of a compound of Formula I-IV indicating the presence or absence of TB infection on a computer monitor, or a printed page of content 140 indicating the presence or absence of TB infection from a printer, or a light or sound indicative of the presence or absence of TB infection.

The content 140 based on the comparison result may include an data profile of one or more compounds. In one embodiment, the content 140 based on the comparison includes a molecular signature of a particular compound. In one embodiment, the content 140 based on the comparison result is merely a signal indicative of the presence or absence of infection with TB bacterium (TB infection).

In one embodiment of the invention, the content 140 based on the comparison result is displayed a on a computer monitor. In one embodiment of the invention, the content 140 based on the comparison result is displayed through printable media. The display module 110 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content 140 based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the compound information, e.g., display of an indication of the presence or absence of one or more of the compounds of Formula I-IV. In one embodiment, the compound information of the reference sample data is also displayed.

In one embodiment, the display module 110 displays the comparison result data and whether the comparison result is indicative of a disease, e.g., the data indicates the presence of one or more compounds of Formula I-IV.

In one embodiment, the content 140 based on the comparison result that is displayed is a signal (e.g. positive or negative signal) indicative of the presence or absence of TB infection, thus only a positive or negative indication may be displayed.

Embodiments of the present invention therefore provide for systems 10 (and computer readable medium 200 for causing computer systems) to perform methods for determining whether an individual has *Mycobacterium tuberculosis* infection based on data of the compounds of Formula-I-IV, compound information.

System 10, and computer readable medium 200, are merely an illustrative embodiments of the invention for performing methods of determining whether an individual has a specific disease or disorder or a pre-disposition, for a specific disease or disorder based on compound information or concentration level of the compound/s, and is not intended to limit the scope of the invention. Variations of system 10, and computer readable medium 200, are possible and are intended to fall within the scope of the invention.

The modules of the machine, or used in the computer readable medium, may assume numerous configurations. For example, function may be provided on a single machine or distributed over multiple machines Kits Another aspect of the invention provides a kit for detecting *M. tuberculosis* infection in a biological sample. In one embodiment, the kit comprises: (i) one or more compounds of Formula I-IV (i.e. the antigen) attached to a solid support, (e.g. a membrane, an ELISA plate or column beads); (ii) an agent that detects the formation of an antigen-antibody complex, e.g. an anti-human antibody, optionally detectably labeled, and iii) the kit optionally contains one or more antibodies that bind to a compound of Formula I-IV as a positive control antibody. Optionally, the kit further comprises compounds/reagents for detection of a labeled antibody, e.g. for detection of a labeled anti-human antibody. In yet another embodiment, a kit may additionally comprise a reference sample. Such a reference sample may for example, be a protein sample derived from a biological sample isolated from one or more tuberculosis subjects. Alternatively, a reference sample may comprise a biological sample isolated from one or more normal healthy individuals not infected with *Mycobacterium tuberculosis*. Such a reference sample is optionally included in a kit for a diagnostic or prognostic assay.

Definitions

All patents, patent applications, and publications identified herein are expressly incorporated herein by reference in their entirety, e.g. for the purpose of describing and disclosing the methodologies described in such publications.

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

A "normal" or "healthy individual", or "control group" refers to individuals that do not have infection with *Mycobacterium tuberculosis* who are preferably of similar age and race.

As used herein the terms, "individual", "subject", "patient", are used interchangeably and are intended to include humans and mammals.

Embodiments of the invention are further described in the following numbered paragraphs.

Paragraph 1, A method of identifying *Mycobacterium tuberculosis* in a subject comprising: measuring the presence or absence of at least one compound selected from the group consisting of a compound of Formula I (1-tuberculosinyladenosie), Formula II (6-tuberculosinyladenosine) and Formula III (a generic mycoloyl tuberculosinyladenosine), in a biological sample that is derived from a subject suspected of having *Mycobacterium tuberculosis* infection; wherein the presence of the at least one compound of step a) is indicative that the subject has *Mycobacterium tuberculosis* infection.

Paragraph 2, The method of paragraph 1, wherein the presence of the at least two compounds of step a) is indicative that the subject has *Mycobacterium tuberculosis* infection.

Paragraph 3, The method of paragraph 1, wherein the presence of the at least three compounds of step a) is indicative that the subject has *Mycobacterium tuberculosis* infection.

Paragraph 4, The method of any of paragraphs 1-3, further comprising administering to the subject a treatment for *Mycobacterium tuberculosis*.

Paragraph 5, A method for treatment of *Mycobacterium tuberculosis* comprising: administering a pharmaceutically effective amount of a *Mycobacterium tuberculosis* therapeutic to a subject that has the presence of at least one compound selected from the group consisting of a compound of Formula I, Formula II and Formula III.

Paragraph 6, The method of paragraph 5, wherein the pharmaceutically effective amount of a *Mycobacterium tuberculosis* therapeutic is administered to a subject that has presence of at least two compounds selected from the group consisting of a compound of Formula I, Formula II and Formula III.

Paragraph 7, The method of paragraph 5, wherein the pharmaceutically effective amount of a *Mycobacterium tuberculosis* therapeutic is administered to a subject that has presence of a compound of Formula I, Formula II and of Formula III.

Paragraph 8, A method for determining if a subject is responsive to a *Mycobacterium tuberculosis* treatment comprising: measuring the concentration of at least one compound selected from the group consisting of a compound of Formula I, Formula II and Formula III, in a first sample from a subject; administering to the subject a treatment for *Mycobacterium tuberculosis*; and measuring the concentration of the one or more compounds of step a) in a second sample from the subject, wherein a decrease in concentration of the compound as compared to the concentration in the first sample is indicative that the subject is responding the treatment for *Mycobacterium tuberculosis* and reducing infection.

Paragraph 9, The method of any of paragraphs 1-8, wherein the compound is a variant of the compound of Formula III represented by Formula IV (i.e. mycoloyl tuberculosinyladenosine as provided having R groups of C85 methoxy mycolate and C78 alpha mycolate).

Paragraph 10, The method of any of paragraphs 1-9, wherein the subject suspected of having *Mycobacterium tuberculosis* infection has been diagnosed as having a bacterial infection.

Paragraph 11, The method of any of paragraphs 1-10, wherein the subject is human.

Paragraph 12, The method of any of paragraphs 1-11, wherein the biological sample derived from the subject is selected from the group consisting of: breath, sputum, blood, urine, gastric lavage and pleural fluid.

Paragraph 13, The method of any of paragraphs 1-12, wherein the presence of the compound is measured using an assay selected from the group consisting of: mass spectrometry (MS), nuclear magnetic resonance spectroscopy and an immunoassay. (e.g. high performance liquid chromatography mass spectrometry (HPLC-MS or collision induced mass spectrometry (CID-MS)-Immunoassay to detect antibodies against 1-TbAd using—ELISA, coat).

Paragraph 14, The method of paragraph 13, wherein the assay is an immunoassay that detects the presence of the compound/s by monitoring the presence of host antibodies directed against the compound/s. (e.g. ELISA)

Paragraph 15, The method of paragraph 13, wherein the assay is an immunoassay that uses a non-host antibody that specifically binds to a compound of Formula I-IV (e.g. a capture antibody).

Paragraph 16, A system for analyzing a biological sample comprising: a determination module configured to receive data form measuring a compound present in a biological sample of a subject suspected of having *Mycobacterium tuberculosis* infection, wherein the compound is selected from the group consisting of a compound of Formula I, Formula II and Formula III, and to optionally determine the concentration of the compound; a storage device configured to store information from the determination module; a comparison module adapted to compare the data stored on the storage device with reference data, and to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection; and a display module for displaying a content based in part on the comparison result for the user, wherein the content is a signal indicative that the subject has *Mycobacterium tuberculosis* infection in the presence of at least one compound of step c), or a signal indicative that the subject lacks *Mycobacterium tuberculosis* infection in the absence of each of the compounds of Formula I, Formula II and Formula III.

Paragraph 17, The system of paragraph 16, wherein in step d) the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c).

Paragraph 18, The system of paragraph 16, wherein in step d) the content is a signal indicative that the subject has *Mycobacterium tuberculosis* infection in the presence of at least three single compounds of step c).

Paragraph 19, The system of any of paragraphs 16-18, wherein the content further comprises a signal indicating that the subject should be treated for *Mycobacterium tuberculosis* in the presence of at least one compound selected from the group consisting of Formula I, Formula II, and Formula III.

Paragraph 20, The system of any of paragraphs 16-19, wherein the compound of Formula III is represented by Formula IV.

Paragraph 21, The system of any of paragraphs 16-20, wherein the determination module is configured to receive data from a Mass Spectrometer.

Paragraph 22, The system of any of paragraphs 16-21, wherein the subject suspected of having *Mycobacterium tuberculosis* infection has been diagnosed as having a bacterial infection.

Paragraph 23, The system of any of paragraphs 16-22, wherein the subject is human.

Paragraph 24, The system of any of paragraphs 16-23, wherein the biological sample derived from the subject is selected from the group consisting of: breath, sputum, blood, urine, gastric lavage and pleural fluid.

Paragraph 25, The system of any of paragraphs 16-24, wherein the determination module receives data from a mass spectrometer, nuclear magnetic resonance spectroscopy, high performance liquid chromatography, or an immunoassay (e.g. data from an ELISA plate reader).

Paragraph 26, A computer readable medium having computer readable instructions recorded thereon to define software modules including a comparison module and a display module for implementing a method on a computer, said method comprising: comparing with the comparison module the data stored on a storage device with reference data to provide a comparison result, wherein the comparison result identifies the presence or absence of at least one compound selected from the group consisting of a compound of Formula I, Formula II, and Formula III; and wherein the presence of the at least one compound is indicative that the subject has *Mycobacterium tuberculosis* infection, and displaying a content based in part on the comparison result for the user, wherein the content is a signal indicative of that the subject has *Mycobacterium tuberculosis* infection in the presence of at least one compound of step a), or a signal indicative that the subject lacks *Mycobacterium tuberculosis* infection in the absence of each of the compounds of Formula I, Formula II and Formula III.

Paragraph 27, The computer readable medium of paragraph 26, wherein in step b) the content is a signal indicative that the subject has *Mycobacterium tuberculosis* infection in the presence of at least two compounds of step c), or a signal indicative that the subject lacks *Mycobacterium tuberculosis* infection in the absence of at least two of the compounds of step c).

Paragraph 28, The computer readable medium of paragraph 26, wherein in step b) the content is a signal indicative that the subject has *Mycobacterium tuberculosis* infection in the presence of at least three single compounds of step c).

Paragraph 29, The computer readable medium of any of paragraphs 26-28, wherein the compound of Formula III is represented by Formula IV.

Paragraph 30, The computer readable medium of any of paragraphs 26-29, wherein the content further comprises a signal indicating that the subject should be treated for *Mycobacterium tuberculosis* in the presence of at least one compound selected from the group consisting of Formula I, Formula II, Formula III and Formula IV.

Example 1: Identification of Tuberculosinyl Nucleotide Products of the Virulence Associated Enzyme Rv3378c Methods.

Bacterial Culture.

Mycobacteria were cultured in triplicate in Tween-free Middlebrook 7H9 broth supplemented with 10% Oleic acid Albumin Dextrose Catalase (Becton Dickinson) in 50 mL polystyrene tubes (Corning) shaking at 100 rpm at 37° C., and a fourth culture was treated with TWEEN to disperse bacteria just before taking the OD600 measurement. Cultures were harvested when the TWEEN culture replicate reached a 0.6 OD (+/−0.1). Stationary phase cultures of mycobacteria were cultured similarly but harvested at an OD of 2. Acid stressed cultures were grown in 4.5 pH citrate buffer.

Bacteria were cultured and extracted by chlorofolin/methanol mixtures or ethyl acetate, respectively, as described (4, 37). Lipid extracts were analyzed using an Agilent 6520 Accurate-Mass Q-Tof and a 1200 series HPLC system with a Varian Monochrom diol column (4, 37) with data output from XCMS and MultiplotPreprocess and Multiplot modules of GenePattern (Broad Institute) (38). Rv3378c and GroES/GroEL chaperones were coexpressed in BL21-CodonPlus™ (Stratagene) cells and purified on a Ni-NTA HisTrap™ FF column (GE Healthcare). Purified Rv3378c (10 mg/mL) was crystallized by vapor diffusion and 2.20-Å resolution data were collected on the Advanced Light Source (ALS). The structure of Rv3378c was solved by SAD phasing of a mercury derivative using Phenix AutoSol. Enzymatic assays were performed by incubating fifty-six micrograms of diterpene in presence of thirty-three mg of adenosine (Sigma) and eighty mg of purified Rv3378c in 1 mL of pH 7.4 Tris-HCl buffer 4 hr at 37° C. under magnetic agitation. *M. tuberculosis* transposon mutants from a random library (25) were grown in 96 well format, heat killed, followed by lipid extraction by 70:30 methanol:isopropanol. Lipids were analyzed by HPLC-MS to monitor 1-TbAd production. 1-TbAd null strains were confirmed regrowing the bacteria and using a full lipidomic analysis method. TbAd was purified from mycobacterial cell-associated lipid extract using normal and reversed phase chromatography. Structures were solved using CID-MS and NMR spectroscopy using a Bruker Avance 800

Mycobacterial Lipid Extraction.

HPLC-MS grade solvents (Fisher) and clean borosilicate glassware (Fisher), amber vials (Supelco) and Teflon-lined caps (Fisher) were used. Bacterial cultures were centrifuged (4,000 rpm, 10 min) to clarify culture supernatants, which were passed twice through a 0.22 µm filter to remove intact membrane fragments (1). Cell pellets were washed twice in 10 mL Optima water, resuspended in 1 mL of CH3OH, transferred to a 50 mL amber glass bottle and contacted with 25 mL CHCl3/CH3OH (2:1, v:v) overnight to sterilize bacteria. CHCl3/CH3OH suspensions were transferred in 50 mL conical glass tubes and rotated at 20° C. for at least 1 hr. After centrifugation, lipid extracts were decanted, and bacteria pellets subjected to 2 additional extractions using CHCl3:CH3OH (1:1, v:v) and CHCl3:CH3OH (1:2, v:v) with pooling of extracts and evaporation with GeneVac EZ-2 (SP Scientific) using the low boiling point mixture setting. Dried lipids were resuspended in CHCl3:CH3OH (1:1, v:v) and dried under nitrogen in preweighed vials and then reweighed in triplicate on microbalance (Mettler Toledo, XP205). Then extracts were redissolved in CHCl3:CH3OH (1:1, v:v) at 1 mg/mL.

HPLC-ESI-QT of Based Lipidomics.

Using an Agilent Technologies 6520 Accurate-Mass Q-Tof and a 1200 series HPLC system with a Varian Monochrom diol column (3 µm×150 mm×2 mm) and a Varian Monochrom diol guard column (3 µm×4.6 mm), normal phase lipidomics was carried out as described (2). Total lipid extracts were resuspended at 0.5 mg/mL in solvent A (hexanes:isopropanol, 70:30 [v:v], 0.02% [m/v] formic acid, 0.01% [m/v] ammonium hydroxide), filtered or centrifuged at 1,500 rpm for 5 min to remove trace non-lipidic materials prior to transfer to a glass autosampler vial (Agilent). Ten µg of lipid was injected, and the column (20° C.) was eluted at 0.15 ml/min with a binary gradient from 0% to 100% solvent B (isopropanol:methanol, 70:30 [v/v], 0.02% [m/v] formic acid, 0.01% [m/v] ammonium hydroxide): 0-10 min, 0% B; 17-22 min, 50% B; 30-35 min, 100% B; 40-44 min, 0% B, followed by additional 6 min 0% B postrun. Raw data files were converted to mzData using MassHunter and processed in R using the XCMS (version 1.24)(3) centWave peak finder (4). XCMS (http://metlin-.scripps.edu/xcms/index.php) deconvoluted and aligned across samples using s/n threshold of 5, a maximum tolerated m/z deviation of 10 ppm, a frame width of mzdiff=0.001, a peak width of 20-120 s and a band width of 5.

Comparative Lipidomics.

XCMS data matrices listing detected features, median m/z and median RT of triplicate lipidic extracts was imported into GenePattern (Broad Institute) using MultiplotPreprocess and Multiplot modules (5).

Protein expression and purification. Rv3378c and GroES/GroEL chaperones were coexpressed in BL21-CodonPlus™ (Stratagene) cells. Cell cultures were grown at 37° C. until OD600 reached ~0.6 and induced with 0.2 mM isopropyl β-D-thiogalactopyranoside (IPTG) and 0.2% (w/v) L-arabinose at 22° C. overnight. Cells were lysed by sonication and lysate was purified on a Ni-NTA HisTrap™ FF column (GE Healthcare). Partially purified Rv3378c was cleaved with thrombin at 4° C. overnight, loaded onto the Ni-NTA column, and flow-through fractions were concentrated and purified by gel filtration on a Superdex™ 75 (GE Healthcare).

Rv3378c Enzymatic Assays.

Fifty-six micrograms of dried TbPP or GGPP were resuspended in 1 mL of pH 7.4 Tris-HCl buffer (1 mM MgCl2, 0.1% Triton X-100 (w/v)) by sonication. Thirty-three µg of adenosine (Sigma) prepared at 1 mg/mL in pH 7.4 Tris-HCl buffer (33 µL) and 51 µL of recombinant Rv3378c at 16 mg/mL were added to the lipid solution and incubated 4 hr at 37° C. under magnetic agitation. Lipid products were extracted three times from the reaction mixture using chloroform (3×0.5 mL), pooled, dried and analyzed by HPLC-MS as described above. The detection of 1-TbAd was confirmed based on m/z mass accuracy, retention time and MS/MS experiments (30 eV).

Cloning Rv3378c Gene from M. tuberculosis.

The Rv3378c gene (GenBank™ accession number: CAA15763.1) was amplified by PCR from M. tuberculosis H37Rv genomic DNA using PfuTurbo DNA polymerase (Stratagene), introducing flanking NdeI and XhoI restriction sites. Amplified and digested PCR products were ligated in predigested pET-28b vector (Novagen), resulting an N-terminal cleavable hexahistidine tag followed by the protein coding sequence. Clones were verified by DNA sequencing (Elim Biopharm).

Transposon Mutant Library Screening.

Transposon mutants from a random library (50) were grown in 96 well format in Middlebrook 7H9 media to confluence and heat killed, followed by extraction with 100 µL of 70:30 methanol:isopropanol and shaking for 5 minutes. 100 µL aliquot was transferred to a Millipore 96 well filter plate and centrifuged at 4500 rpm for 10 minutes. The collected filtrate was used for rapid HPLC-MS analysis using an isocratic gradient of 70:30 methanol:isopropanol for three minutes. 1-TbAd production was monitored in MS positive mode spectra at 540.35 m/z and in MS/MS positive mode spectra by the detection of the adenine fragment at 136.06 m/z. Mutants negative for these ions were recorded as potential 1-TbAd null strains, which were confirmed using a full lipidomic analysis.

Rv3377c-Rv3378c Knock-in M. smegmatis Strain or Complementation of M. tuberculosis.

Wild-type M. smegmatis or TbAd deficient M. tuberculosis strains were transformed with a plasmid that episomally expresses Rv3377c-Rv3378c genes under the control of a tetracycline inducible promoter (pTETGW) (6).

Rv3378c and GroES/GroEL Proteins Expression and Purification.

The Rv3378c gene (GenBank™ accession number: CAA15763.1) was amplified by PCR from M. tuberculosis H37Rv genomic DNA using PfuTurbo DNA polymerase (Stratagene) and cloned into pET-28b vector (Novagen). Rv3378c mutants were generated using the QuikChange method (Stratagene). All clones were verified by DNA sequencing (Elim Biopharm).

Rv3378c and GroES/GroEL chaperones were coexpressed in BL21-Codon Plus™ (Stratagene) cells to improve the solubility of Rv3378c. Cell cultures were grown at 37° C. until OD600 reached ~0.6 and induced with 0.2 mM isopropyl β-D thiogalactopyranoside (IPTG) and 0.2% (w/v) L-arabinose at 22° C. overnight. Cells were harvested by centrifugation (4,500 rpm, 20 min), resuspended in 20 mM Hepes, pH 7.5, 500 mM NaCl, 0.5 mM TCEP, and 25 mM imidazole with EDTA free protease inhibitor cocktail (Roche). Resuspended cells were lysed by sonication and centrifuged (16,000 rpm, 90 min). Cleared lysate was purified on a Ni-NTA HisTrap™ FF column (GE Healthcare) with gradient elution using buffer containing 300 mM imidazole. Partially purified Rv3378c fractions were cleaved with thrombin at 4° C. overnight, loaded onto the Ni-NTA column, and flow-through fractions were concentrated and purified by gel filtration on a Superdex™ 75 (GE Healthcare) column equilibrated in 20 mM Hepes, pH 7.5, 50 mM NaCl, 0.5 mM TCEP, 10% glycerol.

Crystallographic Structure Determination of Rv3378c.

Purified Rv3378c (10 mg/mL) was crystallized by vapor diffusion from 100 mM citrate, pH 3.5, 10-15% (w/v) polyethylene glycol 3350. A cluster of crystals was separated by gentle mechanical prodding with a cat whisker. The resulting single crystals were transferred to mother liquor containing 25% ethylene glycol and directly plunged into liquid nitrogen prior to data collection. X-ray diffraction data were collected at 100 K on the Advanced Light Source (ALS) beamline 8.3.1 and processed using HKL2000 (7). The 2.20-Å resolution native data set and 2.30-Å resolution ethylmercury phosphate derivative data set were collected at wavelengths of 1.1111 and 1.0083 Å, respectively. Different crystal forms were observed by additional screening with Silver Bullets HT kit (Hampton Research), and a 2.36 Å resolution data set was collected at 1.1111 Å at 100 K on ALS beamline 8.3.1. The structure of Rv3378c was solved by SAD phasing of a mercury derivative using Phenix AutoSol (8). Initial models built by Phenix AutoBuild (8) were improved using ARP/warp (9), followed by manual building in Coot (10). The native structures were solved by molecular replacement using the mercury-derivatized structure as a search model in Phaser (11). Structures were refined using Phenix Refine (8), with exclusion of 10% of the reflections to calculate Rfree. Models were validated using Molprobity (12). Secondary structures were assigned using DSSP (Dictionary of Protein Secondary Structure) (13) and structural figures were generated using PyMOL (http://www.pymol.org/) (14).

Purification of 1-Tuberculosinyladenosine (Substance A).

Gram quantities of *M. tuberculosis* H37Rv and H37Ra were extracted three times with chloroform and methanol solution as described above. 500 mg of lipid extract was concentrated under nitrogen, and the lipid slurry was loaded on an open silica gel column (2 cm×1.6 cm) using chloroform. Fractions were eluted with the following sequence of solvents: chloroform, 95:5 chloroform/isopropanol, 95:5, 90:10 and 50:50 chloroform/methanol (v/v) with ion monitoring (m/z 540.5) to track substance A, which eluted in the 95:5 (v/v) chloroform/methanol and the 50:50 chloroform/methanol fractions. After drying, reversed phase HPLC (Waters Corporation) purification of pooled fractions enriched for the target ion was carried out using octadecyl-modified silica (5 micron) semi-preparative column (Higgins Analytical HAISIL C18, 250×10 mm). Using an isocratic 450:50:1 methanol/water/trifluoroacetic acid (v/v/v) gradient with a flow rate of 3.0 mL/min substance A appeared at 8 min. After drying with nitrogen and a 5-fold excess of acetonitrile HPLC chromatography was repeated giving pure 1-TbAd as assessed by MS and NMR spectroscopy.

METHODS REFERENCES

References

1. Madigan C A, et al. (2012) Lipidomic discovery of deoxysiderophores reveals a revised mycobactin biosynthesis pathway in *Mycobacterium tuberculosis*. *Proc Natl Acad Sci USA* 109(4):1257-1262.
2. Layre E, et al. (2011) A comparative lipidomics platform for chemotaxonomic analysis of *Mycobacterium tuberculosis*. *Chem Biol* 18(12):1537-1549.
3. Smith C A, Want E J, O'Maille G, Abagyan R, & Siuzdak G (2006) XCMS: processing mass spectrometry data for metabolite profiling using nonlinear peak alignment, matching, and identification. *Anal Chem* 78(3):779-787.
4. Tautenhahn R, Bottcher C, & Neumann S (2008) Highly sensitive feature detection for high resolution LC/MS. *BMC Bioinformatics* 9:504.
5. Reich M, et al. (2006) GenePattern 2.0. *Nat Genet* 38(5):500-501.
6. Sassetti C M, Boyd D H, & Rubin E J (2001) Comprehensive identification of conditionally essential genes in mycobacteria. *Proc Natl Acad Sci USA* 98(22):12712-12717.
7. Otwinowski W & Minor W (1997) Processing of X-ray diffraction data collected in oscillation mode. *Methods in Enzymology*, eds Charles W & Carter J (Academic Press), Vol 276, pp 307-326.
8. Adams P D, et al. (2010) PHENIX: a comprehensive Python-based system for macromolecular structure solution. *Acta Crystallogr D Biol Crystallogr* 66(Pt 2):213-221.
9. Langer G, Cohen S X, Lamzin V S, & Perrakis A (2008) Automated macromolecular model building for X-ray crystallography using ARP/wARP version 7. *Nat Protoc* 3(7):1171-1179.
10. Emsley P & Cowtan K (2004) Coot: model-building tools for molecular graphics. *Acta Crystallogr D Biol Crystallogr* 60(Pt 12 Pt 1):2126-2132.
11. McCoy A J, et al. (2007) Phaser crystallographic software. *J Appl Crystallogr* 40(Pt 4):658-674.
12. Chen V B, et al. (2010) MolProbity: all-atom structure validation for macromolecular crystallography. *Acta Crystallogr D Biol Crystallogr* 66(Pt 1):12-21.
13. Kabsch W & Sander C (1983) Dictionary of protein secondary structure: pattern recognition of hydrogen-bonded and geometrical features. *Biopolymers* 22(12):2577-2637.
14. Anonymous (The PyMOL Molecular Graphics System, Version 1.5.0.5, Shrodinger, LLC.
15. Maugel N, Mann F M, Hillwig M L, Peters R J, & Snider B B (2010) Synthesis of (+/−)-nosyberkol (isotuberculosinol, revised structure of edaxadiene) and (+/−)-tuberculosinol. *Org Lett* 12(11):2626-2629.
16. Davisson V J, et al. (1986) Org. Chem. (51):4768.

Experiments

To identify lipids with roles in tuberculosis disease, we systematically compared the lipid content of virulent *Mycobacterium tuberculosis* with the attenuated vaccine strain *M. bovis* BCG. Comparative lipidomics analysis identified more than 1,000 molecular differences, including a previously unknown, *M. tuberculosis*-specific lipid that is composed of a diterpene unit linked to adenosine. We established the complete structure of the natural product as 1-tuberculosinyladenosine (1-TbAd) using mass spectrometry and nuclear magnetic resonance (NMR) spectroscopy. A screen for 1-TbAd mutants, complementation studies and gene transfer identified Rv3378c as necessary for 1-TbAd biosynthesis. Whereas Rv3378c was previously thought to function as a phosphatase, these studies establish its role as a tuberculosinyl transferase and describe a new biosynthetic pathway for the sequential action of Rv3377c-Rv3378c. Ruling in this model, recombinant Rv3378c protein produced 1-TbAd, and its crystal structure revealed a cis-prenyl transferase fold with hydrophobic residues for isoprenol binding and a second binding pocket suitable for the nucleoside substrate. The dual-substrate pocket distinguishes Rv3378c from classical cis-prenyl transferases, providing a new model for the prenylation of diverse metabolites. Terpene nucleosides are rare in nature and 1-TbAd is known only in *M. tuberculosis*. Thus, this intersection of nucleoside and terpene pathways likely arose late in the evolution of the *M. tuberculosis* complex. 1-TbAd serves as an abundant chemical marker of *M. tuberculosis*, and the extracellular export of this amphipathic molecule likely accounts for the known virulence-promoting effects of the cytosolic Rv3378c enzyme.

Introduction

*Mycobacterium tuberculosis* remains one of the world's most important pathogens, with a mortality rate exceeding 1.5 million deaths annually (1). *M. tuberculosis* succeeds as a pathogen due to productive infection of the endosomal network of phagocytes. Its residence within the phagosome protects it from immune responses during its decades long infection cycle. However, intracellular survival depends on active inhibition of pH-dependent killing mechanisms, which occurs for *M. tuberculosis*, but not species with low disease-causing potential (2). Intracellular survival is also enhanced by an unusually hydrophobic and multi-layered protective cell envelope. Despite study of this pathogen for more than a century, the spectrum of natural lipids within *M. tuberculosis* membranes is not yet fully defined. For example, the products of many genes annotated as lipid synthases remain unknown (3), and mass spectrometry detects hundreds of ions that do not correspond to known lipids in the MycoMass and LipidDB databases (4, 5).

To broadly compare the lipid profiles of virulent and avirulent mycobacteria, we took advantage of a recently validated metabolomics platform (4). This high performance liquid chromatography-mass spectrometry (HPLC-MS) system uses methods of extraction, chromatography and databases that are specialized for mycobacteria. After extraction of total bacterial lipids into organic solvents, HPLC-MS enables massively parallel detection of thousands of ions corresponding to diverse lipids that range from apolar polyketides to polar phosphoglycolipids. Software-based (XCMS) ion finding algorithms report reproducibly detected ions as molecular features. Each feature is a 3-dimensional data point with linked mass, retention time and intensity values from one detected molecule or isotope. All features with equivalent mass and retention time from two bacterial lipid extracts are aligned, allowing pairwise comparisons of MS signal intensity to enumerate molecules that are overproduced in one strain with a false positive rate below 1 percent (4).

This comparative lipidomics system allowed an unbiased, organism-wide analysis of lipids from *M. tuberculosis* and the attenuated vaccine strain, *Mycobacterium bovis* Bacille Calmette Guerin (BCG). BCG was chosen because of its worldwide use as a vaccine and its genetic similarity to *M. tuberculosis* (6). We reasoned that any features that are specifically detected in *M. tuberculosis* might be clinically useful as markers to distinguish tuberculosis-causing bacteria from vaccines. Further, given the differing potential for productive infection by the two strains, any *M. tuberculosis*-specific compounds would be candidate virulence factors. Comparative genomics of *M. tuberculosis* and BCG successfully identified "regions of deletion" (RD) that encode genes that were subsequently proven to promote productive *M. tuberculosis* infection (7), including ESX-1 (8, 9). We reasoned that a metabolite-based screen might identify new virulence factors because not all functions of RD genes are known. Also, biologically important metabolites could emerge from complex biosynthetic pathways that cannot be predicted from single gene analysis.

Comparison of *M. tuberculosis* and BCG lipid profiles revealed more than 1,000 differences, among which we identified a previously unknown. *M. tuberculosis*-specific diterpene-linked adenosine and showed that it is produced by the enzyme Rv3378c. Previously, Rv3378c was thought to generate free tuberculosinols (10-12). This discovery revises the enzymatic function of Rv3378c, which acts as a virulence factor to inhibit phagolysosome fusion (13). Whereas current models of prenyl transferase function emphasize iterative lengthening of prenyl pyrophosphates using one binding pocket, the crystal structure of Rv3378c identifies two pockets in the catalytic site, establishing a mechanism for heterologous prenyl transfer to non-prenyl metabolites.

Results

Comparative Lipidomics of *M. Tuberculosis* and BCG

Using HPLC-MS for comparative analysis of lipid extracts of *M. tuberculosis* H37Rv and BCG (Pasteur strain), we detected 7,852 molecular features (FIG. 1, and data not shown). By aligning datasets and seeking features that significantly differed in intensity (corrected p-value <0.05), we identified 1,845 features that were overexpressed in one bacterium or the other (FIG. 1A). Among these features, we focused on molecules selectively expressed in *M. tuberculosis* that showed the highest fold-change ratios and intensity. We identified four molecular features corresponding to a singly charged molecular ion at m/z 540.357 ($C_{30}H_{45}N_5O_4$) and its isotopes (FIG. 1A), but this chemical formula did not match entries in the MycoMass (4) or other public databases. We named the unknown molecule substance A.

Substance A is an Abundant Natural Product of *M. Tuberculosis*

Figures 1B, 1C:
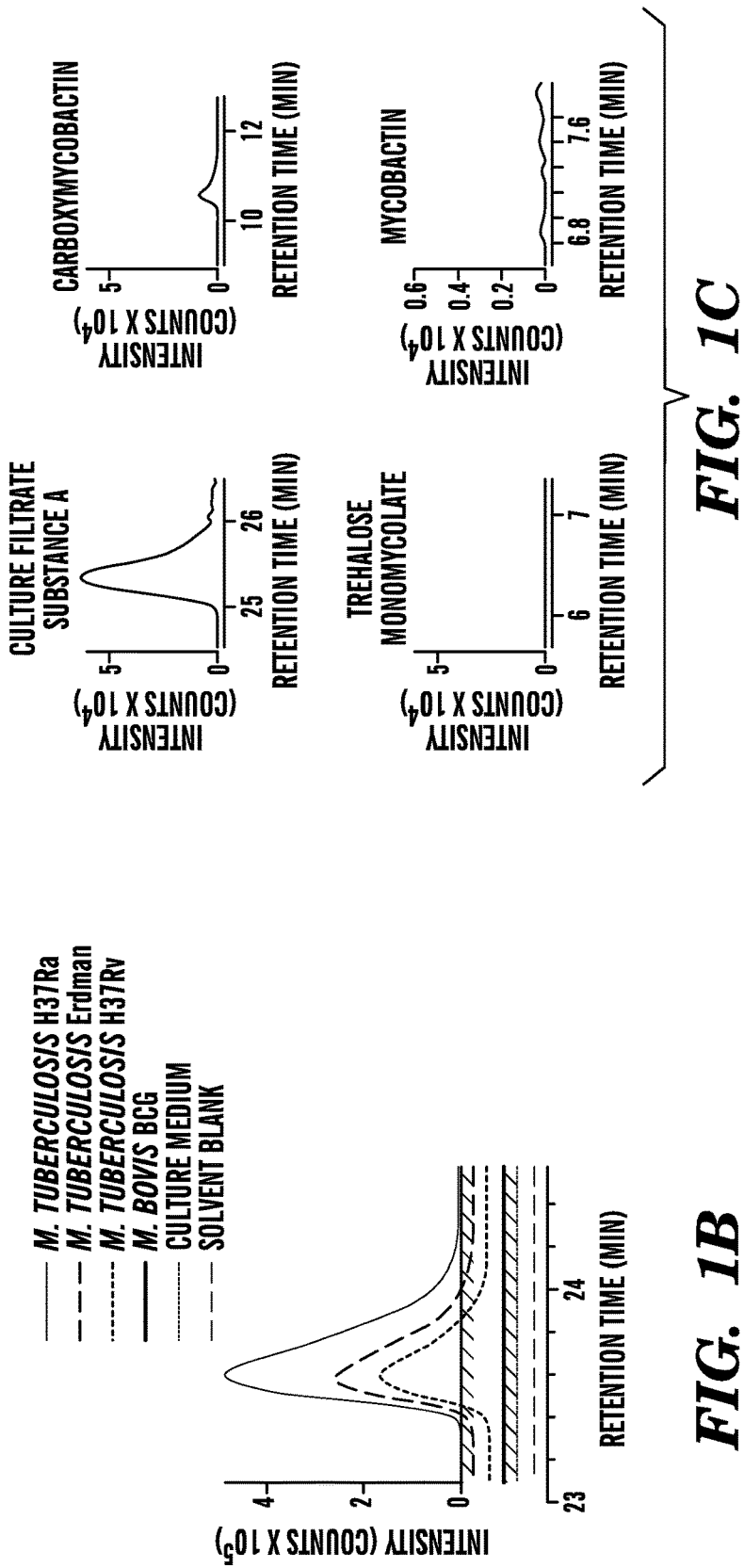

The molecular ion of substance A was one of the most intense ions in the *M. tuberculosis* lipidome (FIG. 1A), suggesting that it was produced in abundance. Identification of an apparently abundant molecule in a widely studied pathogen was unexpected, leading to questions about whether substance A was truly a natural product. However, this compound was absent in media, solvent blanks and BCG lipid extracts, but was reproducibly detected in three reference strains of *M. tuberculosis* (FIG. 1B). As observed with cell-associated compounds (FIG. 1A), culture filtrate (FIG. 1C) yielded bright ions, whose intensity was higher than that of the abundantly secreted siderophore, carboxymycobactin. Its release into the extracellular space likely results from trans-membrane transport, rather than budding of intact cell wall fragments, as cell wall-embedded lipids, trehalose monomycolate and mycobactin, were not detected in filtered supernatants (FIG. 1C). We detected substance A in *M. tuberculosis* during exponential or stationary phase and several types of media, or when subject to acid stress (FIG. 8A and FIG. 8B). Thus, substance A is a natural product, which is constitutively produced in many conditions and accumulates within and outside *M. tuberculosis*.

*M. tuberculosis* often compartmentalizes lipid biosynthesis so that lipids are assembled after transport across the plasma membrane. Sulfoglycolipids and phthiocerol dimycocerosates become undetectable when MmpL transporters are interrupted, even when biosynthetic genes are intact (14-16). Because ESX-1 is a transport system lacking in BCG, lack of export of an ESX-1 dependent lipid synthase might account for the loss of substance A. However, ESX-1 deficient *M. tuberculosis* lacking either the espA gene (Rv3616c) or the entire RD1 locus (17), which are both necessary for ESX-1 function, produces substance A at normal levels (FIG. 8C). After ruling out a major known specifies-specific difference in transport, we devised a screen to detect biosynthesis genes responsible for substance A.

Substance A is a 1-Tuberculosinyladenosine

Figure 2:
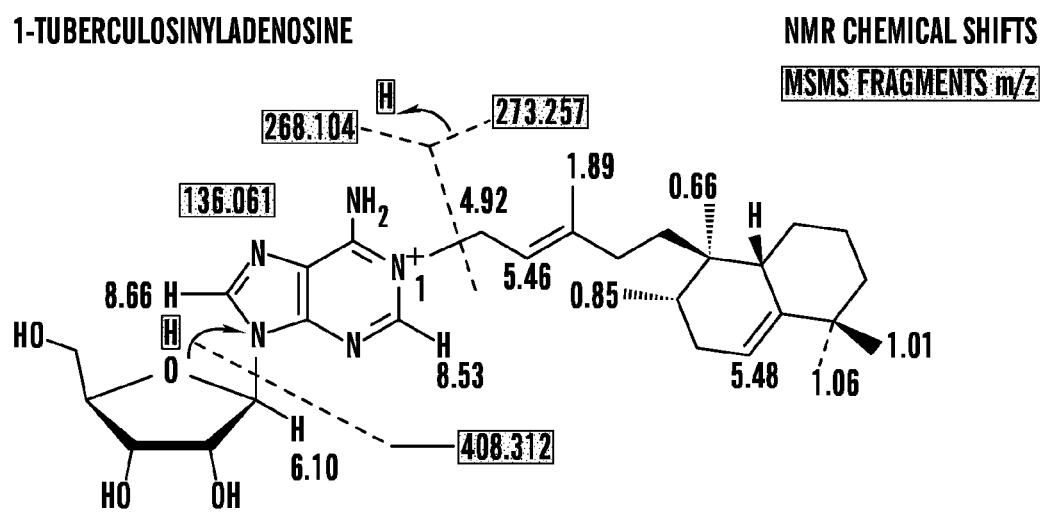
FIG. 2 shows the chemical structure of 1-tuberculosinyladenosine. Substance A was purified from *M. tuberculosis* lipid extracts was characterized using CID-MS and NMR (800 MHz) analyses yielding key collision products and resonances as indicated. These data establish that substance A is 1-tuberculosinyladenosine (1-TbAd).
Figure 14:
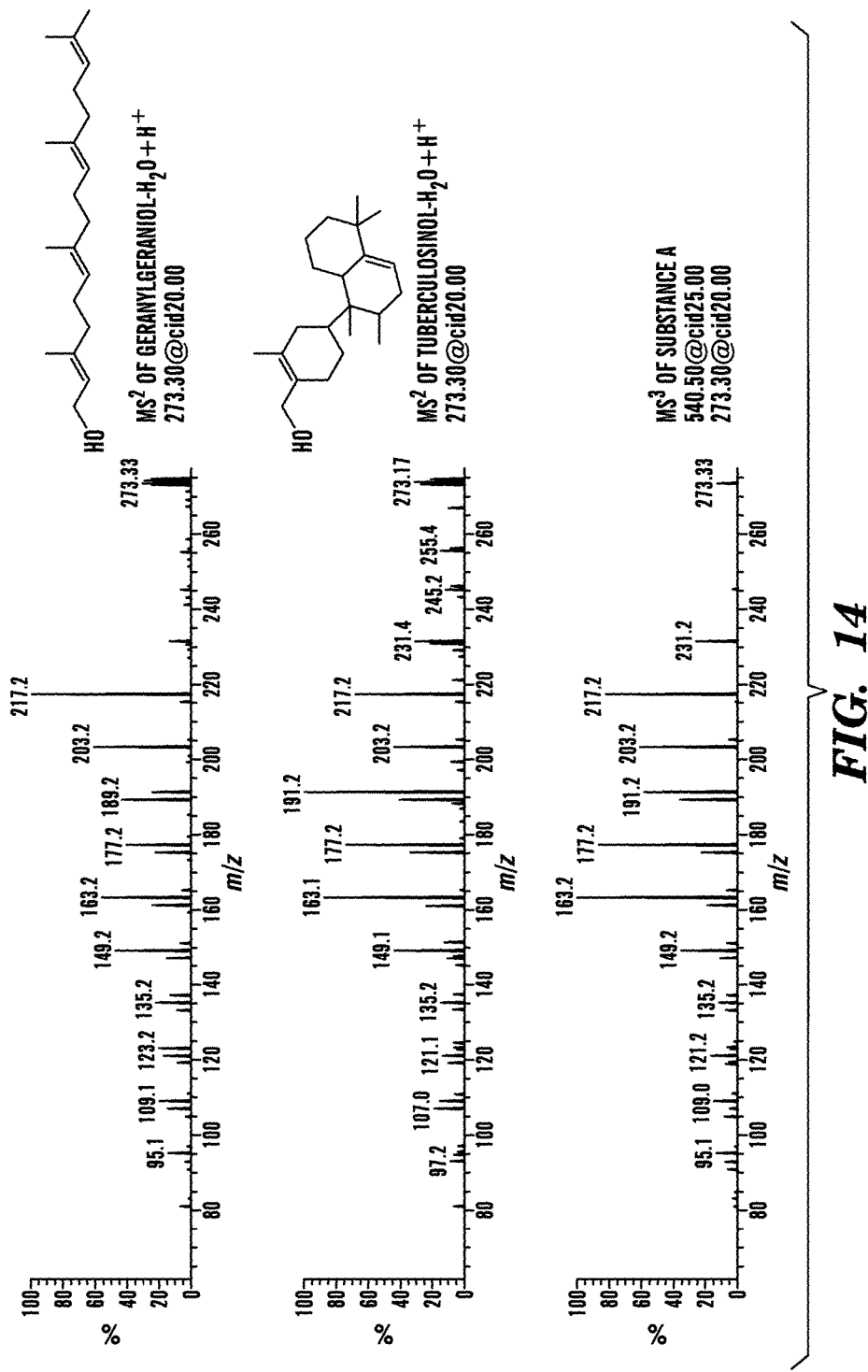
FIG. 14 shows spectrum data. Collisional Mass Spectrometry generates a low mass ion series of geranylgeraniol, tuberculosinol and substance A. The low-mass ion series of geranylgeraniol and tuberculosinol are compared with the MS3 spectrum of substance A from M. tuberculosis. Under nanoelectrospray conditions using methanol at 700 V, the diterepene alcohols yielded ions arising from loss of water from the protonated parent alcohol that are analogous to the m/z 273 ion found in the spectrum of 1-TbAd (substance A). All three samples produce similar CID spectra, but the relative peak intensities of fragment ions of 1-TbAd more closely match those of tuberculosinol than geranylgeraniol, particularly for ions corresponding to m/z 191.2, 189.2 and 163.2.

Collision-induced mass spectrometry (CID-MS) identified the structural components of substance A as adenine ($[M+H]^+$, $C_5H_6N_5$, m/z 136.0618), adenosine ($[M+H]^+$, $C_{10}H_{14}N_5O_4$, m/z 268.1040), and a polyunsaturated C20 hydrocarbon ($[M+H]^+$, $C_{20}H_{33}$, m/z 273.2576) (FIG. 2 and FIG. 14). A common C20 diterpene is geranylgeraniol, and M. tuberculosis produces two C20 lipids containing bicyclic hallimanane skeletons, tuberculosinol and isotuberculosinol (18-20). Initially, CID-MS spectra could not distinguish among these three candidate diterpenes (FIG. 14, FIG. 15), but multi-stage CID-MS studies isolated the diterpene unit of substance A (m/z 273.3) and yielded collision patterns that matched tuberculosinol more closely than geranylgeraniol (FIG. 14).

After purification of the natural product, we carried out NMR spectroscopy analyses using $^1H$ 1D, 2D COSY, HMQC and NOESY spectra (data not shown, Summary FIG. 15), which unequivocally established the structure of substance A as 1-tuberculosinyladenosine (1-TbAd) (FIG. 2). The NMR signals of the diterpene moiety matched those of tuberculosinol (10, 19-21) except for the expected difference in the side chain protons and carbons. The spectral data of the adenosine and adjacent atoms correspond closely to those of 1-prenyladenosine analogues (22-24). The allylic methylene group absorbs downfield as a doublet at δ 4.92 (J=6.6 Hz). A NOESY cross peak between the adenine H-2 at δ 8.53 and the alkene hydrogen and allylic methylene, and methyl groups at δ 5.46, 4.92 and 1.89, respectively, confirm that the tuberculosinyl group is attached to the adenine at position 1. Thus, M. tuberculosis produces a previously unknown type of diterpene nucleoside.

Rv3378c Produces 1-TbAd

To identify the genes necessary for 1-TbAd production, an existing library of random transposon insertional mutants (25) was screened in high throughput (4,196 mutants) for 1-TbAd production using a simplified 3 minute HPLC-MS method (FIG. 3A). Thirty mutants showing low or absent signals were rescreened using the original, high resolution lipidomic separation method (FIG. 1). Reporting only mutants with complete signal loss of TbAd signal in both assays, we identified two 1-TbAd-null mutants carrying transposons in Rv1796 (mutant 1) and Rv2867c (mutant 2) (FIG. 3B). The concurrently performed biochemical studies described above identified the highly characteristic tuberculosinyl moiety as a component of 1-TbAd, and the Rv3377c-Rv3378c locus was known to encode enzymes needed for tuberculosinol production (10, 11, 18-21). Sequencing identified spontaneous mutations in Rv3378c in both mutants (10, 18-21). Mutant 1 encoded a predicted Asp→Gly substitution at residue 34, and mutant 2 encoded a Pro→Ser substitution at residue 231. We generated complementation constructs to separately test whether the point mutations in Rv3378c or the transposon insertions were responsible for 1-TbAd loss. Transfer of Rv1796 and Rv2867c failed to restore 1-TbAd production (FIG. 9), but transfer of Rv3377c-Rv3378c reconstituted 1-TbAd production in both mutants (FIG. 3C). Thus, Rv3377c-Rv3378c genes are necessary for 1-TbAd biosynthesis in M. tuberculosis.

The Biosynthetic Pathway of 1-TbAd

Further, the known role of Rv3377-Rv3378c in tuberculosinol production potentially provided a mechanism to connect these genes with the production of a nucleotide-modified tuberculosinol. Rv3377c is a terpene cyclase, which acts on geranylgeranyl pyrophosphate (GGPP) to generate tuberculosinyl pyrophosphate (TbPP). Rv3378c was thought to be a phosphatase, which converts TbPP to free tuberculosinol (10, 21). Extending current models (FIG. 4A), 1-TbAd might result from downstream action of an unknown gene on free tuberculosinol to transfer it to adenosine. Polyprenyl synthase genes and the Rv3377c-Rv3378c locus are coordinately regulated and encoded at adjacent sites on the chromosome (26). Therefore, we searched M. tuberculosis databases for genes located near this locus that might plausibly function as adenosine transferases. We failed to find candidates and noted that no transposon insertion that blocked 1-TbAd production mapped to genes adjacent to this loci.

Figure 4B:
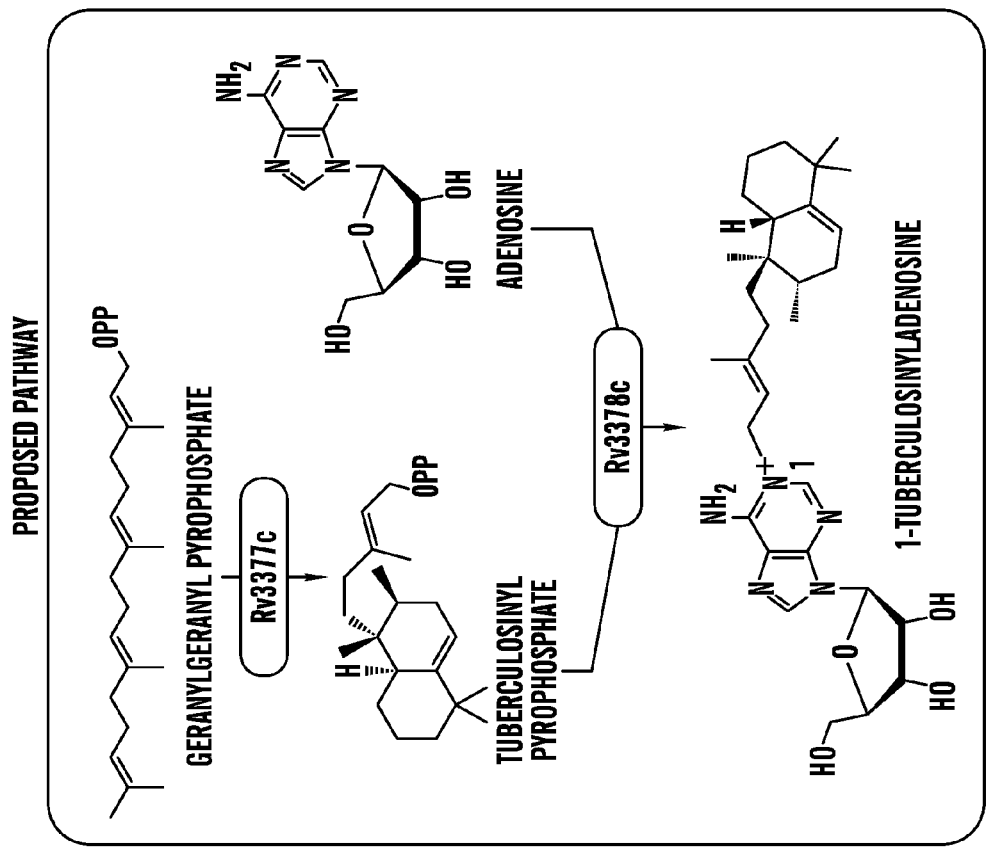
FIGS. 4A to 4D show schematics of 1-TbAd synthesis (FIG. 4A and FIG. 4B), and ion chromatograms of synthesis indicating that Rv3378c acts as a tuberculosinyl transferase (FIGS. 4C and 4D).
Figure 4A:
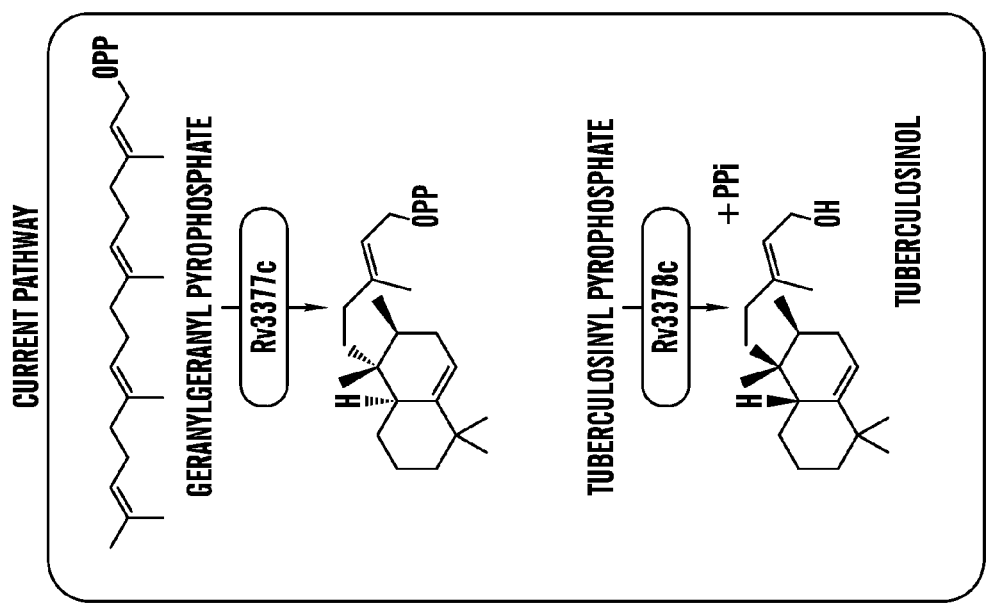
Figure 4C:
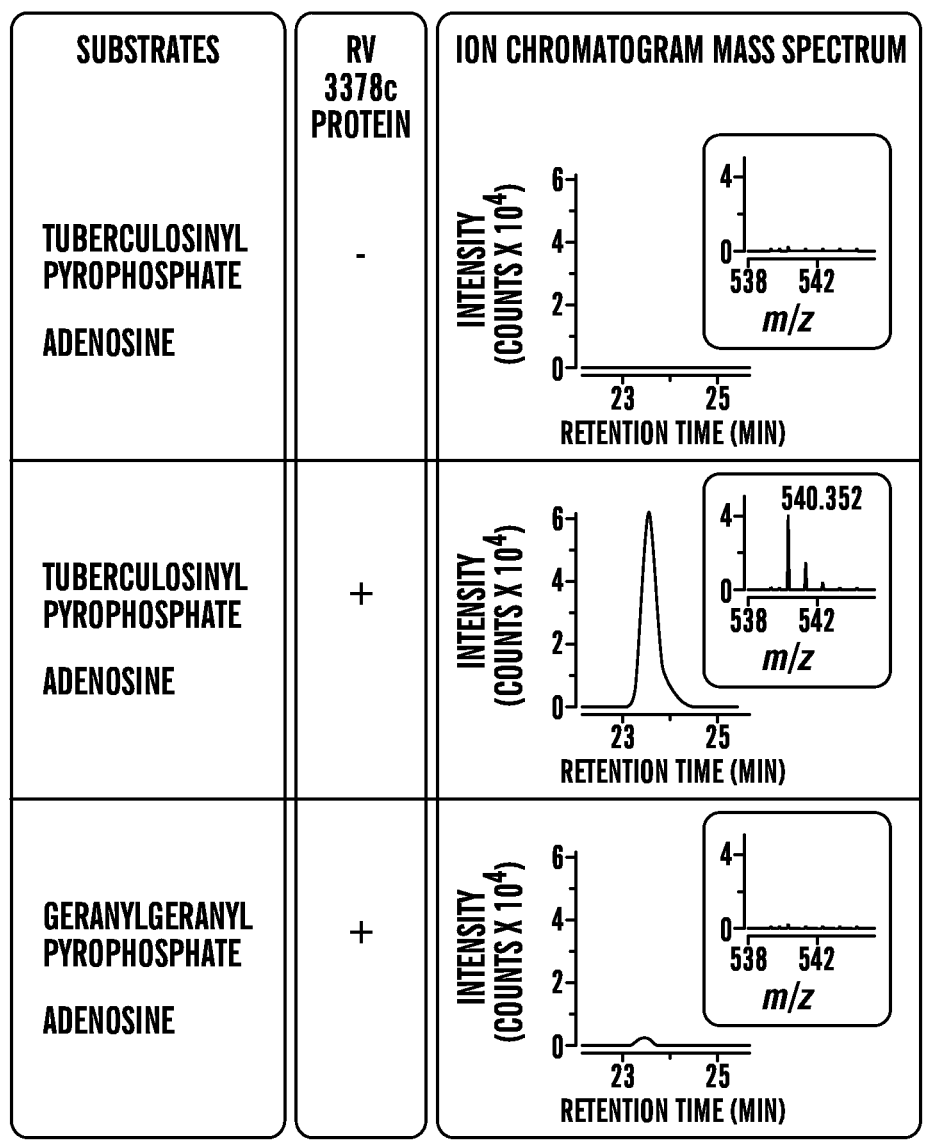
Figure 4D:
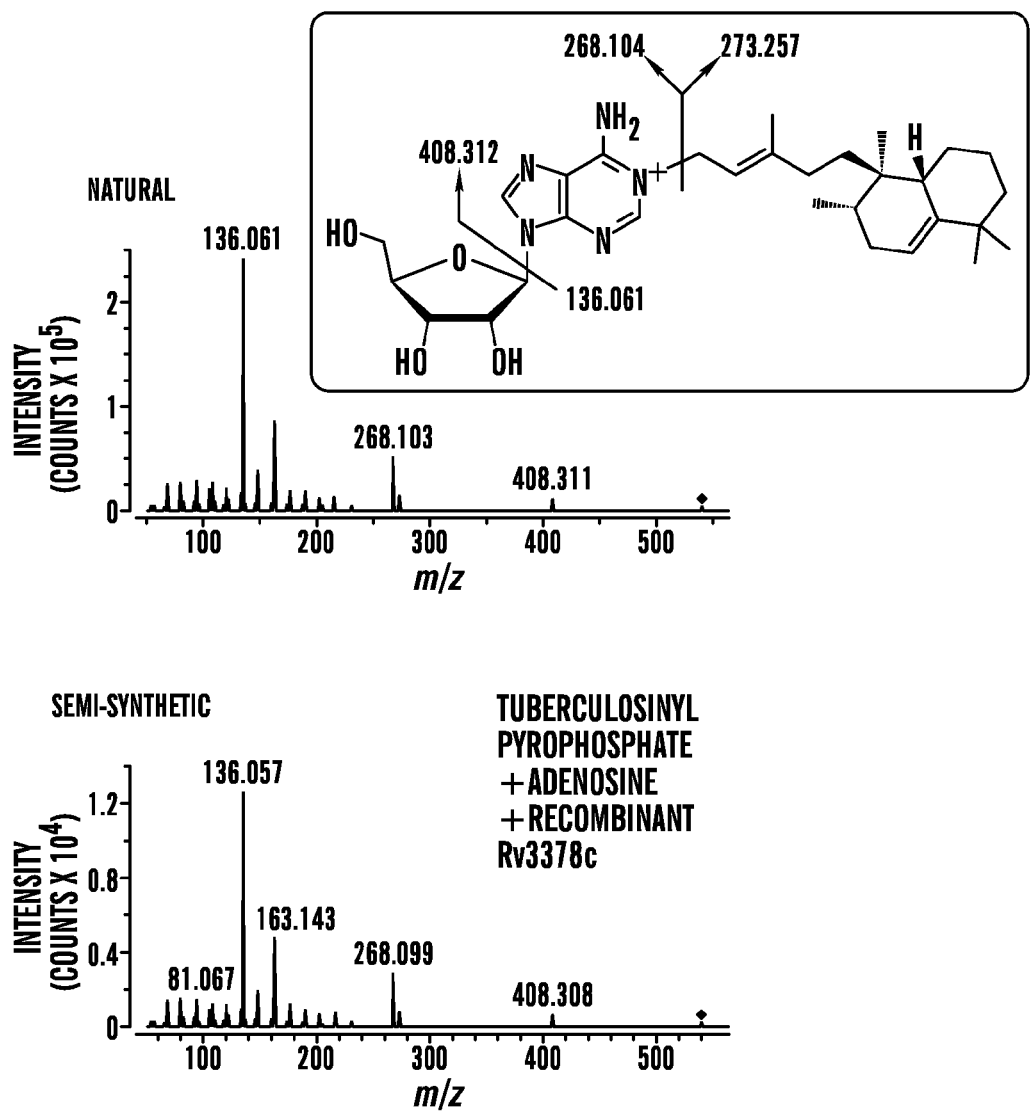

Therefore, we considered a new biosynthetic model in which Rv3378c protein is not a simple phosphatase, as currently believed, but instead acts with combined phosphatase and tuberculosinyl transferase functions, using adenosine as the nucleophilic substrate (FIG. 4B). This model is mechanistically simple and might explain the lack of an apparent stand-alone transferase gene. Also, whereas current models predict that tuberculosinol is the end product of this pathway, we did not detect tuberculosinol in lipidomics experiments (FIG. 1A and data not shown). The revised model posits that 1-TbAd is the endproduct of Rv3378c pathway, explaining why it accumulates to high levels as one of the brightest ions in the lipidome (FIG. 1A). After chemical synthesis of TbPP, we tested TbPP and GGPP as substrates for the recombinant Rv3378c protein (18). Rv3378c catalyzed the condensation of adenosine and TbPP to generate 1-TbAd, but produced little or no product from GGPP and free tuberculosinol was not detected in these assays (FIG. 4C and FIG. 4D). Thus, Rv3378c is a tuberculosinyl transferase ruling in the revised biosynthetic pathway (FIG. 4B).

Rv3377c-Rv3378c is Sufficient for TbAd Biosynthesis in Cells

Figure 5:
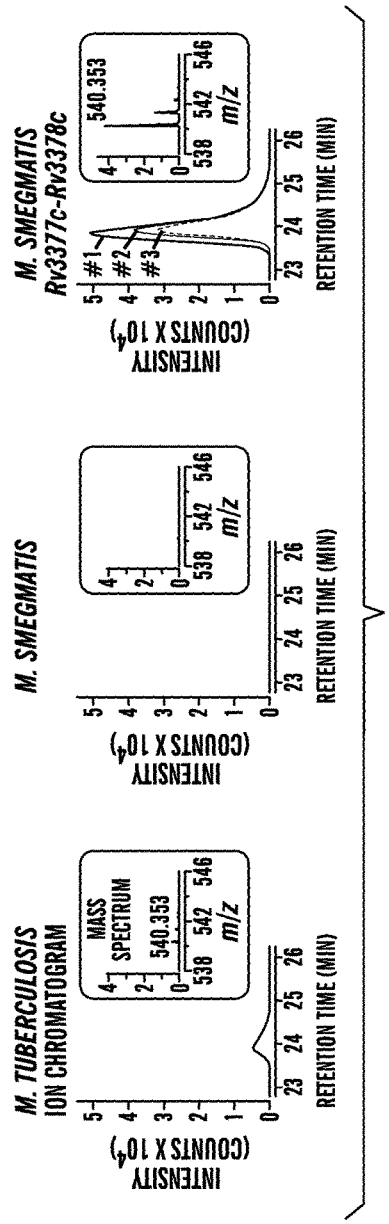
FIG. 5 shows extracted ion chromatograms and mass spectra (insets) depicting the expression of Rv3377c-Rv3378c is sufficient for production of 1-TbAd in *M. smegmatis*. Extracted ion chromatograms and mass spectra (insets) of 1-TbAd (m/z 540.3545) for the HPLC-MS analysis of lipid extracts from *M. tuberculosis, M. smegmatis* parental or Rv3377c-Rv3378c knock in strains.
Figure 10:
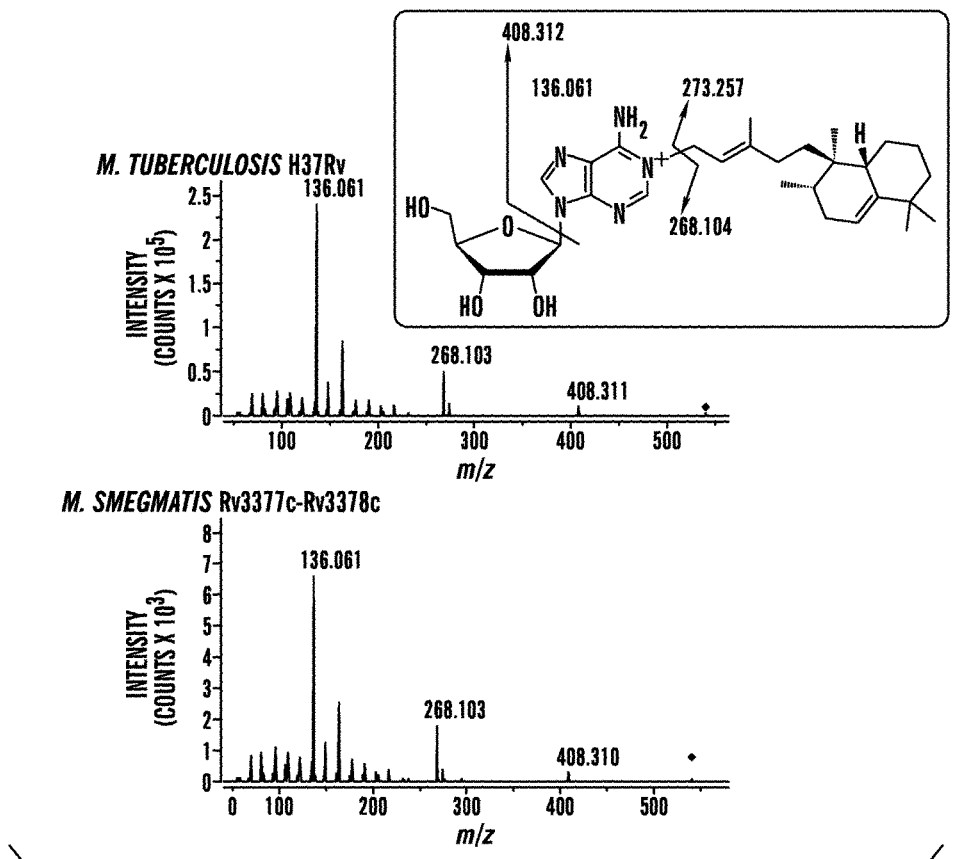
FIG. 10 shows collision peak data indicating that expression of Rv3377c-Rv3378c in M. smegmatis is sufficient for the biosynthesis of 1-TbAd. Collisional experiment on the molecule detected, at the same m/z and retention time as M. tuberculosis 1-Tbad, in the lipid extract of M. smegmatis transformed by Rv3377c-Rv3378c, which also shows the characteristic fragmentation pattern of 1-TbAd. Thus, 1-TbAd is the produce of the Rv3377c3378c locus.

To test the sufficiency of this locus for 1-TbAd production in cells, we transferred the Rv3377c-Rv3378c locus to M. smegmatis. In all three clones tested, expression of Rv3377c-Rv3378c transferred production of a molecule with the mass, retention time and CID-MS spectrum of 1-TbAd (FIG. 5 and FIG. 10). Thus, no other M. tuberculosis-specific co-factor or transporter is needed for 1-TbAd production. Rv3377c-Rv3378c is sufficient to synthesize 1-TbAd from ubiquitous cellular precursors present in most bacteria, likely GGPP and adenosine.

Crystal Structure of Rv3378c

Figure 6A:
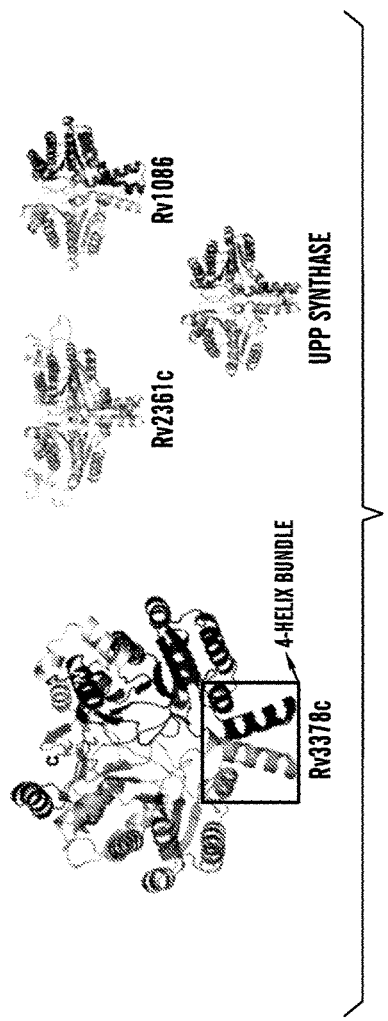
FIGS. 6A to 6E show schematics of the molecular structure of Rv3378c. Rv3378c adopts a (Z)-prenyl transferase fold.
Figure 6C:
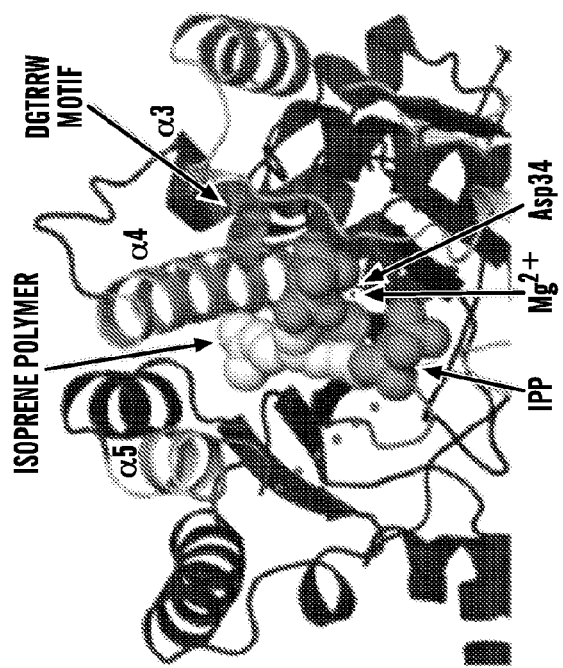
Figure 6B:
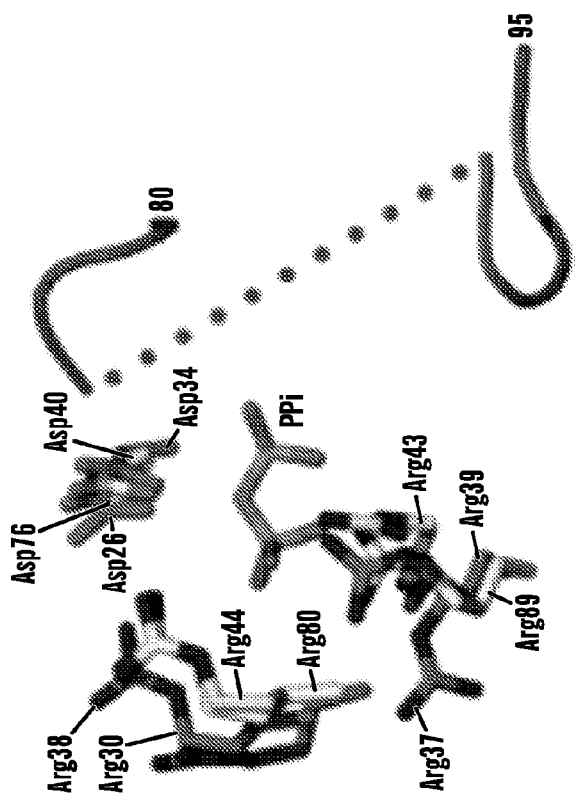
Figure 6E:
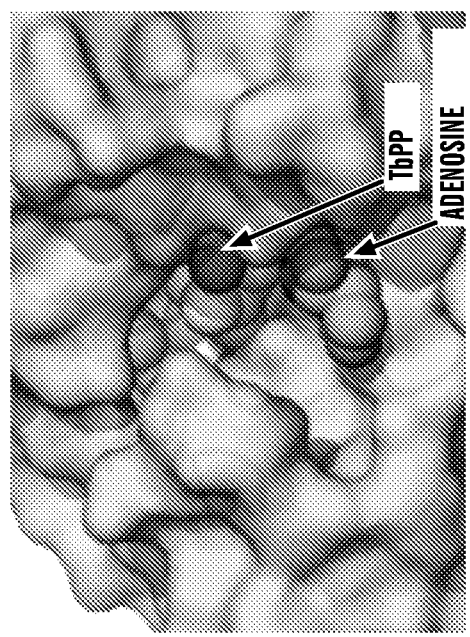

To understand if the active site of Rv3378c is compatible with the revised function as a tuberculosinyl transferase, we determined its crystal structure. Lacking proteins with high sequence similarity, single-wavelength anomalous dispersion phasing was used to calculate the initial electron density map. The model was refined against native data to 2.2 Å resolution (data not shown). As expected from gel filtration studies, Rv3378c formed a homodimer (FIG. 6A). Although structural similarity was not predicted by sequence comparisons, Rv3378c adopts the fold seen in (Z)-prenyl, or cis-prenyl transferases (27), including M. tuberculosis (Z)-farnesyl diphosphate synthase (Rv1086) and decaprenyl pyrophosphate synthase (Rv2361c), as well as E. coli undecaprenyl pyrophosphate synthase (UPP) (28, 29) (FIG. 6B).

These enzymes condense an allyl pyrophosphate and the 5-carbon isopentyl pyrophosphate building block to produce linear isoprenoids (28, 29).

Structural Insight into Prenyl Unit Binding

In considering competing models that Rv3378c might simply hydrolyze the TbPP pyrophosphate, or carry out the newly proposed role in adenosine transfer (FIG. 5A and FIG. 5B), we superimposed Rv3378c with the pseudo-substrate and product complexes of Rv2361c (29) to model an enzyme-substrate (ES) complex. In contrast to other (Z)-prenyl transferases, Rv3378c has a unique C-terminal helical segment (residues 251-end), which contributes to domain swapping. An extra N-terminal helical segment (residues 6-24) packs via hydrophobic interactions with adjacent helices (FIG. 6A and data not shown,).

Figure 6D:
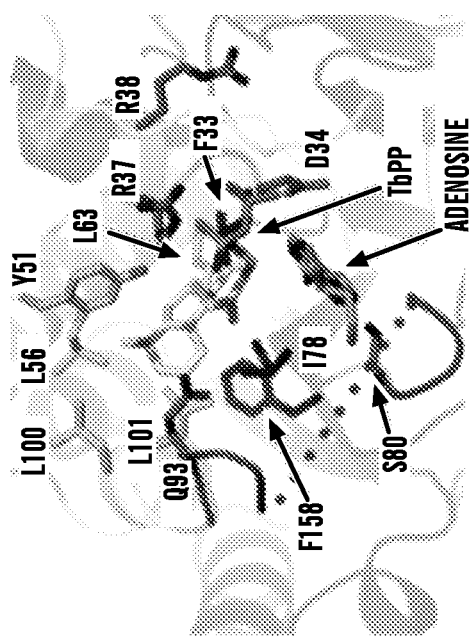
Figure 7B:
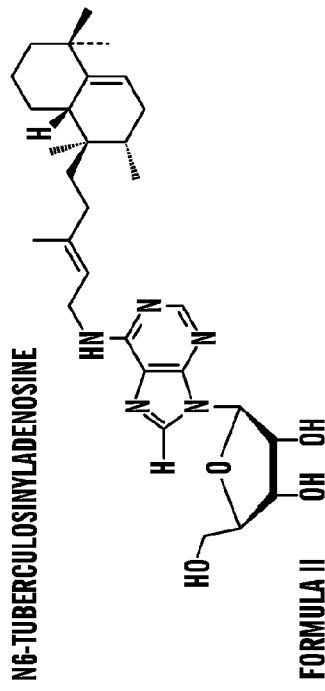
FIGS. 7A to 7B shows the chemical structures of (FIG. 7A) Formula I (1-tuberculosinyladenosine (1-TbAd))
Figure 7A:
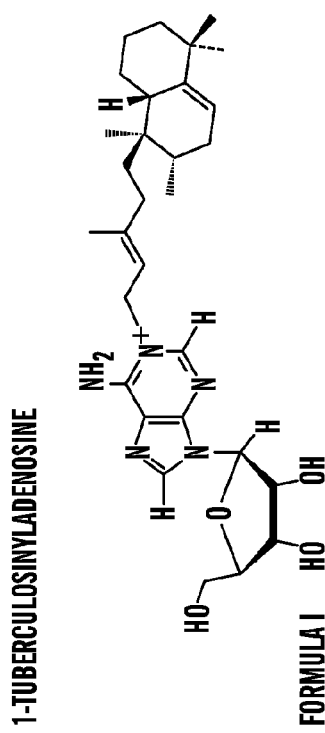
Figure 7C:
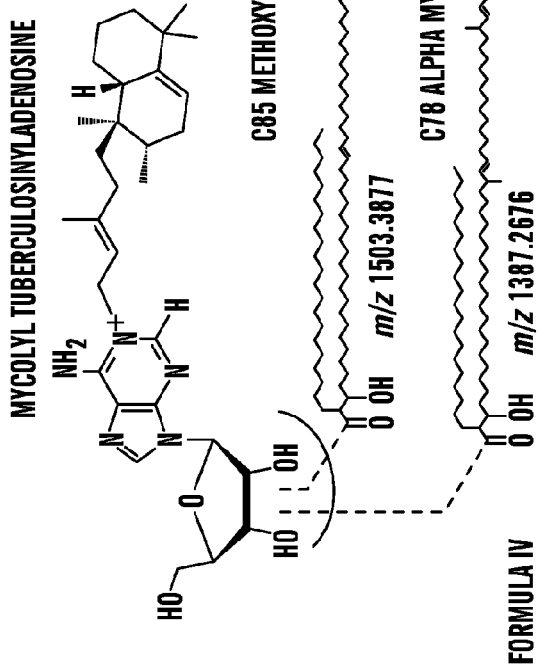
(FIG. 7C) Formula IV (mycoloyl-tuberculosinyladenosine (MTbAd)), that have been determined to be specific for M. tuberculosis.
Figure 11:
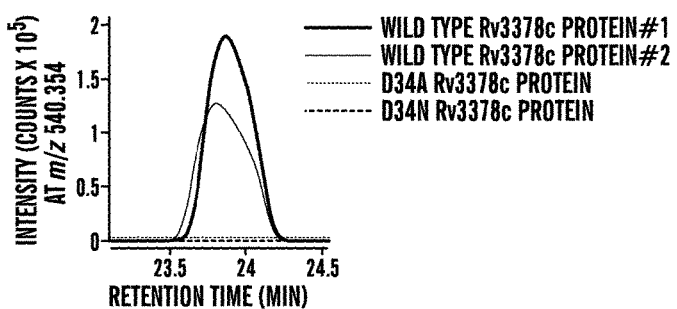
FIG. 11 shows ion chromatograms depicting that aspartate 34 is required for the terpenyl transferase activity of Rv3378c in vitro. Ion chromatograms of the 1-TbAd in reaction products of enzymatic assays performed using wild type or aspartate 34 mutant Rv3378c protein.
Figure 12:
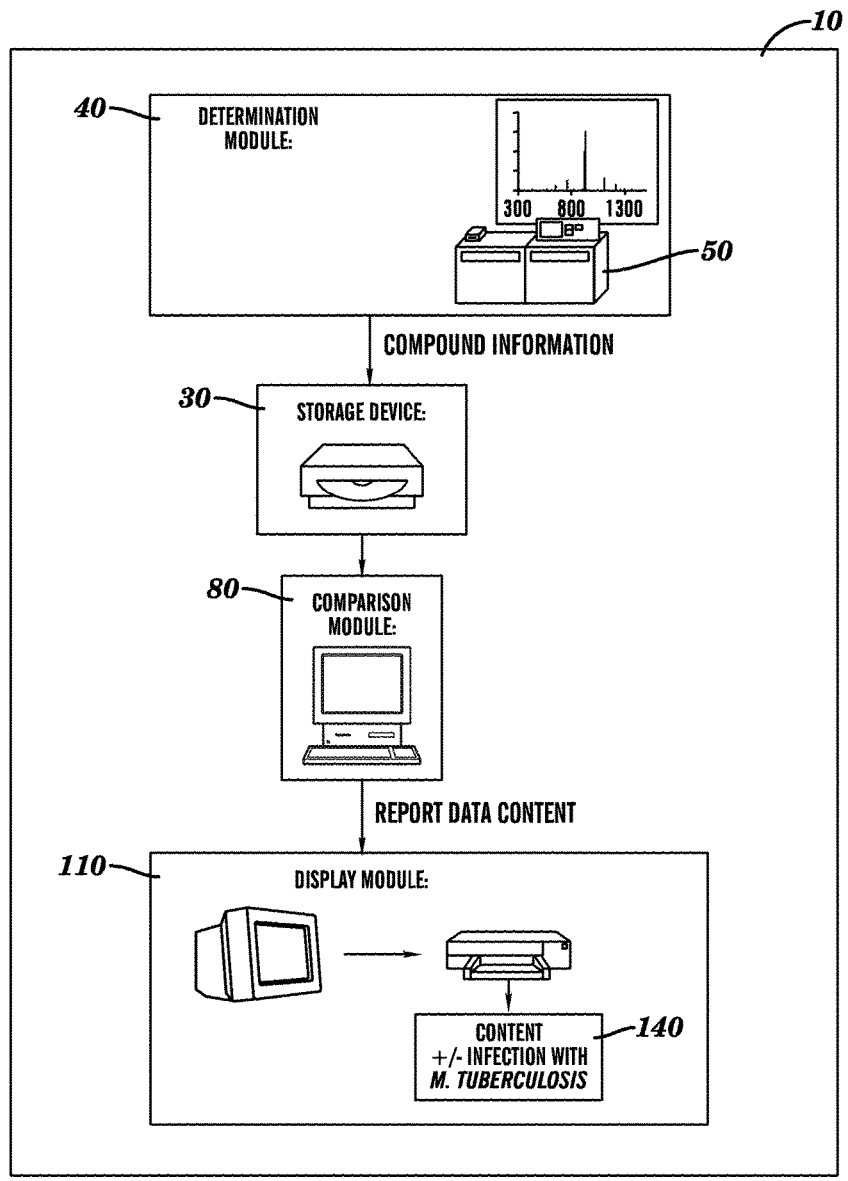
FIG. 12 shows a block diagram showing an example of a system for determining a need for treatment of M. tuberculosis infection.
Figure 13:
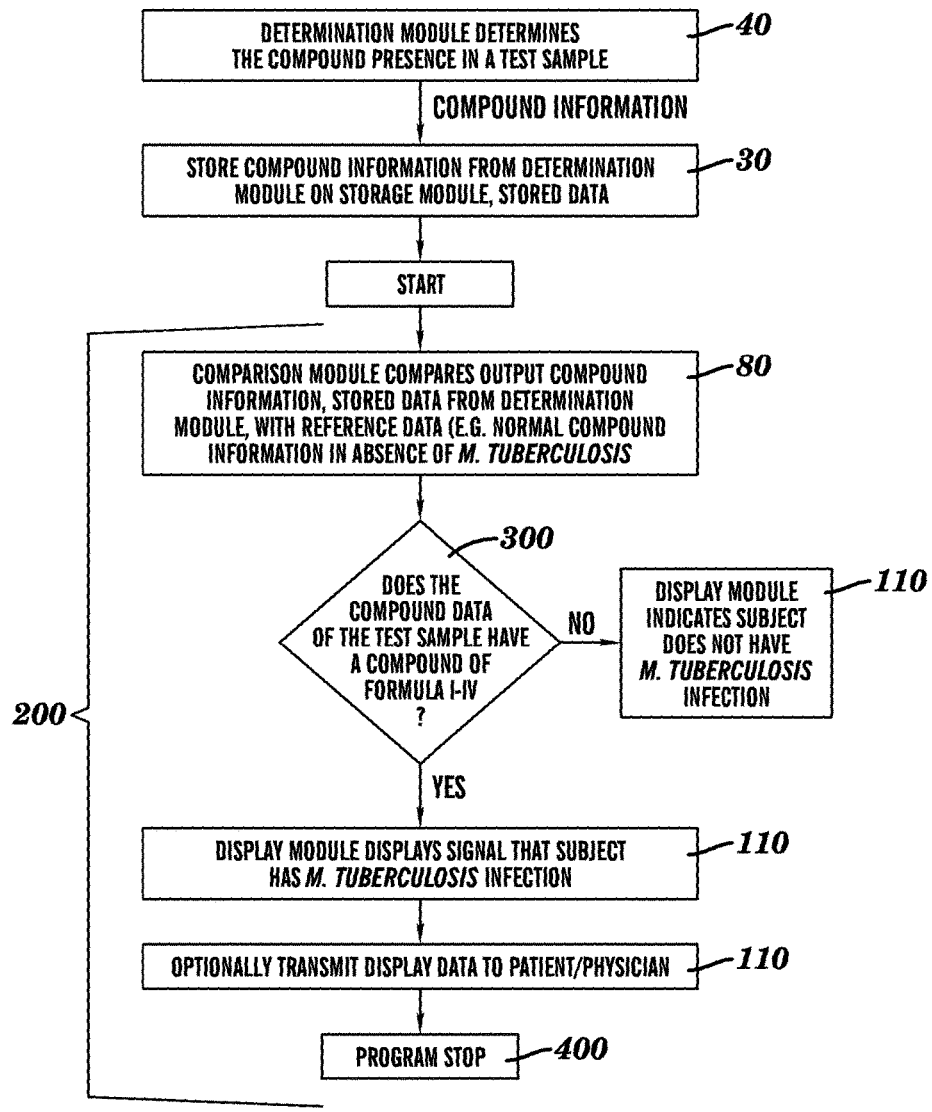
FIG. 13 shows a block diagram showing exemplary instructions on a computer readable medium for determining M. tuberculosis (TB) infection in an individual.

Rv3378c shares functional motifs with the (Z)-prenyl transferases, including residues for substrate binding and catalysis; Asp34, Arg37 and Arg38 (FIG. 6B). (Z)-prenyl transferases bind the allyl pyrophosphate substrate through a characteristic DGNG/RRW amino acid sequence motif starting two residues before the N-terminus of an alpha helix (α3). The aspartate chelates a magnesium ion, while the glycine, the helix terminus and the arginine(s) engage the pyrophosphate (FIG. 6B and FIG. 6C) (27, 28, 30). In Rv3378c, Asp34 sits in the expected position to carry out its essential catalytic function providing a specific mechanism that likely explains why mutant 1, which contains an Asp34→Gly alteration, does not produce TbAd. As predicted by prior studies showing the role of aspartate in prenyl transfer (27, 28, 30), and the conserved location of Asp34 vis-à-vis the prenyl binding site (FIGS. 6A-B), mutation to asparagine or alanine abolished the prenyl transferase function of Rv3378c (FIG. 11). In Rv2361c, the isoprene binding site is a hydrophobic pocket located between the β-sheet and the α2 (residues 89-110) and α3 (residues 129-152) helices (29). Rv3378c contains all of these features (FIG. 6C), including the 34-DGTRRW-39 motif and a deep pocket adjacent to helices α4 (residues 51-68) and α5 (residues 96-103). Hydrophobic residues (L56, L63, L100 and L101) are located in the pocket created by helices α4 and α5, and other hydrophobic residues (F33, 178, F158) further contribute to the hydrophobic character of the pocket. This binding pocket is predicted to position the pyrophosphate group of TbPP, which can interact with Arg37 and Arg38 from the DGTRRW motif and Tyr51 from the N-terminus of helix α4 (FIG. 6D).

A Second Pocket at the Catalytic Site

The binding mode of the nucleophilic adenosine substrate is harder to model, because the binding site is likely to be completed by the closure of the P-loop over the active site when native substrate is present. The P-loop is disordered in the unliganded structure, but it becomes ordered in a non-physiological complex with mellitic acid (data not shown). This structure suggests a specific mechanism by which substrate binding provides polar interactions with the P-loop to exclude water from the active site. Other considerations provide pertinent clues about the adenosine binding mode. As contrasted with Rv2361c, Rv1086 and UPP synthase, Rv3378c has a second, side pocket that can accommodate adenosine (FIGS. 6D and E). Superimposing N1 of the adenine on the IPP nucleophile in complex with Rv2361c (29) guides the positioning of the adenosine substrate in the active site of Rv3378c. In Rv2361c, the pyrophosphate of IPP interacts with Arg244 and Arg250 (29). Corresponding to the fact that adenosine lacks the pyrophosphate, Rv3378c lacks this conserved pair of arginines, which are replaced with glycine and serine. These features distinguish Rv3378c from known (Z)-prenyl transferases and are consistent with adenosine binding and transfer.

Substance B Contains a Core TbAd Structure

Returning to the whole-organism screen (FIG. 1a), an independent effort to characterize substance B uncovered unexpected structural similarities to TbAd (substance A). The B cluster of 66 features was deconvoluted to identify individual features with properties of members of an alkyl series. The 66 features represented a pattern of two overlapping but non-identical alkyl series (B1 and B2) and their isotopes (data not shown). In particular, comparison of m/z 1659.514 and m/z 1775.632, which were the dominant molecular ions in the two alkyl series, yields a mass difference of 116.117 amu (data not shown). This mass difference matches within 0.003 amu to C7F1100, the characteristic difference between alpha (fCH2],e-CH=CH—CH3) and methoxy ((CH2lo9-OCH3) mycolic acid. Separately, the detected m/z at 1659.514 (calculated 1659.510) and 1775.632 (calculated 1775.630) correspond to the expected masses of TbAd substituted with C78 a- and C85 methoxy-mycolic acids, respectively (data not shown).

Confirming the hypothesis that these ions represented mycolyl TbAd (MTbAd), CID-MS yielded the diagnostic fragments observed in the TbAd MS/MS spectrum, including ions at m/z 136.06, 273.25, and 408.31 assigned to protonated adducts of adenine, tuberculosinol, and tuberculosinyl adenine motifs, respectively (data not shown). Furthermore, the fragments detected at 1387.263 (calculate 1387.267) and 1503.375 (calculated 1503.387) m/z matched those of a C78 alpha and a C85 methoxy mycolic acid-linked adenosine, respectively (data not shown). Last, all 66 features detected in the B cluster could be explained by an alkyl series and isotopes of TbAd carrying individual mycolic acids with expected chain length (C76-C88) and R-groups patterns normally produced by M. tuberculosis (FIG. 1A). In contrast to TbAd, ions corresponding to MTbAd were weak (FIG. 1A), and the natural MTbAd product could not be purified in adequate yield for NMR studies. Nevertheless, the CID-MS spectra, mass accuracy and one to one correspondence of 15 deduced structures to the known chain length and R-group variants of naturally occurring mycolyl variants provide strong evidence for mycoloylated form of TbAd in M. tuberculosis.

Rv3378c Connects Biosynthetic Pathways

Nearly all bacteria express the enzymes needed for biosynthesis of terpenes and nucleosides, which normally have quite distinct functions in cell biology. However, these data suggested a model in which M. tuberculosis' expression of Rv3377c-3378c operon provides an unexpected connection of these evolutionary ubiquitous pathways to create a hybrid terpene-nucleoside, which has few precedents in nature. TbAd itself might show broader expression or strict restriction to M. tuberculosis. To study the distribution of TbAd among microbes, HPLC-MS monitoring for TbAd ions failed to detect signal in total lipid extracts from representative fungal (C. albicans, A. fumigatus), Gram-positive (S. aureus) and Gram-negative (E. coli) bacterial species (data not shown). Among bacteria more closely related to M. tuberculosis, we could not detect TbAd ions in non-mycobacterial Actinomycetales, environmental mycobacteria (M. smegmatis, M. fallax) or M. bovis (data not shown). Ions matching TbAd were present in three divergent M. tuberculosis reference strain (FIG. 1B) and clinical isolates (data not shown) of M. tuberculosis. This pattern of TbAd production matches the distribution of the Rv3377c-Rv3378c operon, which is expressed only in M. tuberculosis strains. M. bovis BCG contains the operon but, as in M. bovis, Rv3377c is inactivated by a frameshift mutation 27. In considering how *M. tuberculosis*, among all tested organisms, acquired the TbAd biosynthesis pathway, we wondered whether Rv3377c-3378c was sufficient to make TbAd in an unrelated *mycobacterium*, or whether other unknown, but specialized *M. tuberculosis*-encoded accessory molecules or transport systems might be involved. The expression of Rv3377c-3378c in *M. smegmatis* was sufficient for production of TbAd among all three isolates tested (FIG. 5). Thus, transfer of the Rv3377c-Rv3378c genes is sufficient to reconstitute the TbAd biosynthesis in intact *M. smegmatis*. In contrast, the mycoloylated forms of TbAd were not detected in *M. smegmatis* knock-in strain suggesting that the generation of these acylated TbAd requires *M. tuberculosis* specific mycolyl transferase.

Here we report the discovery of TbAd as an abundant extracellular product of *M. tuberculosis*. This novel compound was detected in three forms, N'-TbAd (positively charged at neutral pH), $N^6$-TbAd (neutral at neutral pH; Young et al., submitted) and mycoloyl-TbAd. The constitutive production of these compounds under several growth conditions confirms their classification as natural products. T bAd distinguishes virulent *M. tuberculosis* from all other species, including the BCG vaccine strain, environmental mycobacteria, and other non-Actinomycetales bacteria. Among microbes studied to date, the pattern of Rv3377c-Rv3378c expression is in agreement with previously described horizontal acquisition of Rv3376-Rv3378c by *M. tuberculosis* complex. Importantly, this distribution implies that TbAd is an abundant biomarker specific for *M. tuberculosis*.

Higher order terpene-nucleosides are rare in nature, and we have not identified a direct precedent for N'-linked prenyl adenosines. A C35 terpene cyclase activity is found in non-pathogenic mycobacteria 28'29, however Rv3377c orthologs are only functional in *M. tuberculosis* strains. Plants and marine sponges produce terpene-pu.

In an attempt to determine if a bacteria or cellular organisms other than *M. tuberculosis* produce 1-TbAd, we sought orthologs of Rv3377c and Rv3378c, the two enzymes required for TbAd synthesis in *M. tuberculosis*. We focused on organisms that commonly cause lung disease or are used for vaccination in ways that can cause false positive ELISA tests. The basic local alignment search tool (BLAST) and a low stringency match criterion (30 percent amino sequence identity) failed to identify two orthologs of these biosynthetic genes in any species. Considering even bacteria with high genetic relatedness to *M. tuberculosis*, orthologs of Rv3377c and Rv3378c could not be identified in most actinobacteria, including disease-causing members of the *M. avium* complex, *M. kansasii* and *M. marinum*. Within the *M. tuberculosis* complex (MTC), *M. bovis* and the vaccine strain *M. bovis* BCG (Pasteur strain), *M. Cannetti* and *M. africanum* encode identifiable orthologs of both genes. However, many coding mutations are found in this locus in MTC species other than *M. tuberculosis*. These include (G31V) in Rv3377c of *M. africanum*. and *M. cannetti* has four coding mutations (T253A, V340I, A357Q, V361I, R497E). Rv3378c in *M. cannetti* (L230I). *M. bovis* and the Pasteur strain of BCG (Pasteur) encode a frameshift mutation at nucleotide 1223, and Pasteur encodes a second point mutation (A137V). Frameshift mutations typically inactivate the enzyme, and the frameshift likely represents a cause of the known lack of 1-TbAd detected in the Pasteur strain of BCG. Further we found that all of the common BCG strains used worldwide for vaccination (Pasteur, Copenhagen, Japan, Mexican, Australian, Russia, Glaxo, Prague, Phipps, Connaught, Denmark, Tice) all contained the inactivating mutation, so one TbAd is likely absent from all commonly used BCG vaccines in the world.

Direct biochemical analysis of key strains for 1-TbAd production focused on microbes whose infection might mimic tuberculosis disease. As expected from the genetic analysis, lipid extracts from non-actinomycetes (*Escherichia coli, Staphylococcus aureus*) and fungi (*Aspergillis fumigatus, Candida albicans*) did not produce 1-TbAd signals.

Turning to mycobacteria, we could not detect 1-TbAd by HPLC-MS among reference strains of environmental (*M. fallax*) or non-pathogenic laboratory strains of mycobacteria (*M. smegmatis, M. phlei*) that lack Rv3378c orthologs. In agreement with genetic results, we did not detect 1-TbAd among disease causing bacteria that are related to *M. tuberculosis* but lack identifiable orthologs of Rv3377c-3378c (*M. avium, M. marinum*) or those with orthologous loci with a known frameshift mutation (*M. bovis*). Among all strains tested to date, only *M. tuberculosis* produces 1-TbAd at detectable concentrations. These data support the conclusion that 1-TbAd and its biosynthetic genes are lacking from most or all mycobacteria other than *M. tuberculosis*. Specifically 1-TbAd and its genes were not detected in any known environmental bacterium. Thus, environmental bacteria are unlikely to cause false positive results in tests that target 1-TbAd or patient antibodies to 1-TbAd.

Discussion

Overall, structural, genetic and biochemical data strongly suggest a revised function of Rv3378c as a tuberculosinyl transferase that produces 1-TbAd, an abundant amphiphile that is exported outside *M. tuberculosis*. This result establishes the efficacy of unbiased lipidomic screens to identify previously unknown compounds. A C35 terpene cyclase activity is found in non-pathogenic mycobacteria (31, 32), but Rv3377c orthologs are only known within *M. tuberculosis* complex. Higher order terpene-nucleosides are rare in nature, and we have not identified a precedent for 1-linked prenyl adenosines. Plant and marine sponges produce terpene-purine derivatives, such as cytokinins and agelasines, which regulate growth or show antimicrobial effects (33). However, these natural products contain adenine rather than adenosine, and the terpene moiety is carried at the $N^6$ position of the adenine in the cytokinins and $N^7$ or $N^9$ in the agelasines. Further, among microbes studied to date, we have only detected 1-TbAd in members of the *M. tuberculosis* complex, suggesting that 1-TbAd production is limited to pathogenic mycobacteria. Orthologs of Rv3377c or RV3378c are limited to the *M. tuberculosis* complex. Although *M. bovis* and BCG strains encode orthologous genes, strains examined to date encodes a frameshift mutation in Rv3377c (11), and the Pasteur strain used here encodes a second, coding point mutation in Rv3378c. Thus, both genetic and biochemical evidence suggest that 1-TbAd is a specific marker of *M. tuberculosis*, supporting the development of 1-TbAd or 1-TbAd-specific immune responses as candidate targets for diagnostic tests for tuberculosis.

The lack of 1-TbAd in BCG might represent evidence that changes in Rv3377c-Rv3378c might contribute to the vaccine strain's attenuation. More direct evidence for a role of this locus in virulence comes from transposon studies showing that Rv3377c and Rv3378c play non-redundant roles in phagosome-lysosome fusion and survival in macrophages (13). This key finding initiated an intensive search for the actual functions of these virulence-associated genes. Rv3377c is a terpene cyclase (18-20). Rv3378c has few orthologs in nature, and its biochemical function was not apparent from predictive folding algorithms. Based on in vitro studies, Rv3378c is currently thought to function as a TbPP pyrophosphatase that yields free tuberculosinol (10). Synthetic tuberculosinols coupled to beads block phagosomal acidification (21). However, end products of biosynthetic pathways typically accumulate, and to our knowledge, the extent of accumulation of free tuberculosinol as a natural product in intact *M. tuberculosis* remains unknown. We did not detect free tuberculosinols in lipidomics analysis of *M. tuberculosis* or among in vitro products of Rv3378c. This result does not rule out biosynthesis of free tuberculosinol, but it is notable that 1-TbAd is not only detected, it substantially accumulates within and outside *M. tuberculosis*. Further, we prove that the action of Rv3378c is a combined phosphatase and isotuberculosinol transferase through in vitro study of purified proteins, gene transfer to *M. tuberculosis* and *M. smegmatis*, as well as a structural analysis of Rv3378c. Based on parallel lines of genetic, biochemical and structural evidence, we propose that Rv3378c should be known as 'tuberculosinyl adenosine transferase'.

The structures of enzymes that transfer prenyl pyrophosphates to substrates other than linear isoprenoids have not been determined previously. Like other (Z)-prenyl transferases, Rv3378c contains a characteristic allyl pyrophosphate-binding site, catalytic aspartate and flexible P-loop in position to close over the active site. The canonical TbPP binding pocket structure is sufficiently conserved that it may be sensitive to available drugs or analogues that target other (Z)-prenyl transferases. However, the nucleophile binding site lacks conserved features that mediate recognition of pyrophosphate moiety of isoprene building blocks seen in previously characterized (Z)-prenyl transferases. Instead, Rv3378c active site contains a second, side-pocket in which the adenosine can be positioned for nucleophilic attack on C1 of TbPP. We observed this reaction in vitro and found that Rv3378c does not act on GGPP and specifically produces the 1-linked form of 1-TbAd, defining two aspects of the substrate specificity. Whereas most prenyl transferases have one identifiable pocket, this new two-pocket model suggests a broader paradigm for the prenylation of metabolites catalyzed by members of the (Z)-prenyl transferase family. Whereas current models emphasize iterative elongation through the repeated use of one pocket, the dual substrate pocket of Rv3378c provides a general model for prenylation of non-prenyl substrates. Product specificity is determined by a conventional allyl pyrophosphate binding site and a second pocket tailored to bind and activate each target nucleophile.

The larger 1-TbAd biosynthetic pathway starts with two evolutionarily conserved systems, which produce geranylgeranyl pyrophosphate and adenosine. These pathways operate separately in most organisms, but *M. tuberculosis* joins these two pathways to generate a terpene nucleoside. The appearance of TbAd after transfer of Rv3377c and Rv3378c genes to *M. smegmatis* proves that additional *M. tuberculosis*-specific genes, such as transporters are not required for 1-TbAd biosynthesis. More generally, these data represent an experimental demonstration that transfer of two genes is sufficient to reconstitute a complex metabolite, which likely requires more than twenty genes for its complete biosynthesis. Combining this observation with data suggesting that the ancestral Rv3377c and Rv3378c genes were acquired by horizontal gene transfer (26), a scenario emerges by which evolutionarily ancient terpene and nucleotide biosynthetic pathways were joined together by transfer of two genes late in the evolution of the *M. tuberculosis* complex (26).

1-TbAd likely represents the mechanism by which Rv3378c carries out its known effects in promoting *M. tuberculosis* infectivity. Within minutes of phagocytosis, *M. tuberculosis* inhibits host defenses, including phagosome acidification and phagolysosome fusion (34, 35). The Rv3377c-Rv3378c locus is required for optimal phagosome maturation arrest (13). The discovery of extracellular 1-TbAd provides specific insight into mechanisms by which an enzyme localized in the cytosol affects events outside the bacterium (13). To our knowledge, neither Rv3378c nor free tuberculosinol have been detected in culture filtrates (18). In contrast, 1-TbAd is an amphiphile that is released into the extracellular space using an export mechanism that is independent of ESX-1.

Future studies will be needed to understand the particular mechanisms by which 1-TbAd contributes to the effects of Rv3377c-Rv3378c on phagosome maturation. Adenosine is almost exclusively found inside cells, and terpene chains catalyze the transfer of pyrophosphate across the mycobacterial envelope for the biosynthesis of arabinogalactan (36). By analogy, prenylation might promote the transit of the nucleoside to the phagosomal space, where the adenosine could engage host receptors. Alternatively, tuberculosinol might be the active moiety (12, 21), whose solubility or transport is influenced by adenosine. The cellular mechanism leading to altered mycobacterial survival might include changed integrity of the phagosomal membrane, intraphagosomal proton capture, or escape of 1-TbAd across the phagosomal membrane and into the host, where it might signaling globally changes in macrophage function.

Supportive Information

Low Mass Ion Series of Substance A.

Enlargement of low-mass ion series detected in the MS2 (QTOF) spectrum of substance A from *M. tuberculosis* that shown in FIG. 8. The ion at m/z 136 is removed to simplify the graphical display. Four overlapping low-mass ion series were observed having from 1 to 4 unsaturations as expected for a $C_{20}H_{33}$ hydrocarbon cation undergoing a complex multi-step fragmentation. The ion series with 1, 2, 3 or 4 unsaturation(s) are connected by dashed lines.

Spectra were determined for, $^{1}H$ NMR spectra of *M. tuberculosis* 1-tuberculosinyl adenosine dissolved in $CD_3OD$; COSY NMR spectra of *M. tuberculosis* 1-tuberculosinyl adenosine dissolved in $CD_3OD$; HMQC NMR spectra of *M. tuberculosis* 1-TbAd showing $^{13}C$ resonances of carbon atoms bonded to at least one hydrogen(s) and the corresponding $^{1}H$ resonance(s); and NOESY NMR spectra of *M. tuberculosis* 1-TbAd (data not shown). Expanded views of NOSEY showed correlation of two olefinic protons with nearby terpenoid and adenine protons or ribose resonances.

Synthesis of Tuberculosinyl Pyrophosphate (TbPP).

To a solution of TTBAHPP (58 mg, 64.3 μmol, 2 eq.) in $CH_3CN$ (1 mL), in an oven-dried Schlenk flask under nitrogen atmosphere was added a solution of tuberculosinyl chloride (15) (10 mg, 32.2 μmol) in dry $CH_3CN$ (0.5 mL). The solution was stirred for 3 h after which TLC analysis, using n-pentane as an eluent, indicated complete conversion of the starting material. The solvent was removed under reduced pressure after which the residue was dissolved in dry methanol and passed through a pre-washed column DOWEX® 50WX2 $Na^+$-form (50-100 mesh). This process was repeated twice after which the methanol was evaporated. High Resolution Mass Spectrometry (APCI) analysis detected tuberculosinol PP [M-OPP]$^+$ at 273.2581 m/z ($C_{20}H_{33}$, calculated m/z 273.2577). The compound was used without further purification. For a more detailed procedure see Davisson, V. J. et al (16).

We determined the structure of *M. tuberculosis* Rv3378c and determined the initial electron density map of Rv3378c. Density modified map (2.0 σ, 2.30-Å resolution) from single-wavelength anomalous dispersion (SAD) phasing of a mercury derivative (Ethylmercury phosphate) dataset was superimposed on the model of Rv3378c (data not shown). From superimposition of Rv3378c and Rv2361c (rmsd=2.65 for 406 Cα atoms) we observed an ordered P-loop in a nonphysiological complex with mellitic acid. We generated Ribbon diagrams of Rv3378c apo and Rv3378c:mellitic acid complex (data not shown). The P-loop (residues 80-95) of apo and mellitic acid complex.

Database S1

XCMS software was used in R environment to list detected features from the HPLC-MS dataset obtained for *M. tuberculosis* and *M. bovis* BCG lipid extracts. Among all detected features, this list shows those features that pass the filters of a minimum fold change intensity of 2 and a corrected t-test p-value <0.05.

RESULTS AND DISCUSSION REFERENCES

1. Dye C, Glaziou P, Floyd K, & Raviglione M (2013) Prospects for tuberculosis elimination. *Annu Rev Public Health* 34:271-286.
2. Sturgill-Koszycki S, et al. (1994) Lack of acidification in *Mycobacterium* phagosomes produced by exclusion of the vesicular proton-ATPase. *Science* 263(5147):678-681.
3. Camus J C, Pryor M J, Medigue C, & Cole S T (2002) Re-annotation of the genome sequence of *Mycobacterium tuberculosis* H37Rv. *Microbiology* 148(Pt 10):2967-2973.
4. Layre E, et al. (2011) A comparative lipidomics platform for chemotaxonomic analysis of *Mycobacterium tuberculosis*. *Chem Biol* 18(12):1537-1549.
5. Sartain M J, Dick D L, Rithner C D, Crick D C, & Belisle J T (2011) Lipidomic analyses of *Mycobacterium tuberculosis* based on accurate mass measurements and the novel "Mtb LipidDB". *J Lipid Res* 52(5):861-872.
6. Behr M A, et al. (1999) Comparative genomics of BCG vaccines by whole-genome DNA microarray. *Science* 284(5419):1520-1523.
7. Mahairas G G, Sabo P J, Hickey M J, Singh D C, & Stover C K (1996) Molecular analysis of genetic differences between *Mycobacterium bovis* BCG and virulent *M. bovis*. *J Bacteriol* 178(5):1274-1282.
8. Brodin P, Rosenkrands I, Andersen P, Cole S T, & Brosch R (2004) ESAT-6 proteins: protective antigens and virulence factors? *Trends Microbiol* 12(11):500-508.
9. Fortune S M, et al. (2005) Mutually dependent secretion of proteins required for mycobacterial virulence. *Proc Natl Acad Sci USA* 102(30):10676-10681.
10. Nakano C, et al. (2011) Characterization of the Rv3378c gene product, a new diterpene synthase for producing tuberculosinol and (13R, S)-isotuberculosinol (nosyberkol), from the *Mycobacterium tuberculosis* H37Rv genome. *Biosci Biotechnol Biochem* 75(1):75-81.
11. Mann F M, et al. (2009) Characterization and inhibition of a class II diterpene cyclase from *Mycobacterium tuberculosis*: implications for tuberculosis. *J Biol Chem* 284(35):23574-23579.
12. Mann F M, et al. (2009) Edaxadiene: a new bioactive diterpene from *Mycobacterium tuberculosis*. *J Am Chem Soc* 131(48):17526-17527.
13. Pethe K, et al. (2004) Isolation of *Mycobacterium tuberculosis* mutants defective in the arrest of phagosome maturation. *Proc Natl Acad Sci USA* 101(37):13642-13647.
14. Domenech P, et al. (2004) The role of MmpL8 in sulfatide biogenesis and virulence of *Mycobacterium tuberculosis*. *J Biol Chem* 279(20):21257-21265.
15. Jain M & Cox J S (2005) Interaction between polyketide synthase and transporter suggests coupled synthesis and export of virulence lipid in *M. tuberculosis*. *PLoS Pathog* 1(1):e2.
16. Converse S E, et al. (2003) MmpL8 is required for sulfolipid-1 biosynthesis and *Mycobacterium tuberculosis* virulence. *Proc Natl Acad Sci USA* 100(10):6121-6126.
17. Garces A, et al. (2010) EspA acts as a critical mediator of ESX1-dependent virulence in *Mycobacterium tuberculosis* by affecting bacterial cell wall integrity. *PLoS Pathog* 6(6):e1000957.
18. Prach L, Kirby J, Keasling J D, & Alber T (2010) Diterpene production in *Mycobacterium tuberculosis*. *Febs J* 277(17):3588-3595.
19. Nakano C, Okamura T, Sato T, Dairi T, & Hoshino T (2005) *Mycobacterium tuberculosis* H37Rv3377c encodes the diterpene cyclase for producing the halimane skeleton. *Chem Commun (Camb)* (8):1016-1018.
20. Nakano C & Hoshino T (2009) Characterization of the Rv3377c gene product, a type-B diterpene cyclase, from the *Mycobacterium tuberculosis* H37 genome. *Chembiochem* 10(12):2060-2071.
21. Hoshino T, Nakano C, Ootsuka T, Shinohara Y, & Hara T (2011) Substrate specificity of Rv3378c, an enzyme from *Mycobacterium tuberculosis*, and the inhibitory activity of the bicyclic diterpenoids against macrophage phagocytosis. *Org Biomol Chem* 9(7):2156-2165.
22. Ottria R, Casati S, Baldoli E, Maier J A, & Ciuffreda P (2010) N(6)-Alkyladenosines: Synthesis and evaluation of in vitro anticancer activity. *Bioorg Med Chem* 18(23): 8396-8402.
23. Casati S, Manzocchi A, Ottria R, & Ciuffreda P (2010) 1H, 13C and 15N NMR assignments for N6-isopentenyladenosine/inosine analogues. *Magn Reson Chem* 48(9):745-748.
24. Casati S, Manzocchi A, Ottria R, & Ciuffreda P (2011) 1H, 13C and 15N NMR spectral assignments of adenosine derivatives with different amino substituents at C6-position. *Magn Reson Chem* 49(5):279-283.
25. Sassetti C M, Boyd D H, & Rubin E J (2001) Comprehensive identification of conditionally essential genes in mycobacteria. *Proc Natl Acad Sci USA* 98(22):12712-12717.
26. Mann F M, Xu M, Davenport E K, & Peters R J (2012) Functional characterization and evolution of the isotuberculosinol operon in *Mycobacterium tuberculosis* and related Mycobacteria. *Front Microbiol* 3:368.
27. Kurokawa H & Koyama T (2010) *Comprehensive Natural Products II: Chemistry and Biology* (Elsevier Ltd) 2010 Ed.
28. Chang S Y, Ko T P, Chen A P, Wang A H, & Liang P H (2004) Substrate binding mode and reaction mechanism of undecaprenyl pyrophosphate synthase deduced from crystallographic studies. *Protein Sci* 13(4):971-978.
29. Wang W, et al. (2008) The structural basis of chain length control in Rv1086. *J Mol Biol* 381(1):129-140.
30. Guo R T, et al. (2005) Crystal structures of undecaprenyl pyrophosphate synthase in complex with magnesium, isopentenyl pyrophosphate, and farnesyl thiopyrophosphate: roles of the metal ion and conserved residues in catalysis. *J Biol Chem* 280(21):20762-20774.
31. Sato T, Kigawa A, Takagi R, Adachi T, & Hoshino T (2008) Biosynthesis of a novel cyclic C35-terpene via the cyclisation of a Z-type C35-polyprenyl diphosphate obtained from a nonpathogenic *Mycobacterium* species. *Org Biomol Chem* 6(20):3788-3794.
32. Sato T, Takagi R, Orito Y, Ono E, & Hoshino T (2010) Novel compounds of octahydroheptaprenyl mycolic acyl ester and monocyclic C35-terpene, heptaprenylcycline B, from non-pathogenic *mycobacterium* species. *Biosci Biotechnol Biochem* 74(1):147-151.
33. Vik A, et al. (2007) Antimicrobial and cytotoxic activity of agelasine and agelasimine analogs. *Bioorg Med Chem* 15(12):4016-4037.
34. Yates R M, Hermetter A, & Russell D G (2005) The kinetics of phagosome maturation as a function of phagosome/lysosome fusion and acquisition of hydrolytic activity. *Traffic* 6(5):413-420.

We claim:
1. A method for treatment of *Mycobacterium tuberculosis* comprising:
   a. identifying in a biological sample the presence of at least one compound selected from the group consisting of:

$R^1$ is H or $R^2$ is absent or provided that one of $R^2$ and $R^3$ is $R^3$ and $R^4$ are selected independently from hydrogen, mycolic acids, and any combinations thereof, provided that at least one of $R^3$ and $R^4$ is a mycolic acid b. administering a pharmaceutically effective amount of a *Mycobacterium tuberculosis* therapeutic to a subject identified as having at least one compound.

2. The method of claim 1, wherein the compound is wherein one of the 2' or 3' hydroxyl H in the above structure is replaced with C85 methoxy mycolate or C78 alpha mycolate,
wherein C85 methoxy mycolate has the structure of

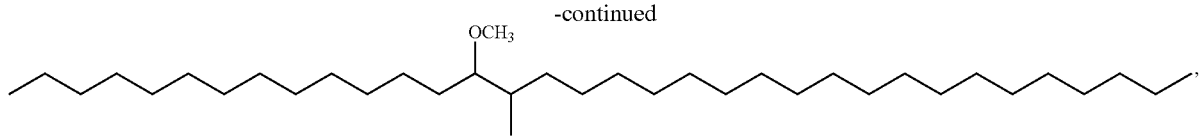

and C78 alpha mycolate has the structure of

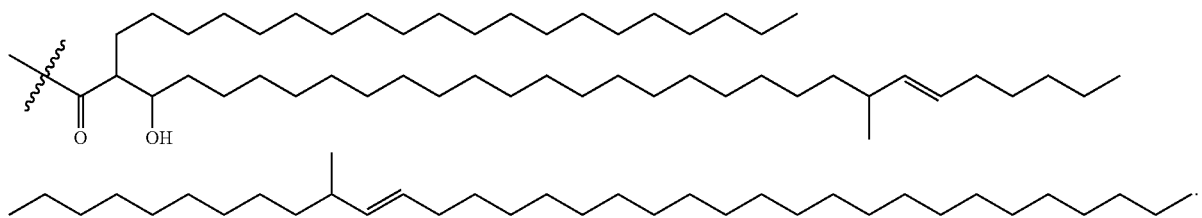

3. The method of claim 1, wherein the subject is human.

4. The method of claim 1, wherein prior to administering, the presence of the compound is measured in a biological sample obtained from the subject using an assay selected from the group consisting of: mass spectrometry (MS), nuclear magnetic resonance spectroscopy and an immunoassay.

5. The method of claim 4, wherein the assay is an immunoassay that detects the presence of the compound/s by monitoring the presence of host antibodies directed against the compound/s.

6. The method of claim 4, wherein the assay is an immunoassay that uses a non-host antibody that specifically binds to a compound selected from the group consisting of:

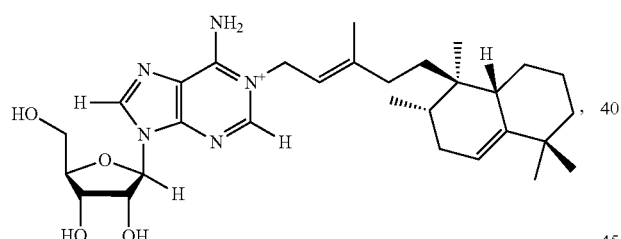

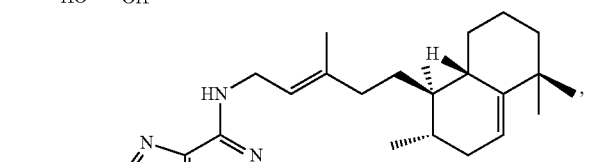

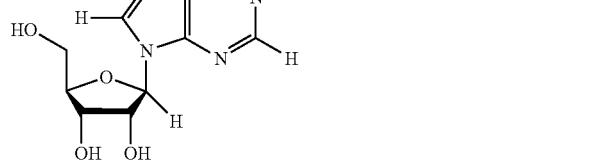

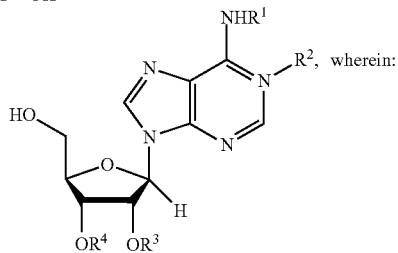

-continued

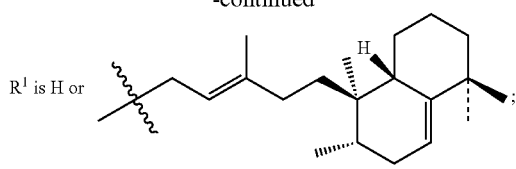

$R^1$ is H or

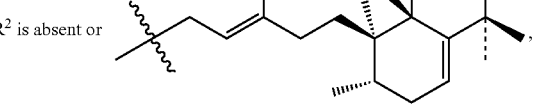

$R^2$ is absent or provided that one of $R^2$ and $R^3$ is

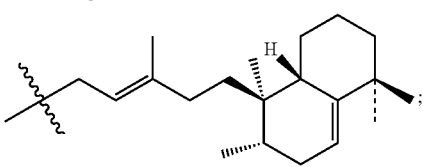

$R^3$ and $R^4$ are selected independently from hydrogen, mycolic acids, and any combinations thereof, provided that at least one of $R^3$ and $R^4$ is a mycolic acid; and

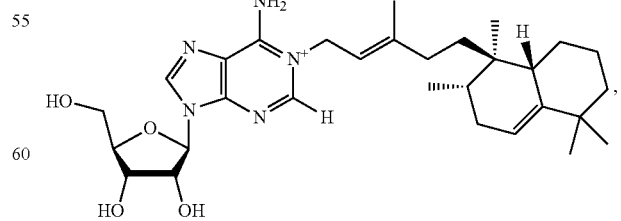

wherein one of the 2' or 3' hydroxyl H in the above structure is replaced with C85 methoxy mycolate or C78 alpha mycolate, wherein C85 methoxy mycolate has the structure of

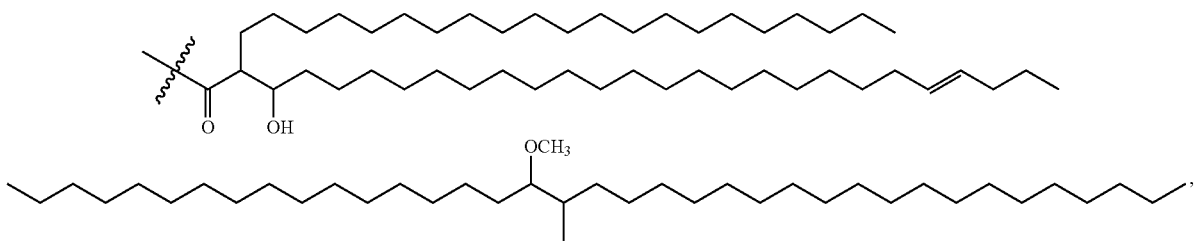

and C78 alpha mycolate has the structure of

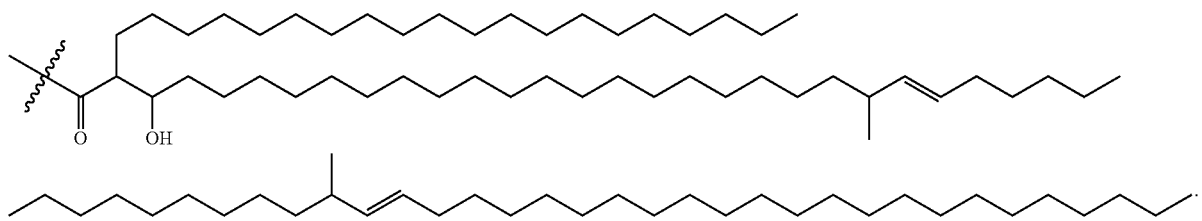

7. The method of claim 1, wherein the biological sample is selected from the group consisting of: breath, sputum, blood, urine, gastric lavage, pleural fluid, lung tissue, lymphoid tissue, paranasal sinuses, bronchi, a bronchiole, alveolus, ciliated mucosal epithelia of the respiratory tract, mucosal epithelia of the respiratory tract, squamous epithelial cells of the respiratory tract, a mast cell, a goblet cell, a pneumocyte (type 1 or type 2), broncheoalveolar lavage fluid (BAL), alveolar lining fluid, an intra epithelial dendritic cell, sputum, mucus, saliva, blood, serum, plasma, a peripheral blood mononuclear cell (PBMC), a neutrophil, and a monocyte.

* * * * *